United States Patent
Doshan et al.

(10) Patent No.: US 9,597,327 B2
(45) Date of Patent: *Mar. 21, 2017

(54) SYNTHESIS OF (R)-N-METHYLNALTREXONE

(71) Applicant: Progenics Pharmaceuticals, Inc., Tarrytown, NY (US)

(72) Inventors: Harold D. Doshan, Riverside, CT (US); Julio Perez, Tarrytown, NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/746,513

(22) Filed: Jun. 22, 2015

(65) Prior Publication Data

US 2015/0290187 A1   Oct. 15, 2015

Related U.S. Application Data

(60) Continuation of application No. 14/218,585, filed on Mar. 18, 2014, now abandoned, which is a continuation of application No. 13/670,846, filed on Nov. 7, 2012, now abandoned, which is a continuation of application No. 12/692,083, filed on Jan. 22, 2010, now Pat. No. 8,343,992, which is a division of application No. 11/441,395, filed on May 25, 2006, now Pat. No. 7,674,904.

(60) Provisional application No. 60/684,616, filed on May 25, 2005.

(51) Int. Cl.
| | |
|---|---|
| *A61K 31/485* | (2006.01) |
| *C07D 489/08* | (2006.01) |
| *A61K 45/06* | (2006.01) |
| *C07D 489/04* | (2006.01) |
| *G01N 33/15* | (2006.01) |

(52) U.S. Cl.
CPC ............ *A61K 31/485* (2013.01); *A61K 45/06* (2013.01); *C07D 489/04* (2013.01); *C07D 489/08* (2013.01); *G01N 33/15* (2013.01); *Y10T 436/141111* (2015.01)

(58) Field of Classification Search
USPC ............................................ 514/282; 546/45
See application file for complete search history.

(56) References Cited

U.S. PATENT DOCUMENTS

| | | |
|---|---|---|
| 3,714,159 A | 1/1973 | Janssen et al. |
| 3,723,440 A | 3/1973 | Freter et al. |
| 3,854,480 A | 12/1974 | Zaffaroni |
| 3,884,916 A | 5/1975 | Janssen et al. |
| 3,937,801 A | 2/1976 | Lippmann |
| 3,996,214 A | 12/1976 | Dajani et al. |
| 4,012,393 A | 3/1977 | Markos et al. |
| 4,013,668 A | 3/1977 | Adelstein et al. |
| 4,025,652 A | 5/1977 | Diamond et al. |
| 4,060,635 A | 11/1977 | Diamond et al. |
| 4,066,654 A | 1/1978 | Adelstein et al. |
| 4,069,223 A | 1/1978 | Adelstein |
| 4,072,686 A | 2/1978 | Adelstein et al. |
| 4,115,400 A | 9/1978 | Zimmerman |
| 4,115,564 A | 9/1978 | Diamond et al. |
| 4,116,963 A | 9/1978 | Adelstein |
| 4,125,531 A | 11/1978 | Yen |
| 4,176,186 A | 11/1979 | Goldberg et al. |
| 4,194,045 A | 3/1980 | Adelstein |
| 4,203,920 A | 5/1980 | Diamond et al. |
| 4,241,066 A | 12/1980 | Kobylecki et al. |
| 4,277,605 A | 7/1981 | Buyniski et al. |
| 4,311,833 A | 1/1982 | Namikoshi et al. |
| 4,322,426 A | 3/1982 | Hermann et al. |
| 4,326,074 A | 4/1982 | Diamond et al. |
| 4,326,075 A | 4/1982 | Diamond et al. |
| 4,377,568 A | 3/1983 | Chopra |
| 4,385,078 A | 5/1983 | Onda et al. |
| 4,427,676 A | 1/1984 | White et al. |
| 4,430,327 A | 2/1984 | Frederickson |
| 4,452,775 A | 6/1984 | Kent |
| 4,457,907 A | 7/1984 | Porter |
| 4,462,839 A | 7/1984 | McGinley et al. |
| 4,466,968 A | 8/1984 | Bernstein |
| 4,518,433 A | 5/1985 | McGinley et al. |
| 4,533,739 A | 8/1985 | Pitzele et al. |
| 4,556,552 A | 12/1985 | Porter et al. |
| 4,606,909 A | 8/1986 | Bechgaard et al. |
| 4,615,885 A | 10/1986 | Nakagame et al. |
| 4,670,287 A | 6/1987 | Tsuji |
| 4,675,189 A | 6/1987 | Kent et al. |

(Continued)

FOREIGN PATENT DOCUMENTS

| | | |
|---|---|---|
| AU | 610 561 B2 | 8/1988 |
| AU | 758416 B2 | 3/2003 |

(Continued)

OTHER PUBLICATIONS

[No Author Listed] Extracolonic Motility Abnormalities. Persistence of Abdominal Symptoms after Successful Surgery. Southern Medical Journal. 2002;95(9);1042-1046.

[No Author Listed] Methylnaltrexone: MNTX. Drugs R D. 2006;7(6):374-8.

[No Author Listed] Oncology. 1996;10(12):1880.

[No Author Listed] Pain management; cancer-pain remedy wins orphan drug status. Cancer Biotechnology Weekly. Aug. 12, 1996; 2 pages.

[No Author Listed] Pathophysiology. Medscape General Medicine. 2005;7(3):17.

[No Author Listed] Progenics achieves enrollment target in pivotal phase 3 clinical trial of methylnaltrexone for opioid-induced constipation. Press Release. Progenics Pharmaceuticals, Inc. Dec. 3, 2004.

(Continued)

*Primary Examiner* — Charanjit Aulakh
(74) *Attorney, Agent, or Firm* — McCarter & English, LLP; Jonathan M. Sparks, Esq.; Maneesh Gulati, Esq.

(57) ABSTRACT

This invention relates to stereoselective synthesis of R-MNTX and intermediates thereof, pharmaceutical preparations comprising R-MNTX or intermediates thereof and methods for their use.

26 Claims, 6 Drawing Sheets

(56) References Cited

U.S. PATENT DOCUMENTS

| | | |
|---|---|---|
| 4,689,332 A | 8/1987 | McLaughlin et al. |
| 4,719,215 A | 1/1988 | Goldberg |
| 4,730,048 A | 3/1988 | Portoghese |
| 4,765,978 A | 8/1988 | Abidi et al. |
| 4,806,556 A | 2/1989 | Portoghese |
| 4,824,853 A | 4/1989 | Wals et al. |
| 4,836,212 A | 6/1989 | Schmitt et al. |
| 4,837,214 A | 6/1989 | Tanaka et al. |
| 4,857,533 A | 8/1989 | Sherman et al. |
| 4,861,781 A | 8/1989 | Goldberg |
| 4,863,928 A | 9/1989 | Atkinson et al. |
| 4,867,979 A | 9/1989 | Sheth et al. |
| 4,870,084 A | 9/1989 | Eggler et al. |
| 4,888,346 A | 12/1989 | Bihari et al. |
| 4,891,379 A | 1/1990 | Zimmerman et al. |
| 4,912,114 A | 3/1990 | Revesz |
| 4,965,269 A | 10/1990 | Brandstrom et al. |
| 4,987,136 A | 1/1991 | Kreek et al. |
| 4,990,521 A | 2/1991 | Van Daele et al. |
| 4,999,342 A | 3/1991 | Ahmad et al. |
| 5,102,887 A | 4/1992 | Goldberg |
| 5,116,868 A | 5/1992 | Chen et al. |
| 5,133,974 A | 7/1992 | Paradissis et al. |
| 5,159,081 A | 10/1992 | Cantrell et al. |
| 5,202,159 A | 4/1993 | Chen et al. |
| 5,220,017 A | 6/1993 | Bock et al. |
| 5,236,947 A | 8/1993 | Calvet et al. |
| 5,250,542 A | 10/1993 | Cantrell et al. |
| 5,256,154 A | 10/1993 | Liebert et al. |
| 5,270,328 A | 12/1993 | Cantrell et al. |
| 5,312,899 A | 5/1994 | Schiller |
| 5,391,372 A | 2/1995 | Campbell |
| 5,407,686 A | 4/1995 | Patel et al. |
| 5,426,112 A | 6/1995 | Zagon et al. |
| 5,434,171 A | 7/1995 | Frank et al. |
| 5,472,943 A | 12/1995 | Crain et al. |
| 5,512,578 A | 4/1996 | Crain et al. |
| 5,536,507 A | 7/1996 | Abramowitz et al. |
| 5,567,423 A | 10/1996 | Ying |
| 5,585,348 A | 12/1996 | Crain et al. |
| 5,591,433 A | 1/1997 | Michael et al. |
| 5,597,564 A | 1/1997 | Ying |
| 5,609,871 A | 3/1997 | Michael et al. |
| 5,614,219 A | 3/1997 | Wunderlich et al. |
| 5,614,222 A | 3/1997 | Kaplan |
| 5,626,875 A | 5/1997 | Ballester Rodes et al. |
| 5,629,001 A | 5/1997 | Michael et al. |
| 5,656,290 A | 8/1997 | Kelm et al. |
| 5,686,072 A | 11/1997 | Uhr et al. |
| 5,714,586 A | 2/1998 | Kunstmann et al. |
| 5,739,152 A | 4/1998 | Andersson et al. |
| 5,767,125 A | 6/1998 | Crain et al. |
| 5,804,595 A | 9/1998 | Portoghese et al. |
| 5,811,451 A | 9/1998 | Minoia et al. |
| 5,821,219 A | 10/1998 | Grandy et al. |
| 5,866,154 A | 2/1999 | Bahal et al. |
| 5,866,164 A | 2/1999 | Kuczynski et al. |
| 5,958,452 A | 9/1999 | Oshlack et al. |
| 5,972,954 A | 10/1999 | Foss et al. |
| 5,981,185 A | 11/1999 | Matson et al. |
| RE36,547 E | 2/2000 | Crain et al. |
| 6,025,154 A | 2/2000 | Li et al. |
| 6,096,756 A | 8/2000 | Crain et al. |
| 6,096,763 A | 8/2000 | Hoffman et al. |
| 6,096,764 A | 8/2000 | Bryant et al. |
| 6,099,853 A | 8/2000 | Hertelendy et al. |
| 6,136,780 A | 10/2000 | Zagon et al. |
| 6,153,620 A | 11/2000 | Kornetsky |
| 6,190,691 B1 | 2/2001 | Mak |
| 6,194,382 B1 | 2/2001 | Crain et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,353,004 B1 | 3/2002 | Farrar et al. |
| 6,359,111 B1 | 3/2002 | Meyer et al. |
| 6,362,194 B1 | 3/2002 | Crain et al. |
| 6,384,044 B1 | 5/2002 | Bihari |
| 6,395,705 B2 | 5/2002 | Crain et al. |
| 6,419,959 B1 | 7/2002 | Walter et al. |
| 6,426,094 B2 | 7/2002 | Piver et al. |
| 6,451,806 B2 | 9/2002 | Farrar |
| 6,455,537 B1 | 9/2002 | Cooper |
| 6,469,030 B2 | 10/2002 | Farrar et al. |
| 6,479,500 B1 | 11/2002 | Fukushima et al. |
| 6,559,158 B1 | 5/2003 | Foss et al. |
| 6,608,075 B2 | 8/2003 | Foss et al. |
| 6,693,125 B2 | 2/2004 | Borisy et al. |
| 6,696,066 B2 | 2/2004 | Kaiko et al. |
| 6,720,336 B2 | 4/2004 | Liras |
| 6,723,712 B2 | 4/2004 | Bourhis et al. |
| 6,734,188 B1 | 5/2004 | Rhodes et al. |
| 6,756,364 B2 | 6/2004 | Barbier et al. |
| 6,777,534 B1 | 8/2004 | Klagsbrun et al. |
| 6,794,370 B2 | 9/2004 | Achterrath |
| 6,800,639 B2 | 10/2004 | Giles et al. |
| 6,833,349 B2 | 12/2004 | Xia et al. |
| 6,838,469 B2 | 1/2005 | Sumegi |
| 6,884,879 B1 | 4/2005 | Baca et al. |
| 6,900,234 B1 | 5/2005 | Fossa |
| 6,946,556 B1 | 9/2005 | Likhotvorik et al. |
| 6,960,596 B2 | 11/2005 | Bissery |
| 6,967,016 B2 | 11/2005 | van Gemen et al. |
| 6,984,403 B2 | 1/2006 | Hagen et al. |
| 6,986,901 B2 | 1/2006 | Meisel et al. |
| 6,989,383 B1 | 1/2006 | Rosen et al. |
| 6,992,106 B2 | 1/2006 | Morinaga et al. |
| 7,012,100 B1 | 3/2006 | Edwards et al. |
| 7,074,825 B2 | 7/2006 | Mo et al. |
| 7,094,775 B2 | 8/2006 | Strugnell et al. |
| 7,129,265 B2 | 10/2006 | Mason |
| 7,132,554 B2 | 11/2006 | Rose |
| 7,141,554 B2 | 11/2006 | Rochat et al. |
| 7,160,913 B2 | 1/2007 | Schneider |
| 7,183,269 B2 | 2/2007 | Kreutz |
| 7,196,115 B2 | 3/2007 | Khanuja et al. |
| 7,259,233 B2 | 8/2007 | Dodd et al. |
| 7,501,434 B2 | 3/2009 | Shah et al. |
| 7,563,899 B2 | 7/2009 | Boyd et al. |
| 7,622,441 B2 | 11/2009 | Mickle et al. |
| 7,674,904 B2 | 3/2010 | Doshan et al. |
| 8,003,794 B2 | 8/2011 | Boyd et al. |
| 8,343,992 B2 | 1/2013 | Doshan et al. |
| 8,916,581 B2 | 12/2014 | Boyd et al. |
| 9,102,680 B2 * | 8/2015 | Smolenskaya ....... C07D 489/04 |
| 2001/0010919 A1 | 8/2001 | Grandy et al. |
| 2001/0018413 A1 | 8/2001 | Crain et al. |
| 2001/0033865 A1 | 10/2001 | Oshlack et al. |
| 2001/0036469 A1 | 11/2001 | Gooberman |
| 2001/0036476 A1 | 11/2001 | Oshlack et al. |
| 2001/0036951 A1 | 11/2001 | Farrar et al. |
| 2001/0046968 A1 | 11/2001 | Zagon et al. |
| 2001/0047005 A1 | 11/2001 | Farrar |
| 2002/0028825 A1 | 3/2002 | Foss et al. |
| 2002/0064771 A1 | 5/2002 | Zhong et al. |
| 2002/0068712 A1 | 6/2002 | Stevens |
| 2002/0173466 A1 | 11/2002 | Crain et al. |
| 2002/0176888 A1 | 11/2002 | Bartholomaeus et al. |
| 2002/0188005 A1 | 12/2002 | Farrar et al. |
| 2003/0022909 A1 | 1/2003 | Moss et al. |
| 2003/0026801 A1 | 2/2003 | Weiner et al. |
| 2003/0039689 A1 | 2/2003 | Chen et al. |
| 2003/0065003 A1 | 4/2003 | Foss et al. |
| 2003/0105121 A1 | 6/2003 | Bihari |
| 2003/0124086 A1 | 7/2003 | Bentley et al. |
| 2003/0144312 A1 | 7/2003 | Schoenhard |
| 2003/0158220 A1 | 8/2003 | Foss et al. |
| 2003/0187010 A1 | 10/2003 | Foss et al. |
| 2003/0191147 A1 | 10/2003 | Sherman et al. |
| 2003/0219406 A1 | 11/2003 | Schroit et al. |
| 2004/0010996 A1 | 1/2004 | Karlstrom et al. |
| 2004/0010997 A1 | 1/2004 | Close |
| 2004/0010998 A1 | 1/2004 | Turco |
| 2004/0024006 A1 | 2/2004 | Simon |
| 2004/0136908 A1 | 7/2004 | Olson et al. |

(56) References Cited

U.S. PATENT DOCUMENTS

| | | |
|---|---|---|
| 2004/0162306 A1 | 8/2004 | Foss et al. |
| 2004/0162307 A1 | 8/2004 | Foss et al. |
| 2004/0162308 A1 | 8/2004 | Foss et al. |
| 2004/0167147 A1 | 8/2004 | Foss et al. |
| 2004/0167148 A1 | 8/2004 | Foss et al. |
| 2004/0180916 A1 | 9/2004 | Levine |
| 2004/0242523 A1 | 12/2004 | Weichselbaum et al. |
| 2004/0254156 A1 | 12/2004 | Le Bourdonnec et al. |
| 2004/0254208 A1 | 12/2004 | Weber et al. |
| 2004/0259898 A1 | 12/2004 | Moss |
| 2004/0259899 A1 | 12/2004 | Sanghvi et al. |
| 2004/0266806 A1 | 12/2004 | Sanghvi et al. |
| 2005/0004029 A1 | 1/2005 | Garcia |
| 2005/0004155 A1 | 1/2005 | Boyd et al. |
| 2005/0011468 A1 | 1/2005 | Moss |
| 2005/0048117 A1 | 3/2005 | Foss et al. |
| 2005/0085514 A1 | 4/2005 | Cosford et al. |
| 2005/0124657 A1 | 6/2005 | Christ et al. |
| 2005/0124885 A1 | 6/2005 | Abend et al. |
| 2005/0187255 A1 | 8/2005 | Lee et al. |
| 2006/0025592 A1 | 2/2006 | Stranix et al. |
| 2006/0063792 A1 | 3/2006 | Dolle et al. |
| 2006/0094658 A1 | 5/2006 | Currie et al. |
| 2006/0115424 A1 | 6/2006 | Gray |
| 2006/0128742 A1 | 6/2006 | Edwards et al. |
| 2006/0204512 A1 | 9/2006 | Krasnoperov et al. |
| 2006/0205753 A1 | 9/2006 | Israel |
| 2006/0258696 A1 | 11/2006 | Moss et al. |
| 2007/0010450 A1 | 1/2007 | Currie et al. |
| 2007/0020261 A1 | 1/2007 | Sliwkowski et al. |
| 2007/0060501 A1 | 3/2007 | Jhamandas et al. |
| 2007/0071761 A1 | 3/2007 | Seon |
| 2007/0082044 A1 | 4/2007 | Yeum |
| 2007/0099946 A1 | 5/2007 | Doshan et al. |
| 2007/0265293 A1 | 11/2007 | Boyd et al. |
| 2008/0064743 A1 | 3/2008 | Shah et al. |
| 2008/0064744 A1 | 3/2008 | Shah et al. |
| 2008/0070975 A1 | 3/2008 | Shah et al. |
| 2008/0075771 A1 | 3/2008 | Vaughn et al. |
| 2008/0103438 A1 | 5/2008 | Prais et al. |
| 2008/0194611 A1 | 8/2008 | Alverdy et al. |
| 2008/0274119 A1 | 11/2008 | Moss et al. |
| 2009/0312359 A1 | 12/2009 | Foss et al. |
| 2010/0087472 A1 | 4/2010 | Foss et al. |
| 2010/0099699 A1 | 4/2010 | Melucci |
| 2010/0105911 A1 | 4/2010 | Boyd et al. |
| 2010/0120813 A1 | 5/2010 | Bazhina et al. |
| 2010/0249169 A1 | 9/2010 | Shah et al. |
| 2010/0261744 A1 | 10/2010 | Sanghvi et al. |
| 2010/0261745 A1 | 10/2010 | Sanghvi et al. |
| 2010/0261746 A1 | 10/2010 | Sanghvi et al. |
| 2010/0267758 A1 | 10/2010 | Sanghvi et al. |
| 2010/0305323 A1 | 12/2010 | Smolenskaya et al. |
| 2013/0323286 A1 | 12/2013 | Doshan et al. |
| 2015/0057303 A1 | 2/2015 | Doshan et al. |

FOREIGN PATENT DOCUMENTS

| | | |
|---|---|---|
| AU | 2003204844 B2 | 6/2007 |
| BE | 876 968 A1 | 10/1979 |
| CA | 2 064 373 A1 | 9/1992 |
| CA | 1 315 689 C | 4/1993 |
| CA | 2312234 A1 | 3/2005 |
| DE | 3 780 819 T2 | 1/1993 |
| DE | 4 303 214 A1 | 8/1994 |
| DE | 196 51 551 A1 | 6/1998 |
| EP | 0 278 821 A1 | 8/1988 |
| EP | 0 289 070 A1 | 11/1988 |
| EP | 0 306 575 A1 | 3/1989 |
| EP | 0 352 361 A1 | 1/1990 |
| EP | 0 506 468 A1 | 9/1992 |
| EP | 0 643 967 A2 | 3/1995 |
| EP | 0 663 401 A1 | 7/1995 |
| EP | 0 760 661 A1 | 3/1997 |
| EP | 0 984 004 A2 | 3/2000 |
| EP | 1 047 726 A1 | 11/2000 |
| ES | 2226933 T3 | 4/2005 |
| GB | 1 202 148 A | 8/1970 |
| JP | 1 068 376 A | 3/1989 |
| JP | 2-25427 | 1/1990 |
| JP | 2 625 457 B2 | 7/1997 |
| JP | 4-183371 B2 | 11/2008 |
| JP | 4-217924 B2 | 2/2009 |
| JP | 4-225922 B2 | 2/2009 |
| JP | 5-213763 B2 | 6/2013 |
| NZ | 222911 A | 11/1990 |
| SG | 116167 | 1/2008 |
| WO | WO-83/03197 A1 | 9/1983 |
| WO | WO-88/05297 A1 | 7/1988 |
| WO | WO-93/20826 A1 | 10/1993 |
| WO | WO-94/10202 A1 | 5/1994 |
| WO | WO-95/31985 A2 | 11/1995 |
| WO | WO-96/14058 A1 | 5/1996 |
| WO | WO-96/23793 A1 | 8/1996 |
| WO | WO-97/07118 A1 | 2/1997 |
| WO | WO-97/29739 A2 | 8/1997 |
| WO | WO-97/33566 A2 | 9/1997 |
| WO | WO-98/25613 A2 | 6/1998 |
| WO | WO-99/22737 A1 | 5/1999 |
| WO | WO-99/36470 A1 | 7/1999 |
| WO | WO-99/40089 A1 | 8/1999 |
| WO | WO-01/13909 A2 | 3/2001 |
| WO | WO-01/32180 A2 | 5/2001 |
| WO | WO-01/37785 A2 | 5/2001 |
| WO | WO-01/41705 A2 | 6/2001 |
| WO | WO-01/42207 A2 | 6/2001 |
| WO | WO-01/70031 A1 | 9/2001 |
| WO | WO-01/85257 A2 | 11/2001 |
| WO | WO-02/060870 A2 | 8/2002 |
| WO | WO-02/098422 A1 | 12/2002 |
| WO | WO-03/020296 A1 | 3/2003 |
| WO | WO-03/032990 A2 | 4/2003 |
| WO | WO-03/037340 A1 | 5/2003 |
| WO | WO-03/077867 A2 | 9/2003 |
| WO | WO-2004/014291 A2 | 2/2004 |
| WO | WO-2004/043964 A2 | 5/2004 |
| WO | WO-2004/080996 A1 | 9/2004 |
| WO | WO-2004/091623 A1 | 10/2004 |
| WO | WO-2006/096626 A2 | 9/2006 |
| WO | WO-2006/127898 A2 | 11/2006 |
| WO | WO-2006/127899 A2 | 11/2006 |
| WO | WO-2006/132963 A2 | 12/2006 |
| WO | WO-2006/135650 A1 | 12/2006 |
| WO | WO-2007/053194 A2 | 5/2007 |
| WO | WO-2007/053698 A2 | 5/2007 |
| WO | WO-2007/131154 A2 | 11/2007 |
| WO | WO-2008/016704 A1 | 2/2008 |
| WO | WO-2008/019115 A2 | 2/2008 |
| WO | WO-2008/064150 A1 | 5/2008 |
| WO | WO-2008/064351 A2 | 5/2008 |
| WO | WO-2008/064353 A2 | 5/2008 |
| WO | WO-2008/070462 A2 | 6/2008 |
| WO | WO-2008/121348 A2 | 10/2008 |
| WO | WO-2008/121860 A1 | 10/2008 |

OTHER PUBLICATIONS

[No Author Listed] Progenics announces positive top-line results from pivotal phase 3 clinical trial of MNTX in opioid-induced constipation. Press Release. Progenics Pharmaceuticals, Inc. Mar. 10, 2005.

[No Author Listed] Progenics initiates second phase 3 clinical trial of methylnaltrexone in opioid-induced constipation. Press Release. Progenics Pharmaceuticals, Inc. Jan. 13, 2004.

[No Author Listed] Remington's Pharmaceutical Sciences. 15th Edition. 1995: 1614-5.

[No Author Listed] Remington's Pharmaceutical Sciences. 15th Edition. 1995: 201-02, 273-74, 1466.

[No Author Listed] The Merck Manual. 17th edition. 1999:312-315.

Akinbami et al., Effect of a peripheral and a central acting opioid antagonist on the testicular response to stress in rats. Neuroendocrinology. Apr. 1994;59(4):343-8.

(56) References Cited

OTHER PUBLICATIONS

Altier et al., Opioid receptors in the ventral tegmental area contribute to stress-induced analgesia in the formalin test for tonic pain. Brain Res. Apr. 29, 1996;718(1-2):203-6.

Amin et al., Efficacy of methylnaltrexone versus naloxone for reversal of morphine-induced depression of hypoxic ventilatory response. Anesth Analg. Apr. 1994;78(4):701-5.

Amir et al., Endorphins in endotoxin-induced hyperglycemia in mice. Arch Toxicol Suppl. 1983;6:261-5.

Amir, Naloxone improves, and morphine exacerbates, experimental shock induced by release of endogenous histamine by compound 48/80. Brain Res. Apr. 9, 1984;297(1):187-90.

Arendt et al., Bidirectional effects of endogenous opioid peptides on endothelin release rates in porcine aortic endothelial cell culture: mediation by delta opioid receptor and opioid receptor antagonist-insensitive mechanisms. J Pharmacol ExpTher. Jan. 1995;272(1):1-7.

Arerangaiah et al., Opioids induce renal abnormalities in tumor-bearing mice. Nephron Exp Nephrol. 2007;105(3):e80-9. Epub Jan. 12, 2007.

Argentieri et al., Interaction of the opiate antagonist, naltrexone methyl bromide, with the acetylcholine receptor system of the motor end-plate. Brain Res. Oct. 31, 1983;277(2):377-9.

Armstead, Relationship among NO, the KATP channel, and opioids in hypoxic pial artery dilation. Am J Physiol. Sep. 1998;275(3 Pt 2):H988-94.

Armstrong et al., The gastrointestinal activity and peripheral selectivity of alvimopan, ADL08-0011, and naloxone in mice. May 21, 2006 DDW Presentation in Los Angeles. Clincial Phar Therap. 2005;77:74. Abstract #221957.

Attali et al., Kappa opiate agonists inhibit Ca2+ influx in rat spinal cord-dorsal root ganglion cocultures. Involvement of a GTP-binding protein. J Biol Chem. Jan. 5, 1989;264(1):347-53.

Aung et al., Methylnaltrexone prevents morphine-induced kaolin intake in the rat. Life Sci. Apr. 16, 2004;74(22):2685-91.

Aung et al., Scutellaria baicalensis decreases ritonavir-induced nausea. Aids Res Ther. Dec. 20, 2005;2:12.

Bagnol et al., Changes in enkephalin immunoreactivity of sympathetic ganglia and digestive tract of the cat after splanchnic nerve ligation. Regul Pept. Sep. 22, 1993;47(3):259-73. Abstract Only.

Baker et al., Functional effects of systemically administered agonists and antagonists of mu, delta, and kappa opioid receptor subtypes on body temperature in mice. J Pharmacol Exp Ther. Sep. 2002;302(3):1253-64.

Balasubramanian et al., Morphine sulfate inhibits hypoxia-induced vascular endothelial growth factor expression in endothelial cells and cardiac myocytes. J Mol Cell Cardiol. Dec. 2001;33(12):2179-87.

Baratti et al., Brain opioid peptides may participate in the reversal of pentylenetetrazol-induced amnesia. Methods Find Exp Clin Pharmacol. Sep. 1990;12(7):451-6.

Basilisco et al., Effect of loperamide and naloxone on mouth-to-caecum transit time evaluated by lactulose hydrogen breath test. Gut. Jul. 1985;26(7):700-3.

Basilisco et al., Oral naloxone antagonizes loperamide-induced delay of orocecal transit. Dig Dis Sci. Aug. 1987;32(8):829-32.

Bates, J.J., et al., "Are peripheral opioid antagonists the solution to opioid side effects?" *Anesth Analg.* (2004) 98:116-122.

Bedingfield et al., Methylnaltrexone attenuates taste aversion conditioned by low-dose ethanol. Alcohol. Jan. 1998;15(1):51-4.

Belcheva et al., μ-Opioid receptor-mediated ERK activation involves calmodulin-dependent epidermal growth factor receptor transactivation. J Biol Chem. Sep. 7, 2001;276(36):33847-53. Epub Jul. 16, 2001.

Belcheva et al., μ-opioid transactivation and down-regulation of the epidermal growth factor receptor in astrocytes: implications for mitogen-activated protein kinase signaling. Mol Pharmacol. Dec. 2003;64(6):1391-401.

Bianchetti et al., Quaternary derivatives of narcotic antagonists: stereochemical requirements at the chiral nitrogen for in vitro and in vivo activity. Life Sci. 1983;33 Suppl 1:415-8.

Bianchi et al., Quaternary narcotic antagonists' relative ability to prevent antinociception and gastrointestinal transit inhibition in morphine-treated rats as an index of peripheral selectivity. Life Sci. May 31, 1982;30(22):1875-83.

Bickel, Stimulation of colonic motility in dogs and rats by an enkephalin analogue pentapeptide. Life Sci. 1983;33 Suppl 1:469-72.

Bigliardi et al., Different expression of mu-opiate receptor in chronic and acute wounds and the effect of beta-endorphin on transforming growth factor beta type II receptor and cytokeratin 16 expression. J Invest Dermatol. Jan. 2003;120(1):145-52.

Bigliardi-Qi et al., Changes of epidermal mu-opiate receptor expression and nerve endings in chronic atopic dermatitis. Dermatology. 2005;210(2):91-9.

Binder et al., Effect of the peripherally selective kappa-opioid agonist, asimadoline, on adjuvant arthritis. Br J Pharmacol. Jun. 1998;124(4):647-54.

Blank et al., Central, stereoselective receptors mediate the acute effects of opiate antagonists on luteinizing hormone secretion. Life Sci. Oct. 27, 1986;39(17):1493-99.

Blebea et al., Differential effects of vascular growth factors on arterial and venous angiogenesis. J Vasc Surg. Mar. 2002;35(3):532-8.

Blebea et al., Opioid growth factor modulates angiogenesis. J Vasc Surg. Aug. 2000;32(2):364-73.

Bond et al., Investigation of small bowel transit time in man utilizing pulmonary hydrogen (H2) measurements. J Lab Clin Med. Apr. 1975;85(4):546-55. Abstract Only.

Bonn, Morphine stimulates tumour growth. Lancet Oncol. Sep. 2002;3(9):520.

Boonstra et al., Engineering novel biocatalytic routes for production of semisynthetic opiate drugs. Biomol Eng. Sep. 2001;18(2):41-7.

Bos et al., A Short and Efficient Synthesis of C-Nor-Dihydrocodeinone—The Antipode of Goto's Sinomenilone. Heterocycles. 1983;20(6):1077-81.

Bowen et al., Antagonism of the antinociceptive and discriminative stimulus effects of heroin and morphine by 3-methoxynaltrexone and naltrexone in rhesus monkeys. J Pharmacol Exp Ther. Jul. 2002;302(1):264-73.

Bowen et al., College on Problems of Drug Dependence 64.sup.th Annual Scientific Meeting. Jun. 8-13, 2002. Quebec City, Quebec, Canada. Abstracts. Drug Alcohol Depend. May 1, 2002;66 Suppl 1:S1-220. Abstract No. 65.

Breitbart et al., Control of non-pain symptoms in HIV/AIDS. J Back Musculoskelet Rehabil. 1997;8(3):243-46.

Brix-Christensen et al., Endogenous morphine is produced in response to cardiopulmonary bypass in neonatal pigs. Acta Anaesthesiol Scand. Nov. 2000;44(10):1204-8.

Brix-Christensen et al., Endogenous morphine levels increase following cardiac surgery as part of the nti-inflammatory response? Int J Cardiol. Dec. 19, 1997;62(3):191-7.

Brondsted et al., Hydrogels for site-specific drug delivery to the colon: in vitro and in vivo degradation. Pharm Res. Dec. 1992;9(12):1540-5. Abstract Only.

Brown et al., Opiate antagonists: central sites of action in suppressing water intake of the rat. Brain Res. Sep. 28, 1981;221(2):432-6.

Brown et al., Reversal of morphine-induced catalepsy in the rat by narcotic antagonists and their quaternary derivatives. Neuropharmacology. Mar. 1983;22(3):317-21.

Brown et al., Techniques for mechanical stimulation of cells in vitro: a review. J Biomech. Jan. 2000;33(1):3-14.

Brown et al., The use of quaternary narcotic antagonists in opiate research. Neuropharmacology. Mar. 1985;24(3):181-91.

Bruce et al., Microbial degradation of the morphine alkaloids: identification of morphine as an intermediate in the metabolism of morphine by Pseudomonas putida M10. Arch Microbiol. 1990;154(5):465-70.

Bruley-Des-Varannes et aL,Cholecystokine et ses antagonistes: effets sur la motricite digestive. Gastroenterol Clin Biol. 1991;15:744-57. French.

(56) References Cited

OTHER PUBLICATIONS

Bundgaard et al., (C) Means to Enhance Penetration. (1) Prodrugs as a means to improve the delivery of peptide drugs. J Drug Delivery Rev. 1992;8:1-38.
Burkhart et al., Metkephamid (Tyr-D-Ala-Gly-Phe-N(Me)Met-NH.sub.2), a Potent Opioid Peptide: Receptor Binding and Analgesic Properties. Peptides. 1982;3:869-71.
Caballero-Hernandez et al, Potentiation of rat lymphocyte proliferation by novel non-peptidic synthetic opioids. Int Immunopharmacol. Jul. 2005;5(7-8):1271-8. Epub Apr. 12, 2005.
Cadet et al., Differential expression of the human mu opiate receptor from different primary vascular endothelial cells. Med Sci Monit. Oct. 2004;10(10):BR351-5. Epub Sep. 23, 2004.
Cadet et al., Molecular identification and functional expression of mu 3, a novel alternatively spliced variant of the human mu opiate receptor gene. J Immunol. May 15, 2003;170(10):5118-23.
Calcagnetti et al., Quaternary naltrexone reveals the central mediation of conditional opioid analgesia. Pharmacol Biochem Behav. Jul. 1987;27(3):529-31.
Cao et al., Cardioprotection of interleukin-2 is mediated via kappa-opioid receptors. J Pharmacol Exp Ther. May 2004;309(2):560-7. Epub Jan. 27, 2004.
Cardenas, Eulalia Fernandez Vallin, "Opioides, Mecanismo de Accion," Foro de Investigacion y Tratamiento del Dolor para la Comunidad Medica, Mexico, Revista Dolor Clinica y Terapia, Dol. Clin. Ter. (2003) I(10):21-24.
Cardiac Mechanisms, 2 pgs, retrieved from the internet Aug. 28, 2013, web.sgu.edu.om/med-Lib/MED_CD/E_CDs/anesthesia/site/content/v02/020320r00.htm.
Carmeliet et al., Angiogenesis in cancer and other diseases. Nature. Sep. 14, 2000;407(6801):249-57.
Carr et al., Naltrexone antagonizes the analgesic and immunosuppressive effects of morphine in mice. J Pharmacol Exp Ther. May 1994;269(2):693-8.
Chang et al., An antiabsorptive basis for precipitated withdrawal diarrhea in morphine-dependent rats. J Pharmacol Exp Ther. Feb. 1984;228(2):364-9.
Chang et al., The association between opiates and cytokines in disease. Adv Exp Med Biol. 1998;437:4-6.
Chatterjie et al., Stereospecific synthesis of the 6beta-hydroxy metabolites of naltrexone and naloxone. J Med Chem. May 1975;18(5):490-2. Abstract Only.
Chen et al., Morphine stimulates vascular endothelial growth factor-like signaling in mouse retinal endothelial cells. Curr Neurovasc Res. Aug. 2006;3(3):171-80.
Choi et al., Inhibition of chemokine-induced chemotaxis of monkey leukocytes by mu-opioid receptor agonists. In Vivo. Sep.-Oct. 1999;13(5):389-96.
Choi et al., Opioid antagonists: a review of their role in palliative care, focusing on use in opioid-related constipation. J Pain Symptom Manage. Jul. 2002;24(1):71-90. Review.
Clark, S.J. et al., "Evaluation of opioid-induced antinociceptive effects in anaesthetized and conscious animals" Br. J. Pharmacol. (1988) 95: 275-283.
Collins et al., Peak plasma concentrations after oral morphine: a systematic review. J Pain Symptom Manage. Dec. 1998;16(6):388-402.
Cone et al., The identification and measurement of two new metabolites of naltrexone in human urine. Res Commun Chem Pathol Pharmacol. Jun. 1978;20(3):413-33. Abstract Only.
Cozzolino et al., Acute effects of beta-endorphin on cardiovascular function in patients with mild to moderate chronic heart failure. Am Heart J. Sep. 2004;148(3):E1-7.
Culpepper-Morgan et al., Treatment of opioid-induced constipation with oral naloxone: a pilot study. Clin Pharmacol Ther. Jul. 1992;52(1):90-5. Abstract Only.
D'Amato et al., Studies of three non-peptide cholecystokinin antagonists (devazepide, lorglumide and loxiglumide) in human isolated alimentary muscle and guinea-pig ileum. Br J Pharmacol. Feb. 1991;102(2):391-5.

Dajani et al., Effects of E prostaglandins, diphenoxylate and morphine on intestinal motility in vivo. Eur J Pharmacol. Nov. 1975;34(1):105-13. Abstract Only.
Dajani et al., The pharmacology of SC-27166: a novel antidiarrheal agent. J Pharmacol Exp Ther. Dec. 1977;203(3):512-26. Abstract Only.
Daniel et al., Effects of morphine and other drugs on motility of the terminal ileum. Gastroenterology. Apr. 1959;36(4):510-23.
De Ponti et al., Methylnaltrexone Progenics. Curr Opin Investig Drugs. Apr. 2002;3(4):614-20. Review.
De Schryver et al., New developments in the treatment of irritable bowel syndrome. Scand J Gastroenterol Suppl. 2000;(232):38-42. Review.
Doherty et al., Route-dependent metabolism of morphine in the vascularly perfused rat small intestine preparation. Pharm Res. Mar. 2000;17(3):291-8.
Dragonetti et al., Levallorphan methyl iodide (SR 58002), a potent narcotic antagonist with peripheral selectivity superior to that of other quaternary compounds. Life Sci. 1983;33 Suppl 1:477-80.
Egan et al., Prospective pharmacokinetic and pharmacodynamic validation of propofol's context sensitive T1/2. Anesthesiology. Sep. 1999;91(3A): Abstract A347.
Eisenberg, Effects of naltrexone on plasma corticosterone in opiate-naive rats: a central action. Life Sci. Mar. 19, 1984;34(12):1185-91.
Eisenstein et al., Effect of opioids on oral Salmonella infection and immune function. Adv Exp Med Biol. 2001;493:169-76.
Epstein et al., Naltrexone attenuates acute cigarette smoking behavior. Pharmacol Biochem Behav. Jan. 2004;77(1):29-37.
Fakata, K.L., et al., "Peripheral opioid antagonists, A therapeutic advance for optimizing gastrointestinal opioid tolerability", *Supplement to the Journal of Family Practice* (2007) 56(6): S1-S12.
Farooqui et al., Naloxone acts as an antagonist of estrogen receptor activity in MCF-7 cells. Mol Cancer Ther. Mar. 2006;5(3):611-20.
Farooqui et al., μ opioid receptor stimulates a growth promoting and pro-angiogenic tumor microenvironment. Proc Amer Assoc Cancer Res. 2005;46. AACR Meeting Abstract, Abstract #4650.
Farthing et al., New drugs in the management of the irritable bowel syndrome. Drugs. Jul. 1998;56(1):11-21.
Farup et al., The Symptomatic Effect of Cisapride in Patients with Irritable Bowel Syndrome and Constipation. Scand J Gastronenerol. 1998;33:28-31.
Faura et al., Systematic review of factors affecting the ratios of morphine and its major metabolites. Pain. Jan. 1998;74(1):43-53.
Fecho et al., Assessment of the involvement of central nervous system and peripheral opioid receptors in the immunomodulatory effects of acute morphine treatment in rats. J Pharmacol Exp Ther. Feb. 1996;276(2):626-36.
Fernandez-Tome et al., Interaction between opioid agonists or naloxone and 5-HTP on feeding behavior in food-deprived rats. Pharmacol Biochem Behav. Feb. 1988;29(2):387-92.
Fingl, Chapter 43: Laxatives and cathartics. In Pharmacological Basis of Therapeutics. 1980: 1002-12.
Finn et al., Endocytosis of the mu opioid receptor reduces tolerance and a cellular hallmark of opiate withdrawal. Neuron. Dec. 6, 2001;32(5):829-39.
Flores et al., Mechanisms of morphine-induced immunosuppression: effect of acute morphine administration on lymphocyte trafficking. J Pharmacol Exp Ther. Mar. 1995;272(3):1246-51.
Foss et al., Alvimopan (Entereg.TM.), a novel opioid antagonist, achieves active systemic concentrations. Amer Soc Clin Pharma Ther. 2005:74. Abstract P11-90.
Foss et al., Dose-related antagonism of the emetic effect of morphine by methylnaltrexone in dogs. J Clin Pharmacol. Aug. 1993;33(8):747-51.
Foss et al., Effects of methylnaltrexone on morphine-induced cough suppression in guinea pigs. Life Sci. 1996;59(15):PL235-8.
Foss et al., Enteric-coated methylnaltrexone prevents opioid-induced oral-cecal transit delay in humans. Anesth Analg. 2000;90. Abstract S409.

(56) References Cited

OTHER PUBLICATIONS

Foss et al., Methylnaltrexone does not antagonize the analgesic effect of morphine: a clinical study. 1995 Annual scientific meeting of the American Society of Anesthesiologists. Atlanta, Georgia, Oct. 21-25, 1995. Abstracts. Anesthesiology. Sep. 1995;83(3A Suppl):A361.
Foss et al., Methylnaltrexone reduces morphine-induced postoperative emesis by 30%. Anesth Analg. 1994;78:S119.
Foss et al., Prevention of apomorphine- or cisplatin-induced emesis in the dog by a combination of methylnaltrexone and morphine. Cancer Chemother Pharmacol. 1998;42(4):287-91.
Foss et al., Safety and tolerance of methylnaltrexone in healthy humans: a randomized, placebo-controlled, intravenous, ascending-dose, pharmacokinetic study. J Clin Pharmacol. Jan. 1997;37(1):25-30.
Foss et al., Subcutaneous methylnaltrexone reduces morphine-induced subjective effects in humans. Anesthesiology. 2001;95. Abstract A-817.
Foss et al., The efficacy or oral methylnaltrexone in decreasing the subjective effects of IV morphine. Anesth Analg. 1997;84. Abstract S484.
Foss, A review of the potential role of methylnaltrexone in opioid bowel dysfunction. Am J Surg. Nov. 2001;182(5A Suppl):19S-26S.
France et al., Comparison of naltrexone and quaternary naltrexone after systemic and intracerebroventricular administration in pigeons. Neuropharmacology. Jun. 1987;26(6):541-8.
France et al., Intracerebroventricular drug administration in pigeons. Pharmacol Biochem Behav. Nov. 1985;23(5):731-6.
France et al., Morphine, saline and naltrexone discrimination in morphine-treated pigeons. J Pharm and Exper Ther. 1987;242:195-202.
Fraser et al., Methods for evaluating addiction liability. (A) "Attitude" of opiate addicts toward opiate-like drugs. (B) a short-term "direct" addiction test. J Pharmacol Exp Ther. Sep. 1961;133:371-87. Abstract Only.
Frassdorf et al., Morphine induces late cardioprotection in rat hearts in vivo: the involvement of opioid receptors and nuclear transcription factor kappaB. Anesth Analg. Oct. 2005;101(4):93441.
Frederickson et al., Metkephamid, a Systemically Active Analog of Methionine Enkephalin with Potent Opioid δ-Receptor Activity. Science. 1991;211:603-05.
French et al., Purification and characterization of morphinone reductase from Pseudomonas putida M10. Biochem J. Jul. 1, 1994;301 ( Pt 1):97-103.
Friedman et al., Opioid antagonists in the treatment of opioid-induced constipation and pruritus. Ann Pharmacother. Jan. 2001;35(1):85-91.
Funke et al., A proton and carbon-13 nuclear magnetic resonance study of three quaternary salts of naloxone and oxymorphone. J Chem Soc. 1986:735-8.
Galligan et al., Centrally mediated inhibition of small intestinal transit and motility by morphine in the rat. J Pharmacol Exp Ther. Aug. 1983;226(2):356-61. Abstract Only.
Gan et al., Consensus guidelines for managing postoperative nausea and vomiting. Anesth Analg. Jul. 2003;97(1):62-71. Review.
Gervitz, Targeted approach: methylnaltrexone blocks opioid-induced constipation and other peripheral side effects. Topics in Pain Management. 2005;21(1):6-8.
Giles et al., Quaternary opiate antagonists lower blood pressure and inhibit leucine-enkephalin responses. Eur J Pharmacol. Nov. 25, 1983;95(3-4):247-52.
Gmerek et al., Independent central and peripheral mediation of morphine-induced inhibition of gastrointestinal transit in rats. J Pharmacol Exp Ther. Jan. 1986;236(1):8-13.
Goumon et al., *Ascaris suum*, an intestinal parasite, produces morphine. J Immunol. Jul. 1, 2000;165(1):339-43.
Green and Wuts, "Protective groups in Organic synthesis," Wiley-Interscience, New York (1999) pp. 49-54 and 708-711.
Green, Comparative effects of analgesics on pain threshold, respiratory frequency and gastrointestinal propulsion. Br J Pharmacol Chemother. Mar. 1959;14(1):26-34.
Grigoriev et al., Clinical gastroenterology. Ministry of Health of the Russian Federation. Russian State Medical University. 2001;491-492. Russian.
Gupta et al., Angiogenesis: a curse or cure? Postgrad Med J. Apr. 2005;81(954):236-42.
Gupta et al., Morphine exaggerated retinopathy in transgenic sickle mice. Blood (ASH Annual Meeting Abstracts) 2005, 106: Abstract 209.
Gupta et al., Morphine mimics VEGF in vascular endothelium by promoting pro-angiogenic and survival promoting signaling and angiogenesis. FASEB Journal. 2002;16(4):A207. Abstract #182.12.
Gupta et al., Morphine stimulates angiogenesis by activating proangiogenic and survival-promoting signaling and promotes breast tumor growth. Cancer Res. Aug. 1, 2002;62(15):4491-8.
Gutstein et al., Role of inositol 1,4,5-trisphosphate receptors in regulating apoptotic signaling and heart failure. Heart Vessels. 1997;Suppl 12:53-7.
Guy et al., Chapter 1. Structural models of $Na^{+}$, $Ca^{2+}$, and $K^{+}$ channels. In: Ion Channels and Genetic Diseases. Dawson et al., eds. 1995:1-28.
Hailes et al., Biological synthesis of the analgesic hydromorphone, an intermediate in the metabolism of morphine, by Pseudomonas putida M10. Appl Environ Microbiol. Jul. 1993;59(7):2166-70.
Hanif et al., Hypotensive effect of novel chimeric peptides of met-enkephalin and FMRFa. Regul Pept. Feb. 15, 2005;125(1-3):155-61.
He et al., Improvement of Bowel Dysfunction Caused by Opioid Analgesics: Research Advances on Methylnaltrexone. Chinese Journal of Clinical Rehabilitation. 2002;6(20):3104-05.
Hein et al., Pharmacological analysis of the discriminative stimulus characteristics of ethylketazocine in the rhesus monkey. J Pharmacol Exp Ther. Jul. 1981;218(1):7-15.
Hicks et al., Differential effects of the novel non-peptidic opioid 4-tyrosylamido-6-benzyl-1,2,3,4 tetrahydroquinoline (CGPM-9) on in vitro rat t lymphocyte and macrophage functions. Life Sci. May 4, 2001;68(24):2685-94.
Hirota et al., Loss of a gp130 cardiac muscle cell survival pathway is a critical event in the onset of heart failure during biomechanical stress. Cell. Apr. 16, 1999;97(2):189-98.
Ho et al., Beta-endorphin: peripheral opioid activity of homologues from six species. Int J Pept Protein Res. Apr. 1987;29(4):521-4.
Ho et al., Methylnaltrexone antagonizes opioid-mediated enhancement of HIV infection of human blood mononuclear phagocytes. J Pharmacol Exp Ther. Dec. 2003;307(3):1158-62. Epub Oct. 14, 2003.
Ho et al., Suppression of immunological functions in morphine addicted mice. NIDA Res Monogr. 1986;75:599-602.
Hoffmann et al., [Calcium in the prevention of stress ulcer in the rat] Langenbecks Arch Chir. 1976;Suppl:228-32. German.
Hofmann et al., Hypocalcemia during restraint stress in rats. Indication that gastric ulcer prophylaxis by exogenous calcium interferes with calcitonin release. Res Exp Med (Berl). May 30, 1979;175(2):159-68.
Hou et al., A mu-receptor opioid agonist induces AP-1 and NF-kappa B transcription factor activity in primary cultures of rat cortical neurons. Neurosci Lett. Jul. 19, 1996;212(3):159-62.
Howd et al., Naloxone and intestinal motility. Experientia. Oct. 15, 1978;34(10):1310-1.
Hussain et al., Improvement of the oral bioavailability of naltrexone in dogs: a prodrug approach. J Pharm Sci. May 1987;76(5):356-8.
Hussain et al., Naltrexone-3-salicylate (a prodrug of naltrexone): synthesis and pharmacokinetics in dogs. Pharm Res. Feb. 1988;5(2):113-5.
Hutchinson et al., Assessment in the guinea-pig ileum and mouse vas deferens of benzomorphans which have strong antinociceptive activity but do not substitute for morphine in the dependent monkey. Br J Pharmacol. Dec. 1975;55(4):541-6.
Hutchinson et al., Scintigraphic measurement of ileocaecal transit in irritable bowel syndrome and chronic idiopathic constipation. Gut. Apr. 1995;36(4):585-9.

(56) References Cited

OTHER PUBLICATIONS

International Preliminary Report on Patentability for PCT/US2006/020233 mailed Dec. 13, 2007.
International Search Report and Written Opinion for PCT/US2006/020233 mailed Nov. 24, 2006.
Iorio et al., Diastereoisomeric Quaternary Morphinium Salts: Synthesis, Stereochemistry and Analgesic Properties. European Journal of Medicinal Chemistry. 1984;19(1):11-16.
Iorio et al., Narcotic agonist/antagonist properties of quaternary diastereoisomers derived from oxymorphone and naloxone. Eur J Med Chem. 1984;19(4):301-3.
Jalowiec et al., Suppression of juvenile social behavior requires antagonism of central opioid systems. Pharmacol Biochem Behav. Jul. 1989;33(3):697-700.
Jankovic et al., Quaternary naltrexone: its immunomodulatory activity and interaction with brain delta and kappa opioid receptors. Immunopharmacology. Sep.-Oct. 1994;28(2):105-12.
Jasinski, Assessment of the Abuse Potentiality of Morphinelike Drugs (Methods Used in Man). Drug Addiction J. 1997:197-258.
Jasinski, Tolerance and Dependence to opiates. Acta Anaesthesiol Scand. Jan. 1997;41(1 Pt 2):184-6.
Jenab et al., Ethanol and naloxone differentially upregulate delta opioid receptor gene expression in neuroblastoma hybrid (NG108-15) cells. Brain Res Mol Brain Res. Nov. 1994;27(1):95-102.
Johnson et al., Stability of tacrolimus with morphine sulfate, hydromorphone hydrochloride, and ceftazidime during simulated intravenous coadministration. Am J Health Syst Pharm. Jan. 15, 1999;56(2):164-9.
Kakeji et al., Preclinical studies of the combination of angiogenic inhibitors with cytotoxic agents. Invest New Drugs. 1997;15(1):39-48.
Kasamatsu et al., Attenuation of aortic baroreflex responses by microinjections of endomorphin-2 into the rostral ventrolateral medullary pressor area of the rat. Am J Physiol Regul Integr Comp Physiol. Jul. 2005;289(1):R59-67. Epub Feb. 17, 2005.
Kaufman et al., Role of opiate receptors in the regulation of colonic transit. Gastroenterology. Jun. 1998;94(6):1351-6.
Kehlet et al., Review of postoperative ileus. Am J Surg. Nov. 2001;182(5A Suppl):3S-10S. Review.
Keith et al., Failure of naloxone to prevent the emetic activity of apomorphine in dogs. J Vet Pharmacol Ther. Dec. 1981;4(4):315-6.
Kim et al., Assay for methylnaltrexone in rat brain regions and serum by high-performance liquid chromatography with coulometric electrochemical detection. Chromatographia. Oct. 1989;28(7-8):359-63.
King et al., Hypothalamic-pituitary-adrenocortical (HPA) axis response and biotransformation of oral naltrexone: preliminary examination of relationship to family history of alcoholism. Neuropsychopharmacology. Jun. 2002;26(6):778-88.
Kinsman et al., Effect of naloxone on feedback regulation of small bowel transit by fat. Gastroenterology. Aug. 1984;87(2):335-7.
Knowles et al., Slow transit constipation: a model of human gut dysmotility. Review of possible aetiologies. Neurogastroenterol Motil. Apr. 2000;12(2):181-96.
Koblish et al., Behavioral profile of ADL Aug. 2698, a novel GI-restricted .mu. opioid receptor antagonist. Society for Neuroscience Abstracts. 2001;27(2):2407. Abstract Only.
Kobylecki et al., N-Methylnalorphine: definition of N-allyl conformation for antagonism at the opiate receptor. J Med Chem. Nov. 1982;25(11):1278-80.
Koch et al., Inhibitory neuropeptides and intrinsic inhibitory innervation of descending human colon. Dig Dis Sci. Jun. 1991;36(6):712-8. Abstract Only.
Koczka, et al., Selective Quaternization of Compounds with Morphine Skeleton. Acta Chimica Academica Scien Hung. 1967;51(4):393-02.
Kodani et al., Delta-opioid receptor-induced late preconditioning is mediated by cyclooxygenase-2 in conscious rabbits. Am J Physiol Heart Circ Physiol. Nov. 2002;283(5):H1943-57.
Koob et al., Effects of opiate antagonists and their quaternary derivatives on heroin self-administration in the rat. J Pharmacol Exp Ther. May 1984;229(2):481-6.
Kosten et al., Naltrexone and morphine alter the discrimination and plasma levels of ethanol. Behav Pharmacol. Feb. 1999;10(1):1-13.
Kostic, CAS Abstract Document No. 127: 13345, 1997.
Kotake et al., Variations in demethylation of N-methylnaltrexone in mice, rats, dogs, and humans. Xenobiotica. Nov. 1989;19(11):1247-54.
Kratzel et al., An Efficient Synthesis of 14-Halogenomethyl-Substituted C-Normorphinans. Heterocycles. 1987;26(10):2703-10.
Kratzel et al., Synthesis of 5a,11b-Propanonaphtho[1,2-e][1,2]oxazepines as Potential Opioid Analgesics. J Chem Soc Perkin 1. 1994;11:1541-43.
Kromer et al., Endogenous opioids, the enteric nervous system and gut motility. Dig Dis. 1990;8(6):361-73.
Kromer et al., The current status of opioid research on gastrointestinal motility. Life Sci. 1989;44(9):579-89.
Law et al., Agonist activation of delta-opioid receptor but not mu-opioid receptor potentiates fetal calf serum or tyrosine kinase receptor-mediated cell proliferation in a cell-line-specific manner. Mol Pharmacol. Jan. 1997;51(1):152-60.
Law et al., Properties of delta opioid receptor in neuroblastoma NS20Y: receptor activation and neuroblastoma proliferation. J Pharmacol Exp Ther. Jan. 1995;272(1):322-32.
Law et al., Regulation of opioid receptor activities. J Pharmacol Exp Ther. May 1999;289(2):607-24.
Lazar et al., Synthesis and biological activity of the phosphate and sulfate esters of naloxone and naltrexone. Eur J Med Chem. 1994;29:45-53.
Leander, A kappa opioid effect: increased urination in the rat. J Pharmacol Exp Ther. Jan. 1983;224(1):89-94.
Li et al., Methadone enhances human immunodeficiency virus infection of human immune cells. J Infect Dis. Jan. 1, 2002;185(1):118-22. Epub Dec. 14, 2001.
Lim at al, Morphine preconditions Purkinje cells against cell death under in vitro simulated ischemia-reperfusion conditions. Anesthesiology. Mar. 2004;100(3):562-8.
Linn et al., Peripherally restricted .mu.-opioid receptor antagonists: a review. Tech Reg Anesth Pain Manag. Jul. 2007;11(1):27-32.
Little, et al., ADL 8-2698, a GI restricted opioid antagonist, blocks the antisecretory and colorectal transit effects of morphine and loperamide. Society for Neuroscience Abstracts. 2001;27(2):2407. Abstract Only.
Livingston et al., Postoperative ileus. Dig Dis Sci. Jan. 1990;35(1):121-32.
Lopez et al., Demonstration of long-lasting blockade of experimental ileus in rats by an opioid k-agonist. Gastroenterology. 1995;108(4):Abstract A640.
Lydon at al., Intravenous methylnaltrexone attenuates intrathecal morphine induced delayed gastric emptying in rats. ESA Free Paper Prize Competition. Eur J Anaesthesiol. Apr. 2001;18 Suppl 21:92. Abstract A-327.
Lysle et al., Evidence for the involvement of the caudal region of the periaqueductal gray in a subset of morphine-induced alterations of immune status. J Pharmacol Exp Ther. Jun. 1996;277(3):1533-40.
Lysle et al., Modulation of immune status by a conditioned aversive stimulus: evidence for the involvement of endogenous opioids. Brain Behav Immun. Jun. 1992;6(2):179-88.
Machelska et al., Selectins and integrins but not platelet-endothelial cell adhesion molecule-1 regulate opioid inhibition of inflammatory pain. Br J Pharmacol. Jun. 2004;142(4):772-80. Epub May 24, 2004.
Mack, Paralytic ileus: response to naloxone. Br J Surg. Oct. 1989;76(10):1101.
Magazine et al., Morphine-induced conformational changes in human monocytes, granulocytes, and endothelial cells and in invertebrate immunocytes and microglia are mediated by nitric oxide. J Immunol. Jun. 15, 1996;156(12):4845-50.
Magnan et al., The binding spectrum of narcotic analgesic drugs with different agonist and antagonist properties. Naunyn Schmiedebergs Arch Pharmacol. Jun. 1982;319(3):197-205.

(56) References Cited

OTHER PUBLICATIONS

Maguire et al., Pharmacological profiles of fentanyl analogs at mu, delta and kappa opiate receptors. Eur J Pharmacol. Mar. 24, 1992;213(2):219-25. Abstract Only.
Malspeis et al., Metabolic Reduction of Naltrexone I. Synthesis, Separation and Characterization of Naloxone and Maltrexone Reduction Products and Qualitative Assay of Urine and Bile Following Adminstration of Naltrexone, .alpha.-naltrexol, or.beta.-naltrexol. Chem Pathol Pharmacol. 1975;12(1):43-65.
Manara et al., Inhibition of gastrointestinal transit by morphine in rats results primarily from direct drug action on gut opioid sites. J Pharmacol Exp Ther. Jun. 1986;237(3):945-9. Abstract Only.
Manara et al., Peripheral selectivity of quaternary narcotic antagonists: relative ability to prevent gastrointestinal transit inhibition and antinociception in morphinized rats. Adv. Endog. Exog. Opioids, Poroc. Int. Narc. Res. Conf., 12th (1981):402-4.
Manara et al., The central and peripheral influences of opioids on gastrointestinal propulsion. Annu Rev Pharmacol Toxicol. 1985;25:249-73.
Mancev et al., The immunomodulating effects of specific opioid receptor antagonists after their intracerebroventricular application. Intl J Thymol. 1999;7(12-13):589-95.
Marmor et al., Coronary artery disease and opioid use. Am J Cardiol. May 15, 2004;93(10):1295-7.
McBride et al., Delta2 opioid receptor agonist facilitates mean arterial pressure recovery after hemorrhage in conscious rats. Shock. Mar. 2005;23(3):264-8.
McCance-Katz et al., Interactions between buprenorphine and antiretrovirals. II. The protease inhibitors nelfinavir, lopinavir/ritonavir, and ritonavir. Clin Infect Dis. Dec. 15, 2006;43 Suppl 4:S235-46.
McCarthy et al., Opioids, opioid receptors, and the immune response. Drug Alcohol Depend. Apr. 1, 2001 ;62(2):111-23.
McCarthy et al., Preliminary studies on the use of plasma .beta.-endorphin in horses as an indicator of stress and pain. J Equine Vet Sci. 1993;13(4):216-9.
McQuay et al., Opioid problems and morphine metabolism and excretion. 24 pages, retrieved from the internet Feb. 8, 2010, medicine.ox.ac.uk/bandolier/booth/painpag/wisdom/c14.html.
McQuay, Opioid use in chronic pain. Acta Anaesthesiol Scand. Jan. 1997;41(1 Pt 2):175-83.
Mellon et al., Evidence for central opioid receptors in the immunomodulatory effects of morphine: review of potential mechanism(s) of action. J Neuroimmunol. Mar. 15, 1998;83(1-2):19-28.
Melzig et al., Stimulation of endothelial angiotensin-converting enzyme by morphine via non-opioid receptor mediated processes. Pharmazie. Sep. 1998;53(9):634-7.
Mickley et al., Quaternary naltrexone reverses morphine-induced behaviors. Physiol Behav. Aug. 1985;35(2):249-53.
Miedema et al., Methods for decreasing postoperative gut dysmotility. Lancet Oncol. Jun. 2003;4(6):365-72.
Misra et al., Intravenous kinetics and metabolism of [15,16-3H]naltrexonium methiodide in the rat. J Pharm Pharmacol. Mar. 1987;39(3):225-7.
Miyagi et al., Morphine induces gene expression of CCR5 in human CEMx174 lymphocytes. J Biol Chem. Oct. 6, 2000;275(40):31305-10.
Moerman et al., Evaluation of methylnaltrexone for the reduction of postoperative vomiting and nausea incidences. Acta Anaesthesiol Belg. 1995;46(3-4):127-32.
Moss et al., Methylnaltrexone prevents morphine-induced CCR5 receptor expression. Anesthesiology. 2003;99. Abstract A-961.
Moss et al., Opioid-induced changes in pulmonary barrier integrity may explain heroid-induced pulmonary edema. American Society of Anesthesiologists presentation, Oct. 17, 2007 in San Francisco, CA. Abstract A1980.
Moss et al., Pain relief without side effects: peripheral opiate antagonists. 33.sup.rd ASA Refresher Courses in Anesthesiology, Philadelphia, Lippincott Williams Wilkins, Schwartz, A.J. editor. 2006;33:175-86.
Moss, et al., Selective postoperative inhibition of gastrointestinal opioid receptors. N. Engl. J. Med. 2002;346(6):455.
Mucha, Is the motivational effect of opiate withdrawal reflected by common somatic indices of precipitated withdrawal? A place conditioning study in the rat. Brain Res. Aug. 25, 1987;418(2):214-20.
Mucha, Taste aversion involving central opioid antagonism is potentiated in morphine-dependent rats. Life Sci. 1989;45(8):671-8.
Murphy et al., Opioid antagonist modulation of ischaemia-induced ventricular arrhythmias: a peripheral mechanism. J Cardiovasc Pharmacol. Jan. 1999;33(1):122-5.
Murphy et al., Opioid-induced delay in gastric emptying: a peripheral mechanism in humans. Anesthesiology. Oct. 1997;87(4):765-70.
Murphy et al., Pharmacokinetic profile of epidurally administered methylnaltrexone, a novel peripheral opioid antagonist in a rabbit model. Br J Anaesth. Jan. 2001;86(1):120-2.
Murphy et al., Pharmaconkinetic of epidural administered methylnaltrexone a novel peripheral opioid anatagonist. American Society of Anesthesiologists, 1999 annual meeting. Dallas, Texas, USA. Oct. 9-13, 1999. Anesthesiology. Sep. 1999;91(3ASuppl):A349.
Nair et al., Morphine Modulates the Expression of Chemokines and their Receptors by Peripheral Blood Mononuclear Cells (PBMC) from Normal Donors. J Allergy Clin Immunol. 1998:101(1):557. Abstract 244.
Naranjo et al., Evidence for a central but not adrenal, opioid mediation in hypertension induced by brief isolation in the rat. Life Sci. May 26, 1986;38(21):1923-30.
Nelson et al., Involvement of central mu- but not delta- or kappa-opioid receptors in immunomodulation. Brain Behav Immun. Sep. 2000;14(3):170-84.
Nelson, Morphine modulation of the contact hypersensitivity response: A pharmacological and immunological characterization. University of North Carolina at Chapel Hill. Dissertation Abstracts International. 2001;62/03-B:1635. 94 pages. AbstractOnly.
Nemeth-Lefkowitz et al., Hematological and Immunological Effects of Methadone Administration in Mice. Research Communication in Substances of Abuse. 1980;1(2):177-83.
Neumann et al., Plasma morphine concentrations during chronic oral administration in patients with cancer pain. Pain. Jul. 1982;13(3):247-52.
Nielsen et al., Glycolamide Esters as Biolabile Prodrugs of Carboxylic Acid Agents: Synthesis, Stability, Biocenversion, and Physicochemical Properties. J Pharma Sci. 1988;77:285-98.
Niemegeers et al., Difenoxine (R 15403), the active metabolite of diphenoxylate (R 1132). 2. Difneozine, a potent, orally active and safe antidiarrheal agent in rats. Arzneimittelforschung. Mar. 1972;22(3):516-8.
Notice of Allowance mailed Oct. 19, 2009 for U.S. Appl. No. 11/441,395.
Novick et al., Natural killer cell activity and lymphocyte subsets in parenteral heroin abusers and long-term methadone maintenance patients. J Pharmacol Exp Ther. Aug. 1989;250(2):606-10.
O'Keefe et al., Bowel Disorders Impair Functional Status and Quality of Life in the Elderly: A Population-Based Study. J Gerontol. 1995;50:184-89.
Odio et al., Central but not peripheral opiate receptor blockade prolonged pituitary-adrenal responses to stress. Pharmacol Biochem Behav. Apr. 1990;35(4):963-9.
Osinski et al., Determination of methylnaltrexone in clinical samples by solid-phase extraction and high-performance liquid chromatography for a pharmacokinetics study. J Chromatogr B Analyt Technol Biomed Life Sci. Nov. 25, 2002;780(2):251-9.
Papapetropoulos et al., Nitric oxide synthase inhibitors attenuate transforming-growth-factor-beta 1-stimulated capillary organization in vitro. Am J Pathol. May 1997;150(5):1835-44.
Pappagallo, Incidence, prevalence, and management of opioid bowel dysfunction. Am J Surg. Nov. 2001;182(5A Suppl):11S-18S.
Pasi et al., Angiogenesis: modulation with opioids. Gen Pharmacol. 1991;22(6):1077-9.
Patel et al., COX-2 and iNOS in opioid-induced delayed cardioprotection in the intact rat. Life Sci. May 28, 2004;75(2):129-40.

(56) References Cited

OTHER PUBLICATIONS

Paulson et al., Alvimopan: an oral, peripherally acting, mu-opioid receptor antagonist for the treatment of opioid-induced bowel dysfunction—a 21-day treatment-randomized clinical trial. J Pain. Mar. 2005;6(3):184-92.
Peart et al., Opioid-induced preconditioning: recent advances and future perspectives. Vascul Pharmacol. Apr.-May 2005;42(5-6):211-8. Epub Mar. 17, 2005.
Peeters et al., The motilin antagonist ANQ-11125 blocks motilide-induced contractions in vitro in the rabbit. Biochem Biophys Res Commun. Jan. 28, 1994;198(2):411-6. Abstract Only.
Peterson et al., Morphine promotes the growth of HIV-1 in human peripheral blood mononuclear cell cocultures. AIDS. Sep. 1990;4(9):869-73.
Pham et al., Drugs of Abuse: Chemistry, Pharmacology, Immunology and Aids; National Institute of Drug Research 96: Monograph Series. U.S. Department of Health and Human Services; 1990. 243 pages.
Polak et al., Enkephalin-like immunoreactivity in the human gastrointestinal tract. Lancet. May 7, 1977;1(8019):972-4.
Polakiewicz et al., mu-Opioid receptor activates signaling pathways implicated in cell survival and translational control. J Biot Chem. Sep. 4, 1998;273(36):23534-41.
Poonawala et al., Opioids heal ischemic wounds in the rat. Wound Repair Regen. Mar.-Apr. 2005;13(2):165-74.
Porreca, F. et al., "Nausea and vomiting side effects with opioid analgesics during treatment of chronic pain: Mechanisms, implications, and management options" *Pain Medicine* (2009) 10(4): 654-662.
Powell et al., Paradoxical effects of the opioid antagonist naltrexone on morphine analgesia, tolerance, and reward in rats. J Pharmacol Exp Ther. Feb. 2002;300(2):588-96.
Pugsley et al., Cardiovascular actions of the kappa-agonist, U-50,488H, in the absence and presence of opioid receptor blockade. Br J Pharmacol. Mar. 1992;105(3):521-6.
Quang-Contagrel et al., Long-term methadone treatment: effect on CD4+ lymphocyte counts and HIV-1 plasma RNA level in patients with HIV infection. Eur J Pain. 2001;5(4):415-20.
Quock et al., Narcotic antagonist potentiation of apomorphine drug effect: a stereospecific, centrally mediated drug action. Prog Neuropsychopharmacol Biol Psychiatry. 1985;9(3):239-43.
Quock et al., Narcotic antagonist-induced hypotension in the spontaneously hypertensive rat. Life Sci. Sep. 2, 1985;37(9):819-26.
Quock, et al, Microwave facilitation of methylnaltrexone antagonism of morphine-induced analgesia in mice. J Bioelect. 1986;5(1):35-46.
Radulovic et al., Opioid receptor-mediated suppression of humoral immune response in vivo and in vitro: involvement of kappa opioid receptors. J Neuroimmunol. Mar. 1995;57(1-2):55-62.
Ramabadran, Effects of N-methylnaloxone and N-methylnaltrexone on nociception and precipitated abstinence in mice. Life Sci. Sep. 20-27, 1982;31(12-13):1253-6.
Read et al., Interpretation of the breath hydrogen profile obtained after ingesting a solid meal containing unabsorbable carbohydrate. Gut. Aug. 1985;26(8):834-42.
Reisine et al., Opioid Analgesics and Antagonists. In: Goodman & Goodman's The Pharmacological Basis of Therapeutics. 9.sup.th Ed. 1996:521-55.
Resnick et al., Delayed gastric emptying and postoperative ileus after nongastric abdominal surgery: part I. Am J Gastroenterol. May 1997;92(5):751-62.
Resnick et al., Delayed gastric emptying and postoperative ileus after nongastric abdominal surgery: part II. Am J Gastroenterol. Jun. 1997;92(6):934-40.
Risdahl et al., Opiates and infection. J Neuroimmunol. Mar. 15, 1998;83(1-2):4-18.
Riviere et al., Fedotozine reverses ileus induced by surgery or peritonitis: action at peripheral kappa-opioid receptors. Gastroenterology. Mar. 1993;104(3):724-31.

Robinson et al., Oral naloxone in opioid-associated constipation. Lancet. Aug. 31, 1991;338(8766):581-2.
Roger et al., Colonic motor responses in the pony: relevance of colonic stimulation by opiate antagonists. Am J Vet Res. Jan. 1985;46(1):31-5.
Roy et al., Morphine modulates NF kappa B activation in macrophages. Biochem Biophys Res Commun. Apr. 17, 1998;245(2):392-6.
Russell et al., Antagonism of gut, but not central effects of morphine with quaternary narcotic antagonists. Eur J Pharmacol. Mar. 12, 1982;78(3):255-61.
Sachs et al., Peripheral analgesic blockade of hypernociception: activation of arginine/NO/cGMP/protein kinase G/ATP-sensitive K+ channel pathway. Proc Natl Acad Sci U S A. Mar. 9, 2004;101(10):3680-5. Epub Feb. 27, 2004.
Saffran et al., A new approach to the oral administration of insulin and other peptide drugs. Science. Sep. 5, 1986;233(4768):1081-4. Abstract Only.
Sakurada et al., Differential antagonism of endomorphin-1 and endomorphin-2 supraspinal anti nociception by naloxonazine and 3-methylnaltrexone. Peptides. May 2002;23(5):895-901.
Sandner-Keisling et al., Pharmacology of opioid inhibition to noxious uterine cervical distension. Anesthesiology. Oct. 2002;97(4):966-71.
Sawhney et al., Bioerodible Hydrogels Based on Photopolymerized Poly(ethylene glycol)-co-poly(.alpha.-hydroxy acid) Diacrylate Macromers. Macromolecules. 1993;26:581-87.
Schaefer et al., Effects of opioid antagonists and their quaternary derivatives on locomotor activity and fixed ratio responding for brain self-stimulation in rats. Pharmacol Biochem Behav. Nov. 1985;23(5):797-802.
Schang et al., Beneficial effects of naloxone in a patient with intestinal pseudoobstruction. Am J Gastroenterol. Jun. 1985;80(6):407-11.
Schang et al., How does morphine work on colonic motility? An electromyographic study in the human left and sigmoid colon. Life Sci. Feb. 24, 1986;38(8):671-6.
Schiller et al., Studies of the mechanism of the antidiarrheal effect of codeine. J Clin Invest. Nov. 1982;70(5):999-1008.
Schmidhammer, et al., Synthesis and biological evaluation of 14-alkoxymorphinans. Part 10[1]. 14-O-methyl derivatives of 5-methylnalthrexone and 5-methylnaloxone. Helv Chim Acta. 1994;77(6):1585-9.
Schmidhammer, et al., Synthesis and biological evaluation of 14-alkoxymorphinans. Part 9[1]. 14-O-ethyl-5-methylnaltrexone, an opioid antagonist with unusual selectivity. Helv Chim Acta. 1993:(1):476-80.
Schmidt et al., Alvimopan (ADL 8-2698) is a novel peripheral opioid antagonist. Am J Surg. Nov. 2001;182(5A Suppl):27S-38S.
Scholz, Managing constipation that's opioid-induced. 2000; 63(6):103.
Schreier et al., Central regulation of intestinal function: morphine withdrawal diarrhea. Proc West Pharmacol Soc. 1982;25:151-4.
Schubert-Zsilavecz et al., [Das reizdarmsyndrom] The irritable bowel syndrome. Deutsche apotheker zeitung. Aug. 22, 2002; 142(34): 40-9. German.
Schug et al., A long-term survey of morphine in cancer pain patients. J Pain Symptom Manage. Jul. 1992;7(5):259-66. Abstract Only.
Schuller et al., M6G, but not morphine, inhibits GI transit in mu opioid receptor deficient mice. Society of Neuroscience Abstracts. 1998;24:524. Abstract 210.7.
Sezen et al., Renal excretory responses produced by the delta opioid agonist, BW373U86, in conscious rats. J Pharmacol Exp Ther. Oct. 1998;287(1):238-45.
Shahbazian et al., Involvement of mu- and kappa-, but not delta-, opioid receptors in the peristaltic motor depression caused by endogenous and exogenous opioids in the guinea-pig intestine. Br J Pharmacol. Feb. 2002;135(3):741-50.
Shavit et al., Effects of a single administration of morphine or footshock stress on natural killer cell cytotoxicity. Brain Behav Immun. Dec. 1987;1(4):318-28.

(56) References Cited

OTHER PUBLICATIONS

Shi et al., Cardioprotective effects of morphine on rat heart suffering from ischemia and reperfusion. Chin Med J (Engl). Jul. 2003;116(7):1059-62.
Simonin et al., Kappa-Opioid receptor in humans: cDNA and genomic cloning, chromosomal assignment, functional expression, pharmacology, and expression pattern in the central nervous system.. Proc Natl Acad Sci U S A. Jul. 18, 1995;92(15):7006-10.
Simonin et al., The human delta-opioid receptor: genomic organization, cDNA cloning, functional expression, and distribution in human brain. Mol Pharmacol. Dec. 1994;46(6):1015-21. Abstract Only.
Soldani et al., Central and peripheral involvement of mu receptors in gastric secretory effects of opioids in the dog. Eur J Pharmacol. Nov. 19, 1985;117(3):295-301.
Solvason et al., Naltrexone blocks the expression of the conditioned elevation of natural killer cell activity in BALB/c mice. Brain Behav Immun. Sep. 1989;3(3):247-62.
Stanski et al., Kinetics of intravenous and intramuscular morphine. Clin Pharmacol Ther. Jul. 1978;24(1):52-9.
Steele et al., HIV-1 Infection and Opioid Administration Modulate the Expression of Chemokine Receptors. Drug and Alcohol Dependence. 2000:60(Supp 1):S212. Abstract 599.
Stefano et al., Delta2 opioid receptor subtype on human vascular endothelium uncouples morphine stimulated nitric oxide release. Int J Cardiol. Apr. 30, 1998;64 Suppl 1:S43-51.
Stefano et al., Long-term exposure of human blood vessels to HIV gp120, morphine, and anandamide increases endothelial adhesion of monocytes: uncoupling of nitric oxide release. J Cardiovasc Pharmacol. Jun. 1998;31(6):862-8.
Stefano et al., Morphine enhances nitric oxide release in the mammalian gastrointestinal tract via the micro(3) opiate receptor subtype: a hormonal role for endogenous morphine. J Physiol Pharmacol. Mar. 2004;55(1 Pt 2):279-88.
Stefano et al., Presence of the mu3 opiate receptor in endothelial cells. Coupling to nitric oxide production and vasodilation. J Biol Chem. Dec. 22, 1995;270(51):30290-3.
Steinbrook et al., An opioid antagonist for postoperative ileus. N. Engl J Med. Sep. 27, 2001 ;345(13):988-9.
Stephenson et al., Methylnaltrexone reverses opioid-induced constipation. Lancet Oncol. Apr. 2002;3(4):202.
Sternini et al., The opioid system in the gastrointestinal tract. Neurogastroenterol Motil. Oct. 2004;16 Suppl 2:3-16.
Stewart et al., Central and peripheral actions of morphine on intestinal transit. J Pharmacol Exp Ther. Jun. 1978;205(3):547-55.
Stiene-Martin et al., Regional, developmental, and cell cycle-dependent differences in mu, delta, and kappa-opioid receptor expression among cultured mouse astrocytes. Glia. Mar. 1998;22(3):249-59.
Suzuki et al., Morphine suppresses lymphocyte apoptosis by blocking p53-mediated death signaling. Biochem Biophys Res Commun. Sep. 5, 2003;308(4):802-8.
Swan, et al., NIDA plays key role in studying links between AIDS and drug abuse. AIDS Research, NIDA Notes. 1995; 10(3):1-4.
Sykes, Chapter 9. Using oral naloxone in management of opioid bowel dysfunction. Handbook of Opioid Bowel Syndrome, New York, Haworth Medical Press, Yuan, C-S, editor. 2005:175-95.
Sykes, Oral naloxone in opioid-associated constipation. Lancet. Jun. 15, 1991;337(8755):1475.
Szabo et al., Interactions of opioid receptors, chemokines, and chemokine receptors. Adv Exp Med Biol. 2001;493:69-74.
Taguchi et al., Selective postoperative inhibition of gastrointestinal opioid receptors. N. Engl J Med. Sep. 27, 2001;345(13):935-40.
Talley et al., Pharmacologic therapy for the irritable bowel syndrome. Am J Gastroenterol. Apr. 2003;98(4):750-8.
Tavani et al., Morphine is most effective on gastrointestinal propulsion in rats by intraperitoneal route: evidence for local action. Life Sci. Dec. 8, 1980;27(23):2211-7.
Tegeder et al., Opioids as modulators of cell death and survival—unraveling mechanisms and revealing new indications. Pharmacol Rev. Sep. 2004;56(3):351-69.
Thomas et al., A phase III double-blind placebo-controlled trial of methylnaltrexone (MNTX) for opioid-induced constipation (OIC) in advanced medical illness (AMI). Abstract No. LBA8003 from the 2005 ASCO Annual Meeting. 3 pages.
Thomas et al., Amelioration of peripheral side effects of opioids: clinical experience with methylnaltrexone (MNTX). Proc World Congr Anesth. 2004:107. Abstract Only.
Thompson et al., Laxatives: clinical pharmacology and rational use. Drugs. Jan. 1980;19(1):49-58.
Thompson et al., Opioid stimulation in the ventral tegmental area facilitates the onset of maternal behavior in rats. Brain Res. Dec. 16, 1996;743(1-2):184-201.
Tomiyasu et al., Analysis of intercostal nerve damage associated with chronic postthoracotomy pain. Anesthesiology. 2001;95. Abstract A-964.
Tryoen-Toth et al., Regulation of kappa-opioid receptor mRNA level by cyclic AMP and growth factors in cultured rat glial cells. Brain Res Mol Brain Res. Mar. 30, 1998;55(1):141-50.
Ukai et al., Suppression of deprivation-induced water intake in the rat by opioid antagonists: central sites of action. Psychopharmacology (Berl). 1987;91(3):279-84.
Uwai et al., Syntheses and receptor-binding studies of derivatives of the opioid antagonist naltrexone. Bioorg Med Chem. Jan. 15, 2004;12(2):417-21.
Valentino et al., Quaternary naltrexone: evidence for the central mediation of discriminative stimulus effects of narcotic agonists and antagonists. J Pharmacol Exp Ther. Jun. 1981 ;217(3):652-9.
Valentino et al., Receptor binding, antagonist, and withdrawal precipitating properties of opiate antagonists. Life Sci. Jun. 20, 1983;32(25):2887-96.
Vallejo et al., Opioid therapy and immunosuppression: a review. Am J Ther. Sep.-Oct. 2004 ;11 (5):354-65.
Vaughan et al., Human antibodies by design. Nat Biotechnol. Jun. 1998;16(6):535-9.
Vermiere et al., Stability and compatibility of morphine. International Journal of Pharmaceutics. 1999;187:17-51.
Waldhoer et al., Opioid receptors. Annu Rev Biochem. 2004;73:953-90.
Walker, et al., Role of central versus peripheral opioid receptors in analgesia induced by repeated administration of opioid antagonists. Psychopharmacology. 1991;104(2):164-6.
Walsh et al., The symptoms of advanced cancer: relationship to age, gender, and performance status in 1,000 patients. Support Care Cancer. May 2000;8(3):175-9. Abstract Only.
Wang et al., A non-peptide substance P antagonist (CP-96,345) inhibits morphine-induced NF-kappa B promoter activation in human NT2-N neurons. J Neurosci Res. Feb. 15, 2004;75(4):544-53.
Wang et al., Determination of tungsten in bulk drug substance and intermediates by ICp-AES and ICP-Ms. J Pharm Biomed Anal. May 1999;19(6):937-43. Abstract Only.
Wang et al., Human mu opiate receptor. cDNA and genomic clones, pharmacologic characterization and chromosomal assignment. FEBS Lett. Jan. 31, 1994;338(2):217-22. Abstract Only.
Wang et al., Mobilization of calcium from intracellular stores as one of the mechanisms underlying the antiopioid effect of cholecystokinin octapeptide. Peptides. Sep.-Oct. 1992;13(5):947-51.
Wang et al., Morphine negatively regulates interferon-gamma promoter activity in activated murine T cells through two distinct cyclic AMP-dependent pathways. J Biol Chem. Sep. 26, 2003;278(39):37622-31. Epub Jul. 3, 2003.
Wang et al., The immunosuppressive effects of chronic morphine treatment are partially dependent on corticosterone and mediated by the mu-opioid receptor. J Leukoc Biol. May 2002 ;71 (5):782-90.
Warren et al., Effects of quaternary naltrexone and chlordiazepoxide in squirrel monkeys with enhanced sensitivity to the behavioral effects of naltrexone. J Pharmacol Exp Ther. Nov. 1985;235(2):412-7.

(56) References Cited

OTHER PUBLICATIONS

Wei et al., Effects of Subcutaneous Methylnaltrexone on Morphine-Induced Gut Motility Changes: A Clinical Trial. Abstracts of the 2002 Annual Meeting of the American Society for Clinical Pharmacology and Therapeutics. Atlanta, Georgia, USA. Mar. 24-27, 2002. Clin Pharmacol Ther. Feb. 2002;71(2):P11. Abstract MPI-26.
Wei et al., Opioid-induced immunosuppression: is it centrally mediated or peripherally mediated? Biochem Pharmacol. Jun. 1, 2003;65(11):1761-6.
Wei et al., Pharmacokinetics of subcutaneous methylnaltrexone: different route administration comparison. 2001. ASA Annual Meeting Abstracts. Oct. 14-18, 2001. Chicago, IL. Abstract A-962.
Wentland et al., Synthesis and opioid receptor binding properties of a highly potent 4-hydroxy analogue of naltrexone. Bioorg Med Chem Lett. Apr. 15, 2005;15(8):2107-10.
Whistler et al., Functional dissociation of mu opioid receptor signaling and endocytosis: implications for the biology of opiate tolerance and addiction. Neuron. Aug. 1999;23(4):737-46.
Willett et al., Direct evidence that the VEGF-specific antibody bevacizumab has antivascular effects in human rectal cancer. Nat Med. Feb. 2004;10(2):145-7. Epub Jan. 25, 2004.
Willette, et al., Evidence for anticholinergic effects of naltrexone methylbromide. Res Comm Subst Abuse. 1983;4(4):325-37.
Wilmore et al., Can we minimize the effects of opioids on the bowel and still achieve adequate pain control? Am J Surg. Nov. 2001;182(5A Suppl):1S-2S.
Wingo et al., Cancer statistics, 1995. CA Cancer J Clin. Jan.-Feb. 1995;45(1):8-30.
Witkin et al., Pharmacology of 2-amino-indane hydrochloride (Su-8629): a potent non-narcotic analgesic. J Pharmacol Exp Ther. Sep. 1961;133:400-8. Abstract Only.
Wittert et al., Tissue distribution of opioid receptor gene expression in the rat. Biochem Biophys Res Commun. Jan. 26, 1996;218(3):877-81.
Wolff et al., Alvimopan, a novel, peripherally acting mu opioid antagonist: results of a multicenter, randomized, double-blind, placebo-controlled, phase III trial of major abdominal surgery and postoperative ileus. Ann Surg. Oct. 2004;240(4):728-34; discussion 734-5.
Wybran et al., Suggestive evidence for receptors for morphine and methionine-enkephalin on normal human blood T lymphocytes. J Immunol. Sep. 1979;123(3):1068-70.
Yamamoto et al., Inhibition of stress-stimulated colonic propulsion by alpha 2-adrenoceptor antagonists in rats. Neurogastroenterol Motil. Dec. 1998;10(6):523-32. Abstract Only.
Yeh et al., Stability of morphine in aqueous solution. Am J Hosp Pharmacy. 1960;17(2):101-103.
Yoshida et al., Effect of surgical stress on endogenous morphine and cytokine levels in the plasma after laparoscopoic or open cholecystectomy. Surg Endosc. Feb. 2000;14(2):137-40.
Yuan et al., Antagonism of chronic opioid-induce gut effects. Anesth Analg. 2000;90:S1-523. Abstract S479.
Yuan et al., Antagonism of gastrointestinal opioid effects. Reg Anesth Pain Med. Nov.-Dec. 2000;25(6):639-42.
Yuan et al., Clinical status of methylnaltrexone, a new agent to prevent and manage opioid-induced side effects. J Support Oncol. Mar.-Apr. 2004;2(2):111-7; discussion 119-22.
Yuan et al., Dose-related effects of oral acetaminophen on cold-induced pain: a double-blind, randomized, placebo-controlled trial. Clin Pharmacol Ther. Mar. 1998;63(3):379-83.
Yuan et al., Effects of enteric-coated methylnaltrexone in preventing opioid-induced delay in oral-cecal transit time. Clin Pharmacol Ther. Apr. 2000;67(4):398-404.
Yuan et al., Effects of intravenous methylnaltrexone on opioid-induced gut motility and transit time changes in subjects receiving chronic methadone therapy: a pilot study. Pain. Dec. 1999;83(3):631-5.
Yuan et al., Effects of low-dose morphine on gastric emptying in healthy volunteers. J Clin Pharmacol. Nov. 1998;38(11):1017-20.
Yuan et al., Effects of methylnaltrexone on chronic opioid induced gut motility and transit time changes. Br J Anaesth. 1998;81(1):94. Abstract Only.
Yuan et al., Effects of methylnaltrexone on chronic opioid-induced gut motility and transit time changes. University of Leicester—Abstracts from the Eighth International Symposium on Pain, Anaesthesia and Endocrinology. Sep. 18-19, 1997.
Yuan et al., Effects of methylnaltrexone on morphine-induced inhibition of contraction in isolated guinea-pig ileum and human intestine. Eur J Pharmacol. Mar. 24, 1995;276(1-2):107-11.
Yuan et al., Effects of methylnaltrexone on morphine-induced inhibition of contractions in isolated guinea-pig and human intestine. Anesthesiology, Sep. 1995; 83(3A). Abstract A358.
Yuan et al., Effects of subcutaneous methylnaltrexone on morphine-induced peripherally mediated side effects: a double-blind randomized placebo-controlled trial. J Pharmacol Exp Ther. Jan. 2002;300(1):118-23.
Yuan et al., Efficacy of orally administered methylnaltrexone in decreasing subjective effects after intravenous morphine. Drug Alcohol Depend. Oct. 1, 1998;52(2):161-5.
Yuan et al., Gastric effects of methylnaltrexone on mu, kappa, and delta opioid agonists induced brainstem unitary responses. Neuropharmacology. Mar. 1999;38(3):425-32.
Yuan et al., Gastric effects of mu-, delta- and kappa-opioid receptor agonists on brainstem unitary responses in the neonatal rat. Eur J Pharmacol. Oct. 24, 1996;314(1-2):27-32.
Yuan et al., Gut and brain effects of American ginseng root on brainstem neuronal activities in rats. Amer J Chin Med. 1998; 26: 47-55.
Yuan et al., Gut motility and transit changes in patients receiving long-term methadone maintenance. J Clin Pharmacol. Oct. 1998;38(10):931-5.
Yuan et al., Methylnaltrexone (MNTX) for chronic opioid-induced constipation. 2002 ASCO Annual Meeting. Proc Am Soc Clin Oncol. 2002;21:376a. Abstract 1501.
Yuan et al., Methylnaltrexone (MNTX) reverses chronic opioid constipation: a double-blind, randomized, placebo-controlled trial. Anesthesiology. Sep. 1999; 91 (3A). Abstract A973.
Yuan et al., Methylnaltrexone changes gut motility and transit time in chronic methadone-maintained subjects. Anesth Analg. 1999;88: S1-424. Abstract S404.
Yuan et al., Methylnaltrexone effects on morphine-induced inhibition in isolated guinea-pig and human intestine. Clin Pharm & Therapeut. Feb. 1995;57:138. Abstract PI-11.
Yuan et al., Methylnaltrexone for reversal of constipation due to chronic methadone use: a randomized controlled trial. JAMA. Jan. 19, 2000;283(3):367-72.
Yuan et al., Methylnaltrexone prevents morphine-induced delay in oral-cecal transit time without affecting analgesia: a double-blind randomized placebo-controlled trial. Clin Pharmacol Ther. Apr. 1996;59(4):469-75.
Yuan et al., Methylnaltrexone prevents morphine-induced kaolin intake in the rat. Anesthesiology. 2003;99. Abstract A-922.
Yuan et al., Methylnaltrexone reduces oral-cecal transit time in humans. Dig Dis Week Abstr. 2003:A-578. Abstract T1840.
Yuan et al., Methylnaltrexone reverses morphine-induced changes in gastrointestinal motility: a clinical study. Anesthesiology Sep. 1995;83(3A): Abstract A360.
Yuan et al., Methylnaltrexone, a novel peripheral opioid receptor antagonist for the treatment of opioid side effects. Expert Opin Investig Drugs. May 2006;15(5):541-52.
Yuan et al., Methylnaltrexone: investigation of clinical applications. Drug Develop Res. 2000;50(2):133-41.
Yuan et al., Opioid analgesia without gut side effects: effects of methylnaltrexone as a novel peripheral opioid antagonist. Assoc Univ Anesth Abst. 2003: PD2.
Yuan et al., Oral methylnaltrexone for opioid-induced constipation. JAMA. Sep. 20, 2000;284(11):1383-4.
Yuan et al., Oral methylnaltrexone reverses chronic opioid-induced constipation. Anesthesiology. Sep. 2000;93(3A). Abstract A-872.
Yuan et al., Oral methylnaltrexone reverses morphine-induced changes in gastrointestinal motility. Anesthesiology. Sep. 1995;85(3A). Abstract A335.

(56) References Cited

OTHER PUBLICATIONS

Yuan et al., Pain control without side effects: clinical studies on methylnaltrexone as a novel peripheral opioid antagonist. 7.sup.th America-Japan Anesth Congr. Yamanashi, Japan. 2004:41.

Yuan et al., Pharmacokinetics of intravenous vs. oral methylnaltrexone: evidence for direct gut effects. Anesth Analg. 2001;92: S1-363. Abstract S274.

Yuan et al., Safety and tolerance of oral methylnaltrexone in healthy volunteers. Anesth Analg. 1997;84:S1-599. Abstract S574.

Yuan et al., Subcutaneous methylnaltrexone prevents morphine-induced delay in gut transit time: a clinical trial. Anesthesiology. 2001;95. Abstract A-963.

Yuan et al., The safety and efficacy of oral methylnaltrexone in preventing morphine-induced delay in oral-cecal transit time. Clin Pharmacol Ther. Apr. 1997;61(4):467-75.

Yuan et al., Tolerability, gut effects, and pharmacokinetics of methylnaltrexone following repeated intravenous administration in humans. J Clin Pharmacol. May 2005;45(5):538-46.

Zagon et al., Opioid antagonists inhibit the growth of metastatic murine neuroblastoma. Cancer Lett. Nov. 1983; 21(1):89-94.

Zagon et al., Opioid growth factor regulates the cell cycle of human neoplasias. Int J Oncol. Nov. 2000;17(5):1053-61.

Zagon et al., Opioids and differentiation in human cancer cells. Neuropeptides. Oct. 2005;39(5):495-505. Epub Sep. 15, 2005.

Zagon et al., Opioids and the apoptotic pathway in human cancer cells. Neuropeptides. Apr. 2003;37(2):79-88.

Zhang et al., Dynorphin A as a potential endogenous ligand for four members of the opioid receptor gene family. J Pharmacol Exp Ther. Jul. 1998;286(1):136-41.

Zhang et al., Effect of the endogenous kappa opioid agonist dynorphin A(1-17) on cocaine-evoked increases in striatal dopamine levels and cocaine-induced place preference in C57BL/6J mice. Psychopharmacology (Berl). Apr. 2004;172(4):422-9. Epub Jan. 8, 2004.

Zimmerman et al., Discovery of a potent, peripherally selective trans-3,4-dimethyl-4-(3-hydroxyphenyl) piperidine opioide antagonist for the treatment of gastrointestinal motility disorders. J Med Chem. Jul. 22, 1994,37(15):2262-5.

\* cited by examiner

| PEAK NO | RET. TIME (MIN) | AREA (COUNTS) | SEP. CODE | WIDTH 1/2 (SEC) | RESULT 0 |
|---|---|---|---|---|---|
| 1 | 9.298 | 908375 | BB | 7.4 | 55.32 |
| 2 | 9.798 | 733746 | BB | 6.7 | 44.68 |
|  |  | 1642121 |  |  | 100.00 |

SYNTHESIS OF (R)-N-METHYLNALTREXONE

RELATED APPLICATIONS

The present application is a continuation of U.S. patent application Ser. No. 14/218,585, filed Mar. 18, 2014, entitled "SYNTHESIS OF (R)—N-METHYLNALTREXONE," which is a continuation of U.S. patent application Ser. No. 13/670,846, filed Nov. 7, 2012, entitled "SYNTHESIS OF R—N-METHYLNALTREXONE," which is a continuation of U.S. patent application Ser. No. 12/692,083, filed Jan. 22, 2010, entitled "SYNTHESIS OF R—N-METHYLNALTREXONE," now U.S. Pat. No. 8,343,992, issued Jan. 1, 2013, which is a divisional of U.S. patent application Ser. No. 11/441,395, filed May 25, 2006, entitled "SYNTHESIS OF R—N-METHYLNALTREXONE," now U.S. Pat. No. 7,674,904, issued Mar. 9, 2010; which claims benefit under 35 U.S.C. §119(e) of the filing date of U.S. Provisional Application No. 60/684,616, filed on May 25, 2005, entitled "SYNTHESIS OF R—N-METHYLNALTREXONE," the contents of each of which are hereby incorporated by reference in their entirety.

FIELD OF THE INVENTION

This invention relates to stereoselective synthesis of (R)—N-methylnaltrexone (R-MNTX) and intermediates thereof, pharmaceutical preparations comprising R-MNTX or intermediates thereof and methods for their use.

BACKGROUND OF INVENTION

Methylnaltrexone (MNTX) is a quaternary derivative of the pure opioid antagonist, naltrexone. It exists as a salt. Names used for the bromide salt of MNTX in the literature include: Methylnaltrexone bromide; N-Methylnaltrexone bromide; Naltrexone methobromide; Naltrexone methyl bromide; MRZ 2663BR. MNTX was first reported in the mid-70s by Goldberg et al as described in U.S. Pat. No. 4,176,186. It is believed that addition of the methyl group to the ring nitrogen forms a charged compound with greater polarity and less liposolubility than naltrexone. This feature of MNTX prevents it from crossing the blood-brain bather in humans. As a consequence, MNTX exerts its effects in the periphery rather than in the central nervous system with the advantage that it does not counteract the analgesic effects of opioids on the central nervous system.

MNTX is a chiral molecule and the quaternary nitrogen can be in R or S configuration. (See FIG. 1.) It is unknown whether the different stereoisomers of MNTX exhibit different biological and chemical properties. All of the reported functions of MNTX described in the literature indicate that MNTX is a peripheral opioid antagonist. Some of these antagonist functions are described in U.S. Pat. Nos. 4,176, 186, 4,719,215, 4,861,781, 5,102,887, 5,972,954, 6,274,591, 6,559,158, and 6,608,075, and in U.S. patent application Ser. No. 10/163,482 (2003/0022909A1), Ser. No. 10/821,811 (20040266806), Ser. No. 10/821,813 (20040259899) and Ser. No. 10/821,809 (20050004155). These uses include reducing the side-effects of opioids without reducing the analgesic effect of opioids. Such side-effects include nausea, emesis, dysphoria, pruritus, urinary retention, bowel hypomotility, constipation, gastric hypomotility, delayed gastric emptying and immune suppression. The art discloses that MNTX not only reduces the side-effects stemming from opioid analgesic treatment but also reduces the side-effects mediated by endogenous opioids alone or in conjunction with exogenous opioid treatment. Such side-effects include inhibition of gastrointestinal motility, post-operative gastrointestinal dysfunction, idiopathic constipation and other such conditions including, but not limited to, those mentioned above. However, it is unclear from the art whether the MNTX used in these studies was a mixture of R and S stereoisomers or a single stereoisomer.

The art suggests that isolated stereoisomers of a compound sometimes may have contrasting physical and functional properties, although it is unpredictable whether this is the case in any particular circumstance. Dextromethorphan is a cough suppressant, whereas its enantiomer, levomethorphan, is a potent narcotic. R,R-methylphenidate is a drug to treat attention deficit hyperactivity disorder (ADHD), whereas its enantiomer, S,S-methylphenidate is an antidepressant. S-fluoxetine is active against migraine, whereas its enantiomer, R-fluoxetine is used to treat depression. The S enantiomer of citalopram is therapeutically active isomer for treatment of depression. The R enantiomer is inactive. The S enantiomer of omeprazole is more potent for the treatment of heartburn than the R enantiomer.

Bianchetti et al, 1983 *Life Science* 33 (Sup I):415-418 studied three pairs of diastereoisomers of quaternary narcotic antagonist and their parent tertiary amines, levallorphan, nalorphine, and naloxone, to see how the configuration about the chiral nitrogen affected in vitro and in vivo activity. It was found that the activity varied considerably depending on how the quaternary derivatives were prepared. In each series, only the diastereomer obtained by methylation of the N-allyl-substituted tertiary amine (referred to as "N-methyl diastereomer") was potent in displacing $^3$H-naltrexone from rat brain membranes, and acting as a morphine antagonist in the guinea-pig ileum. Conversely, diastereoisomers obtained by reacting N-methyl-substituted tertiary amines with allyl halide (referred to as "N-allyl diastereomers") did not displace 3H-naltrexone and had negligible antagonist activity and slight agonist action in the guinea-pig ileum. In vivo findings were generally consistent with those in vitro. Thus only the "N-methyl" but not the "N-allyl diastereomers" inhibited morphine-induced constipation in rats and behaved as antagonists. The author stated that the prepared materials appeared to be pure by $^1$H and $^{13}$C nuclear magnetic resonance (NMR) analysis, but these methods are not accurate. The author cites a literature reference for the assignment of the R configuration to the "N-methyl diastereomer" of nalorphine. No assignment is proposed for the levallorphan and naloxone diastereomers. It would be adventurous to extrapolate the configuration to these diastereomers (R. J. Kobylecki et al, J. Med. Chem. 25, 1278-1280, 1982).

Goldberg et al.'s U.S. Pat. No. 4,176,186, and more recently Cantrell et al.'s WO 2004/043964 A2 describe a protocol for the synthesis of MNTX. Both describe a synthesis of MNTX by quaternizing a tertiary N-substituted morphinan alkaloid with a methylating agent. Both Goldberg et al. and Cantrell et al. are silent as to the stereoisomer(s) produced by the synthesis. The authors remained cautiously silent about the stereochemistry because the stereochemistry could not be determined based on prior art. The cyclopropylmethyl side-chain in naltrexone is different from the prior art side-chains and may have affected the stereochemical outcome in the synthesis of MNTX, as may other reaction parameters such as temperature and pressure. Based on the method of synthesis described in each, it is unknown whether the MNTX so produced was R, S or a mixture of both.

S-MNTX in pure form, and a method of making pure S-MNTX have not been described in the literature. Researchers would have been unable to definitively characterize and distinguish the stereoisomer(s) obtained by the Goldberg et al. or Cantrell et al. synthesis in the absence of pure S-MNTX as a standard.

SUMMARY OF THE INVENTION

S-MNTX has now been produced in high purity permitting the characterization of its relative retention time in chromatography versus that of R-MNTX. The pure S-MNTX has been found to have activity different from the activity of MNTX reported in the literature. This highlights the need for methods of making and purifying R-MNTX to high purity.

The present invention provides substantially pure R-MNTX and intermediates thereof, crystals of substantially pure R-MNTX and intermediates thereof, novel methods for making substantially pure R-MNTX, methods for analyzing and quantifying R-MNTX in a mixture of R-MNTX and S-MNTX, methods of isolating R-MNTX from a mixture of R-MNTX and S-MNTX, pharmaceutical products containing the same and related uses of these materials.

The invention provides synthetic routes for stereoselective synthesis of R-MNTX, substantially pure R-MNTX, crystals of substantially pure R-MNTX, pharmaceutical preparations containing substantially pure R-MNTX, and methods for their use.

According to one aspect of the invention, a composition is provided that comprises MNTX in R configuration with respect to nitrogen present at greater than 99.5%. In other embodiments the MNTX in R configuration with respect to nitrogen is present in the composition in greater than about 99.6%, or about 99.7%, or about 99.8%, or about 99.9%, or about 99.95%, or even more preferably greater than 99.95%. In one embodiment, there is no detectable S-MNTX using the chromatographic procedures described herein. Preferably, the composition is free of HPLC detectable S-MNTX. In one embodiment there is no HPLC detectable S-MNTX at a detection limit of 0.02% and a quantitation limit of 0.05%. In yet another embodiment the composition of the invention contains 99.85% of the MNTX is in R configuration with respect to nitrogen and it contains HPLC detectable S-MNTX at a detection limit of 0.02% and a quantitation limit of 0.05%.

According to one aspect of the invention a composition is provided that comprises MNTX, wherein at least 99.6%, 99.7%, 99.8%, 99.85%, 99.9%, and even 99.95% of the MNTX in the composition is in the R configuration with respect to nitrogen, and one or more of a buffering agent, a chelating agent, a preserving agent, a cryoprotecting agent, a lubricating agent, a preservative, an anti-oxidant, or a binding agent.

R-MNTX is a salt. Therefore there will be a counterion, which for the present application, includes the zwitterion. Typically, the counterion a halide, sulfate, phosphate, nitrate or an anionic-charged organic species. Halides include bromide, iodide, chloride, and fluoride. In certain embodiments the halide is iodide and in other important embodiments the halide is bromide. In certain embodiments, the anionic-charged organic species is a sulfonate or a carboxylate. Examples of sulfonates include mesylate, besylate, tosylate, and triflate. Examples of carboxylates include formate, acetate, citrate, and fumarate.

According to another aspect of the invention, the foregoing compositions that comprise MNTX in R configuration with respect to nitrogen in some important embodiments is a crystal, a solution, or a bromide salt of MNTX. In other embodiments, the foregoing compositions are pharmaceutical preparations, preferably in effective amounts and with a pharmaceutically acceptable carrier.

According to one aspect of the invention, a crystal of MNTX is provided that is at least about 99.5%, or about 99.6% or about 99.7%, or is about 99.8%, or about 99.9%, or most preferably greater than 99.95% of MNTX in R configuration with respect to nitrogen.

According to one aspect of the invention, there is provided a compound of the formula:

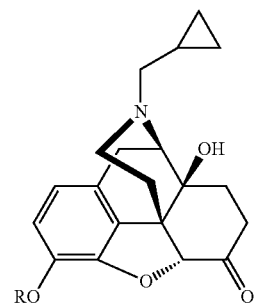

wherein R is a hydroxyl protecting group. The hydroxyl protecting group can be any of numerous such groups. In important embodiments it is selected from the group consisting of: isobutyryl, 2-methyl butyryl, tertbutyl carbonyl, silyl ethers, 2-tetrahydropyranyl ethers, and alkyl carbonates. Most preferably the hydroxyl protecting group is isobutyryl.

According to one aspect of the invention there is provided a compound of the formula:

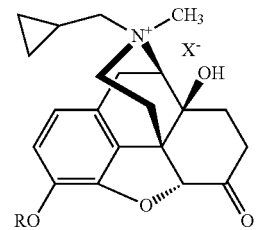

wherein R is a hydroxyl protecting group. The hydroxyl protecting group is selected from the group consisting of: isobutyryl, 2-methyl butyryl, tertbutyl carbonyl, silyl ethers, 2-tetrahydropyranyl ethers, and alkyl carbonates. Most preferably the hydroxyl protecting group is isobutyryl. The compound in one embodiment is isolated. By isolated it is meant the compound is at least 50% pure. The compound can be obtained at levels of even greater purity, such as 60%, 70%, 80%, 90%, or even greater than 95% purity. In other embodiments the compound is in R configuration with respect to nitrogen, the R form being present in greater than 50%, 60%, 70%, 80%, 90%, 95%, 99%, or even 99.5%% versus the S form.

According to another aspect of the invention, a method for stereoselective synthesis of R-MNTX is provided. This method involves adding a hydroxyl protecting group to naltrexone to yield 3-O-protected-naltrexone; methylating the 3-O-protected-naltrexone to yield 3-O-protected-R-MNTX salt; and removing hydroxyl protecting group to yield R-MNTX. In some embodiments of the invention the hydroxyl protecting group can be added in the presence of each or both: an organic solvent and/or a tertiary amine that is not naltrexone. In some embodiments of the invention the naltrexone is methylated by reacting the 3-O-protected-naltrexone with methyl iodide to produce 3-O-protected-R-MNTX iodide salt. The 3-O-protected-naltrexone can be protected in important embodiments by a hydroxyl protecting group such as isobutyryl. In a preferred embodiment of the invention, the 3-O-protected-R-MNTX iodide salt is treated with hydrobromic acid to remove the protecting group and produce R-MNTX bromide/iodide salt, and the bromide/iodide salt is passed through an anion exchange resin column (bromide form) to yield R-MNTX bromide. In any of the foregoing aspects of the invention the tertiary amine that is not MNTX can be triethylamine. In any of the foregoing aspects of the invention the organic solvent can be tetrahydrofuran. In any of the foregoing aspects of the invention the hydroxyl protecting group can be isobutyryl.

According to another aspect of the invention a method for isolation and purification of R-MNTX is provided, comprising passing the crude R-MNTX through a chromatography column and collecting the R-MNTX which elutes at the R-MNTX retention time. This process can be in addition to the method described above, after the deprotecting step and/or the anion exchange resin column step.

According to another aspect of the invention a method for analyzing R-MNTX in a mixture of R-MNTX and S-MNTX is provided. The method involves conducting high performance liquid chromatography (HPLC) and applying R-MNTX to the chromatography column as a standard. The method preferably involves applying both S-MNTX and R-MNTX as standards to determine relative retention/elution times. Relative retention times of R and S are described herein.

Pure S-MNTX can be obtained according to the following procedure: S-MNTX salt can be synthesized by combining iodomethylcyclopropane or another cyclopropylmethyl derivative with oxymorphone in a dipolar aprotic solvent. The cyclopropylmethyl derivative contains a leaving group, preferably a halide, such as iodine or sulfonate. The dipolar aprotic solvent may be: N-methylpyrrolidone (NMP), dimethyl formamide, methylphosphoramide, acetone, 1,4-dioxane, acetonitrile, or combinations thereof. The synthesized S-MNTX can be purified by chromatography, recrystallization, multiple recrystallizations, or a combination thereof. The reaction can be carried out under atmospheric conditions across a wide temperature spectrum, for example, at 70° C., or under a controlled reaction temperature between 65° C. to 75° C. Counterions may be substituted, optionally, for iodide by transferring the S-MNTX iodo salt to a second solvent, such as isopropyl acetate or dioxane and exchanging iodide for a counterion other than iodide. Examples of counterions are bromide, chloride, fluoride, nitrate, sulfonate, or carboxylate. The sulfonate can be mesylate, besylate, tosylate or triflate. The carboxylate can be formate, acetate, citrate and fumarate. The reaction in the second solvent can be conducted at room temperature.

In one aspect of this invention, the chromatography is conducted using two solvents, solvent A and solvent B, wherein solvent A is an aqueous solvent and solvent B is a methanolic solvent and wherein both A and B contain trifluoroacetic acid (TFA). Preferably, A is 0.1% aqueous TFA and B is 0.1% methanolic TFA. In important embodiments the column comprises a bonded, end-capped silica. In important embodiments, the pore size of the column gel is 5 microns. In a most preferred embodiment, the column, flow rate and gradient program are as follows:

Column: Luna C18(2), 150×4.6 mm, 5μ
Flow Rate: 1 mL/min
Gradient Program:

| Time (min) | % A | % B |
| --- | --- | --- |
| 0:00 | 95 | 5 |
| 8:00 | 65 | 35 |
| 12:00 | 35 | 65 |
| 15:00 | 0 | 100 |
| 16:00 | 95 | 5 |
| 18:00 | 95 | 5 |

Detection can be carried out conveniently by ultraviolet (UV) wavelength @ 230 nm. Quantitation Limit is the lowest amount of S-MNTX that can be consistently measured and reported, regardless of variations in laboratories, analysts, instruments or reagent lots. Detection Limit is the lowest amount of S-MNTX in a sample which can be detected but not necessarily quantitated as an exact value.

The foregoing HPLC also can be used to determine the relative amount of S-MNTX and R-MNTX and the intermediates of the synthesis thereof by determining the area under the respective R and S curves in the chromatogram produced. According to another aspect of the invention a method for isolation and purification of R-MNTX and the 3-O-protected-R-MNTX salt intermediate is provided, comprising recrystallizing the crude R-MNTX or intermediates thereof from a solvent or a mixture of solvents. This process can be in addition to the method described above, after the deprotection step and/or the anion exchange resin column step.

According to another aspect of the invention, a method is provided for stereoselective synthesis of 3-O-protected R-MNTX salt comprising methylating a 3-O-protected-naltrexone with a methylating agent to yield 3-O-protected-R-MNTX salt. The hydroxyl protecting group of the 3-O-protected-naltrexone in certain embodiments is isobutyryl, 2-methyl butyryl, tertbutyl carbonyl, silyl ethers, 2-tetrahydropyranyl ethers, and alkyl carbonates. The 3-O-protected R-MNTX is a salt with an anion that can be, for example, a halide, sulfate, phosphate, nitrate or an organic anionic-charged species. The halide is bromide, iodide, chloride, or fluoride. The organic anionic-charged species can be, for example, a sulfonate or carboxylate. Exemplary sulfonates are mesylate, besylate, tosylate, or triflate. Exemplary carboxylates are formate, acetate, citrate, or fumarate. The method can further involve exchanging the anion with a different anion. The methylating agent can be a methyl group susceptible to nucleophilic attack, and a leaving group. Exemplary methylating agents are selected from the group consisting of methyl halide, dimethyl sulfate, methyl nitrate and methyl sulfonate. Methyl halides are methyl iodide, methyl bromide, methyl chloride and methyl fluoride. Methyl sulfonates include methyl mesylate, methyl besylate, methyl tosylate, and methyl triflate. In one embodiment, the methylation is conducted at a temperature range from about >70° C. to about 100° C., or from 80° C. to about 90° C., or preferably at about 88° C. The methylation reaction is conducted for about 1 hour to 24 hours, or about 5 hour to 16 hours and in one embodiment for about 10 hours. The method can further involve purification of the 3-O-protected R-MNTX salt using at least one purification technique, such as chromatography or recrystallization. The chromatography can be reverse-phase chromatography or regular phase chromatography. In some embodiments, the regular phase chromatography can use alumina or silica gel. The 3-O-protected-naltrexone can be purified prior to methylation.

According to one aspect of the invention a pharmaceutical composition is provided that comprises R-MNTX free of detectable S-MNTX by the chromatography procedures described herein or the 3-O-protected-R-MNTX salt intermediate and a pharmaceutically acceptable carrier. In one embodiment the pharmaceutical composition is a packaged unit dosage or a multi-unit dosage. In yet another embodiment the packaged unit dosage is a solution. The pharmaceutical composition in one embodiment is a solution. In another embodiment it is an enteric coated solid dosage form. In still another embodiment it is a sustained release formulation. According to yet another aspect of the invention, a pharmaceutical preparation containing R-MNTX or the 3-O-protected-R-MNTX salt intermediate in a lyophilized formulation is prepared by combining a cryoprotective agent, such as mannitol, with the R-MNTX formulation. The lyophilized preparation may also contain any one of, any combination of, or all of a buffering agent, an antioxidant, an isotonicity agent and an opioid. In some embodiment the aforementioned pharmaceutical composition can further comprise one pharmaceutical agent that is not an opioid antagonist. In one embodiment of the invention the aforementioned pharmaceutical composition can comprise a pharmaceutical agent that is an opioid. In yet another embodiment, the pharmaceutical composition can further comprise at least one opioid, and at least one pharmaceutical agent that is not an opioid or an opioid antagonist. In a preferred embodiment the pharmaceutical agent that is not an opioid or an opioid antagonist is an antiviral agent, an anti-infective agent, an anticancer agent, an antispasmodic agent, an anti-muscarinic agent, a steriodal or non-steriodal anti-inflammatory agent, a pro-motility agent, a $5HT_1$ agonist, a $5HT_3$ antagonist, a $5HT_4$ antagonist, a $5HT_4$ agonist, a bile salt sequestering agent, a bulk-forming agent, an alpha2-adrenergic agonist, a mineral oil, an antidepressant, a herbal medicine, an anti-diarrheal medication, a laxative, a stool softener, a fiber or a hematopoietic stimulating agent.

The pharmaceutical compositions of the invention can be provided in kits. The kits are a package containing a sealed container comprising the pharmaceutical preparations of the present invention and instructions for use. The kits contain R-MNTX that is free of HPLC detectable S-MNTX. The kit in one embodiment contains 40 mg/mL R-MNTX. The kit in another embodiment contains 30 mg/mL of R-MNTX. The kit can further include an opioid or opioid agonist, or it can include at least one pharmaceutical agent that is not an opioid or an opioid antagonist. In one embodiment, the kit is a package containing a sealed container comprising the pharmaceutical preparation that is or the 3-O-protected-R-MNTX salt and instructions for use. The kit in one embodiment contains 40 mg/mL 3-O-protected-R-MNTX salt. The kit in another embodiment contains 30 mg/mL of 3-O-protected-R-MNTX salt. The kit can further include an opioid or opioid agonist, or it can include at least one pharmaceutical agent that is not an opioid or an opioid antagonist.

According to another aspect of the invention, methods are provided for ensuring the manufacture of R-MNTX (which is an opioid antagonist) that is free of S-MNTX (which is an opioid agonist). The methods permit for the first time the assurance that a pharmaceutical preparation of R-MNTX which is intended for antagonist activity is not contaminated with a compound that opposes the activity of R-MNTX. This is particularly desirable when R-MNTX is administered to oppose the side effects of opioid therapy, as opioids appear to act synergistically with S-MNTX to oppose the activity of R-MNTX. In this aspect of the invention, a method is provided for manufacturing R-MNTX. The method involves:

(a) obtaining a first composition containing R-MNTX, (b) purifying the first composition by chromatography, recrystallization or a combination thereof, (c) conducting HPLC on a sample of purified first composition using S-MNTX as a standard, and (d) determining the presence or absence of S-MNTX in the sample. In an important embodiment, both R-MNTX and S-MNTX are used as standards, to determine for example relative retention time of R-MNTX and S-MNTX. In one embodiment, the purifying is multiple recryallization steps or multiple chromatography steps. In another embodiment, the purifying is carried out until S-MNTX is absent from the sample as determined by HPLC. It should be understood, however, that the purified first composition in some aspects of the invention is not necessarily free of detectable S-MNTX. The presence of such S-MNTX, for example, might indicate that further purification steps should be conducted if purer R-MNTX is desired. The methods can further involve packaging purified first composition that is free of HPLC detectable S-MNTX. The methods further can include providing indicia on or within the packaged, purified first composition indicating that the packaged, purified first composition is free of HPLC detectable S-MNTX. The method further can involve packaging a pharmaceutically effective amount for treating anyone of the conditions described herein. The first composition containing R- and S-MNTX can be obtained by the methods described herein.

According to one aspect of the invention, the purifying is carried out until S-MNTX is less than 0.4%, 0.3%, 0.2%, 0.15%, 0.1%, 0.05%, even is absent from the purified first composition as determined by HPLC with a detection limit of 0.02 and a quantitation limit of 0.05%.

In one embodiment the method provides indicia on or with the packaged purified first composition indicating a level of S-MNTX in the packaged first purified composition.

According to one aspect of the invention a package is provided that contains a composition comprising R-MNTX and indicia on or contained within the package indicating a level of S-MNTX in the composition. In one embodiment the level of S-MNTX is less than 0.4%, 0.3%, 0.2%, 0.15%, 0.1%, 0.05%, or is absent from the sample. In yet another embodiment, the package further contains, mixed together with the R-MNTX, one or more of a buffering agent, a chelating agent, a preserving agent, a cryoprotecting agent, a lubricating agent, a preservative, an anti-oxidant, or a binding agent.

According to one aspect of the invention a method of preparing a pharmaceutical product in provided, by selecting a composition of R-MNTX because it contains S-MNTX at a level that is less than 0.4%, 0.3%, 0.2%, 0.15%, 0.1%, 0.05% of, or is absent from the composition, and formulating the composition into a unit or multi-unit dosage for administration to a patient.

According to another aspect of the invention, a packaged product is provided. The package contains a composition comprising R-MNTX, wherein the composition is free of HPLC detectable S-MNTX, and indicia on or contained within the package indicating that the composition is free of detectable S-MNTX. The composition can take on a variety of forms, including, but not limited to, a standard for use in laboratory experiments, a standard for use in manufacturing protocols, or a pharmaceutical composition. If the composition is a pharmaceutical composition, then one important form of indicia is writing on a label or package insert describing the characteristics of the pharmaceutical preparation. The indicia can indicate directly that the composition is free of S-MNTX, or it can indicate the same indirectly, by stating for example that the composition is pure or 100% R-MNTX. The pharmaceutical composition can be for treating any of the conditions described herein. The pharmaceutical composition can contain an effective amount of the pure R-MNTX and can take any of the forms described below as if specifically recited in this summary, including, but not limited to, solutions, solids, semi-solids, enteric coated materials and the like.

According to one aspect of the invention, a method is provided for treating or preventing opioid-induced side effects comprising administering to a patient the R-MNTX free of detectable S-MNTX by the chromatography procedures described herein or the 3-O-protected-R-MNTX salt intermediate composition of any of the foregoing aspects of the invention in an amount effective to treat the opioid-induced side effect. In one embodiment of the invention the patient is chronically administered opioids. In another embodiment the patient is acutely administered opioids. The opioid-induced side effect is preferably selected from a group consisting of constipation, immune suppression, inhibition of gastrointestinal motility, inhibition of gastric emptying, nausea, emesis, incomplete evacuation, bloating, abdominal distension, increased gastroesophageal reflux, hypotension, bradycardia, gastrointestinal dysfunction, pruritus, dysphoria, and urinary retention. In one preferred embodiment the opioid-induced side effect is constipation. In another preferred embodiment the opioid-induced side effect is inhibition of gastrointestinal motility or inhibition of gastric emptying. In yet another preferred embodiment the opioid-induced side effect is nausea or emesis. In yet another preferred embodiment the opioid-induced side effect is pruritus. In yet another preferred embodiment the opioid-induced side effect is dysphoria. In yet another preferred embodiment the opioid-induced side effect is urinary retention.

According to one aspect of the invention, a method is provided for treating a patient receiving an opioid for pain resulting from surgery comprising administering to the patient an R-MNTX composition free of detectable S-MNTX by the chromatography procedures described herein or the 3-O-protected-R-MNTX salt intermediate in an amount effective to promote gastrointestinal motility, gastric emptying or relief of constipation.

According to another aspect of the invention, a method is provided for inducing laxation in a patient in need of laxation, comprising administering to the patient an R-MNTX composition free of detectable S-MNTX by the chromatography procedures described herein or the 3-O-protected-R-MNTX salt intermediate in an effective amount.

According to yet another aspect of the invention, a method is provided for preventing and/or treating impaction in a patient in need of such prevention/treatment, comprising administering to the patient an R-MNTX composition free of detectable S-MNTX by the chromatography procedures described herein or the 3-O-protected-R-MNTX salt intermediate in an effective amount.

According to yet another aspect of the invention, a method is provided for preventing and/or treating post-operative bowel dysfunction following surgery, in particular abdominal surgery in a patient in need of such prevention/treatment, comprising administering to the patient an R-MNTX composition free of detectable S-MNTX by the chromatography procedures described herein or the 3-O-protected-R-MNTX salt intermediate in an effective amount.

According to one aspect of the invention, a method is provided for treating or preventing endogenous opioid-induced gastrointestinal dysfunction comprising administering to the patient an R-MNTX composition free of detectable S-MNTX by the chromatography procedures described herein or the 3-O-protected-R-MNTX salt intermediate in an amount effective to treat the endogenous opioid-induced gastrointestinal dysfunction. The gastrointestinal dysfunction can be selected from a group consisting of inhibition of gastrointestinal motility, constipation and ileus. In some embodiments of the invention the ileus is selected from the group comprising of: post-operative ileus, post-partum ileus, paralytic ileus.

According to one aspect of the invention, a method is provided for preventing or treating idiopathic constipation comprising administering to the patient an R-MNTX composition free of detectable S-MNTX by the chromatography procedures described herein or the 3-O-protected-R-MNTX salt intermediate in an amount effective to prevent or treat the idiopathic constipation.

According to yet another aspect of the invention, a method is provided for treating irritable bowel syndrome comprising administering to the patient an R-MNTX composition free of detectable S-MNTX by the chromatography procedures described herein or the 3-O-protected-R-MNTX salt intermediate in an amount effective to ameliorate at least one symptom of the irritable bowel syndrome. In some embodiments of the invention the R-MNTX composition or the 3-O-protected-R-MNTX salt composition further comprises at least one irritable bowel syndrome therapeutic agent. The irritable bowel syndrome therapeutic agent can be selected from the groups consisting of antispasmodics, anti-muscarinics, anti-inflammatory agents, pro-motility agents, $5HT_1$ agonists, $5HT_3$ antagonists, $5HT_4$ antagonists, $5HT_4$ agonists, bile salt sequestering agents, bulk-forming agents, alpha2-adrenergic agonists, mineral oils, antidepressants, herbal medicines, anti-diarrheal medication and combinations thereof.

According to one aspect of the invention methods are provided for parenteral administration of the compounds and compositions of the invention including but not limited to intravenous, intramuscular and subcutaneous administration. In one embodiment of the invention the compounds of the invention are in pharmaceutical preparations suitable for use in pre-filled syringes, pre-filled pen injectors, cartridges for use in pen injectors, reusable syringes or other medical injectors, liquid dry injectors, needleless pen systems, syrettes, autoinjectors, or other patient-controlled injection devices.

These and other aspects of the invention are described in greater detail herein.

DETAILED DESCRIPTION

Figure 1:
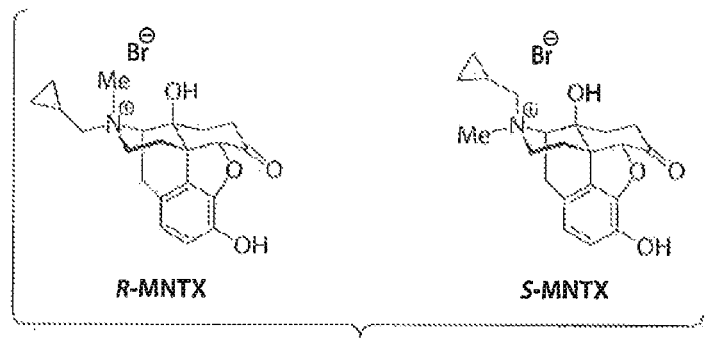
FIG. 1 provides the chemical structure of bromide salts of R-MNTX and S-MNTX.

The invention provides synthetic routes for stereoselective synthesis of R-MNTX, [morphinanium, 17R, 17-(cyclopropylmethyl)-4,5-epoxy-3,14-dihydroxy-17-methyl-6-oxo-, salt, (5α)-(9Cl)], substantially pure R-MNTX, crystals of substantially pure R-MNTX, pharmaceutical preparations containing substantially pure R-MNTX, and methods for their use.

R-MNTX has the structure in the formula:

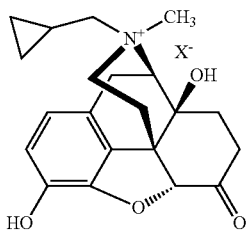

wherein X⁻ is a counterion. The counterion can be any counter ion, including a zwitterion. Preferably the counterion is pharmaceutically acceptable. Counterions include halides, sulfates, phosphates, nitrates, and anionic-charged organic species. The halide can be iodide, bromide, chloride, fluoride or a combination thereof. In one embodiment the halide is iodide. In a preferred embodiment the halide is bromide. The anionic-charged organic species may be a sulfonate or carboxylate. The sulfonate may be mesylate, besylate, tosylate, or triflate. The carboxylate may be formate, acetate, citrate, or fumarate.

The invention further provides an R-MNTX intermediate, isolated 3-O-protected-R-MNTX salt of the formula:

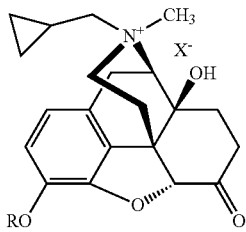

wherein R is a hydroxyl protecting group, substantially pure 3-O-protected-R-MNTX salt, crystals of substantially pure 3-O-protected-R-MNTX salt, pharmaceutical preparations containing substantially pure 3-O-protected-R-MNTX salt, and methods for their use. The invention further provides synthetic routes for stereoselective synthesis of 3-O-protected-R-MNTX salt.

"Alkyl", in general, refers to an aliphatic hydrocarbon group which may be straight, branched or cyclic having from 1 to about 10 carbon atoms in the chain, and all combinations and subcombinations of ranges therein.

"Branched" refers to an alkyl group in which a lower alkyl group, such as methyl, ethyl or propyl, is attached to a linear alkyl chain. In certain preferred embodiments, the alkyl group is a $C_1$-$C_5$ alkyl group, i.e., a branched or linear alkyl group having from 1 to about 5 carbons. In other preferred embodiments, the alkyl group is a $C_1$-$C_3$ alkyl group, i.e., a branched or linear alkyl group having from 1 to about 3 carbons. Exemplary alkyl groups include methyl, ethyl, n-propyl, isopropyl, butyl, isobutyl, sec-butyl, tert-butyl, pentyl, hexyl, heptyl, octyl, nonyl and decyl. "Lower alkyl" refers to an alkyl group having 1 to about 6 carbon atoms. Preferred alkyl groups include the lower alkyl groups of 1 to about 3 carbons.

An "alkylating agent" is a compound that can be reacted with a starting material to bind, typically covalently, an alkyl group to the starting material. The alkylating agent typically includes a leaving group that is separated from the alkyl group at the time of attachment to the starting material. Leaving groups may be, for example, halogens, halogenated sulfonates or halogenated acetates. An example of an alkylating agent is cyclopropylmethyl iodide.

"Methylating agent" means a reactive species, having electrophilic properties, that is capable of introducing a "methyl group" at the nitrogen atom of naltrexone, so as to form a covalent bond therewith. Illustrative methylating agents can be represented by the formula $CH_3Z$, wherein "Z" is a leaving group which, upon its departure, enables $CH_3$ to form a covalent bond with the nitrogen atom of naltrexone, forming MNTX. Methylating agents in general, and leaving groups in general, are well known to those of ordinary skill in the art and are described extensively in both the patent literature and in chemistry text books. Suitable Z groups include, but are not limited to, fluoro, chloro, bromo, iodo, —$OSO_2CF_3$, $CH_3OSO_2O$—, —$OSO_2CH_3$, —$OSO_2C_6H_4$-p-$CH_3$, —$OSO_2C_6H_4$-p-Br.

"Alkenyl", in general, refers to an alkyl group containing at least one carbon-carbon double bond and having from 2 to about 10 carbon atoms in the chain, and all combinations and subcombinations of ranges therein. In certain preferred embodiments, the alkenyl group is a $C_2$-$C_{10}$ alkyl group, i.e., a branched or linear alkenyl group having from 2 to about 10 carbons. In other preferred embodiments, the alkenyl group is a $C_2$-$C_6$ alkenyl group, i.e., a branched or linear alkenyl group having from 2 to about 6 carbons. In still other preferred embodiments, the alkenyl group is a $C_3$-$C_{10}$ alkenyl group, i.e., a branched or linear alkenyl group having from about 3 to about 10 carbons. In yet other preferred embodiments, the alkenyl group is a $C_2$-$C_5$ alkenyl group, i.e., a branched or linear alkenyl group having from 2 to about 5 carbons. Exemplary alkenyl groups include, for example, vinyl, propenyl, butenyl, pentenyl, hexenyl, heptenyl, octenyl, nonenyl and decenyl groups.

"Alkylene", in general, refers to a straight or branched bivalent aliphatic hydrocarbon group having from 1 to about 6 carbon atoms, and all combinations and subcombinations of ranges therein. The alkylene group may be straight, branched or cyclic. Exemplary alkylene groups include, for example, methylene (—$CH_2$—), ethylene (—$CH_2$—$CH_2$—) and propylene (—$(CH_2)_3$—). There may be optionally inserted along the alkylene group one or more oxygen, sulfur or optionally substituted nitrogen atoms, wherein the nitrogen substituent is alkyl as described previously. Preferred alkylene groups have from about 1 to about 4 carbons.

"Alkenylene", in general, refers to an alkylene group containing at least one carbon-carbon double bond. Exemplary alkenylene groups include, for example, ethenylene (—CH═CH—) and propenylene (—CH═CHCH$_2$—). Preferred alkenylene groups have from 2 to about 4 carbons.

"Cycloalkyl", in general, refers to any stable monocyclic or bicyclic ring having from about 3 to about 10 carbons, and all combinations and subcombinations of ranges therein. In preferred embodiments, the cycloalkyl group is a C$_3$-C$_8$ cycloalkyl group, i.e., a cycloalkyl group having from about 3 to about 8 carbons, with C$_3$-C$_6$ cycloalkyl groups, i.e., cycloalkyl groups having from about 3 to about 6 carbons being more preferred. The cycloalkyl group may be optionally substituted with one or more cycloalkyl group substituents. Preferred cycloalkyl group substituents include alkyl, preferably C$_1$-C$_3$ alkyl, alkoxy, preferably C$_1$-C$_3$ alkoxy, or halo. Exemplary cycloalkyl groups include, for example, cyclopropyl, cyclobutyl, cyclopentyl, cyclohexyl, cycloheptyl and cyclooctyl groups.

"Cycloalkyl-substituted alkyl", in general, refers to a linear alkyl group, preferably a lower alkyl group, substituted at a terminal carbon with a cycloalkyl group, preferably a C$_3$-C$_8$ cycloalkyl group. Typical cycloalkyl-substituted alkyl groups include cyclohexylmethyl, cyclohexylethyl, cyclopentylethyl, cyclopentylpropyl, cyclopropylmethyl and the like.

"Cycloalkenyl", in general, refers to an olefinically unsaturated cycloalkyl group having from about 4 to about 10 carbons, and all combinations and subcombinations of ranges therein. In preferred embodiments, the cycloalkenyl group is a C$_5$-C$_8$ cycloalkenyl group, i.e., a cycloalkenyl group having from about 5 to about 8 carbons.

"Alkoxy", in general, refers to an alkyl-O— group where alkyl is as previously described. Exemplary alkoxy groups include, for example, methoxy, ethoxy, propoxy, butoxy and heptoxy.

"Alkoxy-alkyl", in general, refers to an alkyl-O-alkyl group where alkyl is as previously described.

"Acyl", in general, means an alkyl-CO— group wherein alkyl is as previously described. Preferred acyl groups comprise lower alkyl groups, such as alkyl of about 1 to about 3 carbons. Exemplary acyl groups include acetyl, propanoyl, 2-methylpropanoyl, and butanoyl.

"Aryl", in general, refers to an aromatic carbocyclic radical containing 6, 10 or 14 carbons. The phenyl group may be optionally substituted with one or two or more substituents. Preferred aryl group substituents include alkyl groups, preferably C$_1$-C$_5$ alkyl groups. Exemplary aryl groups include phenyl and naphthyl.

"Aryl-substituted alkyl", in general, refers to an linear alkyl group, preferably a lower alkyl group, substituted at a carbon with an optionally substituted aryl group, preferably an optionally substituted phenyl ring. Exemplary aryl-substituted alkyl groups include, for example, phenylmethyl, phenylethyl and 3-(4-methylphenyl)propyl.

"Heterocyclic", in general, refers to a monocyclic or multicyclic ring system radical containing from about 4 to about 10 members, and all combinations and subcombinations of ranges therein, wherein one or more of the members is an element other than carbon, for example, nitrogen, oxygen or sulfur. The heterocyclic group may be aromatic or nonaromatic. Exemplary heterocyclic groups include, for example, isoxazole, pyrrole and piperidine groups.

"Organic solvent" has its common ordinary meaning to those of skill in this art. Exemplary organic solvents useful in the invention include, but are not limited to tetrahydrofuran, acetone, hexane, ether, chloroform, acetic acid, acetonitrile, chloroform, cyclohexane, methanol, and toluene. Anhydrous organic solvents are included.

"Dipolar aprotic" solvents are protophilic solvents that cannot donate labile hydrogen atoms and that exhibit a permanent dipole moment. Examples include acetone, ethyl acetate, dimethyl sulfoxide (DMSO), dimethyl formamide (DMF) and N-methylpyrrolidone.

"Dipolar protic" solvents are those that can donate labile hydrogen atoms and that exhibit a permanent dipole moment. Examples include water, alcohols such as 2-propanol, ethanol, methanol, carboxylic acids such as formic acid, acetic acid, and propionic acid.

"Tertiary amines" has its common, ordinary meaning. In general, the tertiary amines useful in the invention have the general formula:

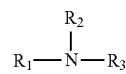

wherein R$_1$, R$_2$, and R$_3$ are identical or a combination of different straight or branched chain alkyl groups, alkenyl groups, alkylene groups, alkenylene groups, cycloalkyl groups, cycloalkyl-substituted alkyl groups, cycloalkenyl groups, alkoxy groups, alkoxy-alkyl groups, acyl groups, aryl groups, aryl-substituted alkyl groups, and heterocyclic groups. Exemplary tertiary amines useful according to the invention are those where R$_{1-3}$ is an alkyl group of the formula (C$_n$H$_{2n+1}$, n=1-4), or aralkyl group of the formula (C$_6$H$_5$ (CH$_2$)$_n$— [n=1-2]. Exemplary tertiary amines useful according to the invention also are cycloalkyl tertiary amines (e.g., N-methylmorpholine, N-methylpyrrolidine, N-methylpiperidine), pyridine and Proton Sponge® (N,N, N',N'-tetramethyl-1,8-naphthalene).

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups are those that are stable during formation, isolation and purification. A preferred protecting group is an isobutyryl groups,); silyl ethers (SiR$_3$, wherein each R can be independently C$_1$-C$_6$ alkyl, straight chain or branched); 2-tetrahydropyranyl ether, alkyl carbonates; a benzyloxycarbonyl group and a tert-butyloxycarbonyl group. Other preferred protecting groups that may be employed in accordance with the present invention are described in Greene, T. W. and Wuts, P. G. M., Protective Groups in Organic Synthesis 2d. Ed., Wiley & Sons, 1991. The expression "hydroxyl protective group" as used hereinbelow is intended to designate a group which is inserted in place of the hydrogen atom of an OH group.

When the hydroxyl protective group is an aliphatic ester it preferably represents an radical selected from the group consisting of alkanoyl having 3 to 8 carbon atoms; alkenoyl having one or two double bonds and 3 to 8 carbon atoms;

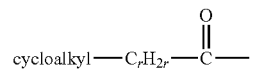

wherein the cycloalkyl portion contains 3 to 7 ring atoms and r is zero, one, two or three; phenoxyacetyl; pyridinecarbonyl; and

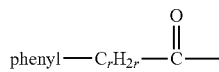

wherein r is zero, one, two or three and phenyl is unsubstituted or is substituted by 1 to 3 alkyl groups each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, propionyl, butyryl, isobutyryl, valeryl, isovaleryl, 2-methylbutanoyl, pivalyl(pivaloyl), 3-methylpentanoyl, 3,3-dimethylbutanoyl, 2,2-dimethylpentanoyl and the like. Pivalyl, isobutyryl and isovaleryl are important examples.

When the acyl group is alkenoyl, there are included, for example, crotonyl, 2,5-hexadienoyl and 3,6-octadienoyl.

When the acyl group is

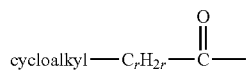

there are included cycloalkanecarbonyl and cycloalkanealkanoyl groups wherein the cycloalkane portion can optionally bear 1 or 2 alkyl groups as substituents, e.g. cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl. Cyclohexanecarbonyl is especially preferred.

When the acyl group is pyridinecarbonyl, there are included picolinoyl(2-pyridinecarbonyl), nicotinoyl(3-pyridinecarbonyl) and isonicotinoyl(4-pyridinecarbonyl).

When the acyl group is

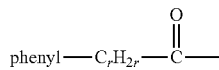

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, 3,4-diethoxyphenylacetyl, β-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl, p-n-butoxybenzoyl, 2,4,6-triethoxybenzoyl, β-(p-trifluoromethylphenyl)propionyl, 2-methyl-4-methoxybenzoyl, p-acetamidophenylpropionyl and 3-chloro-4-ethoxybenzoyl.

When the hydroxyl protective group is a carbonate grouping, it has the structural formula

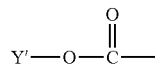

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

cycloalkyl-C$_r$H$_{2r}$— wherein the cycloalkyl portion contains 3 to 7 ring atoms and r is zero, one, two or three; phenoxy; 2-, 3-, or 4-pyridyl; or phenyl-C$_r$H$_{2r}$— wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is C$_1$-C$_7$ alkyl, particularly ethyl or isopropyl.

Preferred protecting groups are those that can be selectively appended to a functionality. These groups render such functionality inert to chemical reaction conditions to which the compound may be exposed. After the protecting group has served its purpose it can be selectively removed from the functionality without altering the molecular structure. Most preferred protecting groups are those that can be selectively appended to and removed from the functionality under mild conditions, in high yield.

Preferred protecting groups for 3-O-protected-naltrexone include those that are more stable and sterically hindered compared to an acetyl protecting group, which was found to be unstable during preparation and purification, thus resulting in lower yield and purity, and difficulty in handling. Examples of preferred protecting groups for use in the method of the present invention include isobutyryl, 2-methyl butyryl, tertbutyl carbonyl and the like. In a preferred embodiment, the protecting group is isobutyryl, due to its greater stability which results in higher yield and purity. Such protecting groups provide yields of 3-O-protected-naltrexone of greater than 70, preferably greater than 75%. In one embodiment, yield of 3-O-protected-naltrexone is about 80% or greater.

Although some of the foregoing protecting groups and tertiary amines are not substituted, those of ordinary skill in the art will understand that substitutions can be present in some circumstances.

The present invention provides a method for stereoselective synthesis of R-MNTX comprising;
(a) methylating a 3-O-protected-naltrexone with a methylating agent to yield 3-O-protected-R-MNTX salt; and
(b) hydrolysis to remove the 3-hydroxyl protecting group to yield R-MNTX. Preferred hydroxyl protecting groups of the 3-O-protected-R-MNTX salt include isobutyryl, 2-methyl butyryl, tertbutyl carbonyl, silyl ethers, 2-tetrahydropyranyl ethers, and alkyl carbonates.

Unlike the method described by Goldberg et al which teaches room temperature for three weeks or 70° C. for seven days for the methylation reaction to produce N-MNTX, the stereoselective methylation conditions of the present invention are conducted at a temperature above 70° C., more preferably above 80° C. In one embodiment, the reaction is carried out at about 88° C. Based on the standard principles of chemical reactions involving stereoisomers, one would expect at higher temperatures the reaction would proceed with kinetic control resulting in a mixture of R-MNTX and S-MNTX with high percentages of both stereoisomers. It was surprising that at elevated temperatures the method of the present invention provided predominantly the R-MNTX rather than a mixture with a higher percentage of S-MNTX.

The methylation reaction of the present invention is allowed to proceed from 1 hour to about 24 hours, preferably about 5 hours to about 16 hours, more preferably about 8 to 12 hours, most preferably about 10 hours. This reaction time offers a major industrial scale advantage over the three weeks at room temperature or seven days at 70° C. taught by Goldberg et al.

In a preferred embodiment, the methylation reaction is conducted at about 88° C. for 10 hours. These reaction parameters are highly desirable for the development of a process amenable to scale-up in industrial scale.

The present invention further provides a method of purifying R-MNTX from a mixture of stereoisomers of R-MNTX and S-MNTX, the method comprising at least one, two or multiple recrystallizations. The recrystallized product is highly enriched in R-MNTX and substantially devoid of S-MNTX. In one embodiment the recrystallized product is greater than 98% pure R-MNTX. It is understood that an artisan skilled in the art can optimize this methodology to obtain higher purity and/or higher yield of R-MNTX in which the recrystallized product is greater than 99% pure R-MNTX and even greater than 99.9% pure R-MNTX.

The recrystallization solvent can be an organic solvent or a mixture of organic solvents or a mixture of organic solvent(s) plus water. A preferred solvent is an alcohol, more preferred a low molecular weight alcohol. In one embodiment, the low molecular weight alcohol is methanol.

Goldberg et al., and Cantrell et al., make use of organic solvent(s)/water for recrystallization. This is a standard practice to clean up a reaction mixture. It is not the Goldberg et al's nor Cantrell et al's stated goal to obtain one stereoisomer over the other, as they do not address the existence of stereoisomers, or whether a stereoisomer is obtained preferentially. Therefore, neither Goldberg et al., nor Cantrell et al., address the impact that recrystallization may have on the composition of stereoisomers. The present invention discloses the conditions under which recrystallization can be used advantageously to increase the purity of R-MNTX from a mixture of R-MNTX and S-MNTX.

One aspect of the invention is a method of resolving and identifying R-MNTX and S-MNTX in a solution of MNTX. The R-MNTX also is useful in HPLC assay methods of quantifying an amount of R-MNTX in a composition or mixture in which the method comprises applying a sample of the composition or mixture to a chromatography column, resolving the components of the composition or mixture, and calculating the amount of R-MNTX in the sample by comparing the percentage of a resolved component in the sample with the percentage of a standard concentration of R-MNTX. The method is particularly useful in reverse phase HPLC chromatography.

The pharmaceutical preparations of the invention, when used alone or in cocktails, are administered in therapeutically effective amounts. A therapeutically effective amount will be determined by the parameters discussed below; but, in any event, is that amount which establishes a level of the drug(s) effective for treating a subject, such as a human subject, having one of the conditions described herein. An effective amount means that amount alone or with multiple doses, necessary to delay the onset of, lessen the severity of, or inhibit completely, lessen the progression of, or halt altogether the onset or progression of the condition being treated or a symptom associated therewith. In the case of constipation, an effective amount, for example, is that amount which relieves a symptom of constipation, which induces a bowel movement, which increases the frequency of bowel movements, or which decreases oral-cecal transit time. The known and conventional definition of constipation is (i) less than one bowel movement in the previous three days or (ii) less than three bowel movements in the previous week (See e.g., U.S. Pat. No. 6,559,158). In other words, a patient is not constipated (i.e., has "regular bowel movements" as used herein) if the patient has at least one bowel movement every three days and at least three bowel movements per week. Accordingly, at least one bowel movement every two days would be considered regular bowel movements. Likewise, at least one bowel movement per day is a regular bowel movement. Effective amounts therefore can be those amounts necessary to establish or maintain regular bowel movements.

In certain instances, the amount is sufficient to induce a bowel movement within 12 hours of administration of the R-MNTX or the R-MNTX intermediate, 3-O-protected-R-MNTX salt, 10 hours, 8 hours, 6 hours, 4 hours, 2 hours, 1 hour and even immediately upon administration, depending upon the mode of administration. Intravenous administration can produce an immediate effect of laxation in chronic opioid users. Subcutaneous administration can result in a bowel movement within 12 hours of administration, preferably within 4 hours of administration. When administered to a subject, effective amounts will depend, of course, on the particular condition being treated; the severity of the condition; individual patient parameters including age, physical condition, size and weight; concurrent treatment and, especially, concurrent treatment with opioids where opioids are administered chronically; frequency of treatment; and the mode of administration. These factors are well known to those of ordinary skill in the art and can be addressed with no more than routine experimentation.

Patients amenable to the therapy of the present invention include but are not limited to terminally ill patients, patients with advanced medical illness, cancer patients, AIDS patients, post-operative patients, patients with chronic pain, patients with neuropathies, patients with rheumatoid arthritis, patients with osteoarthritis, patients with chronic back pain, patients with spinal cord injury, patients with chronic abdominal pain, patients with chronic pancreatic pain, patients with pelvic/perineal pain, patients with fibromyalgia, patients with chronic fatigue syndrome, patients infected with HCV, patients with irritable bowel syndrome, patients with migraine or tension headaches, patients with sickle cell anemia, patients on hemodialysis, and the like.

Patients amenable to the therapy of the present invention also include but are not limited to patients suffering from dysfunctions caused by endogenous opioids, especially in post-operative settings. In certain embodiments, the R-MNTX or intermediate thereof is present in an amount sufficient to accelerate discharge from hospital post-surgery, including abdominal surgeries such as rectal resection, colectomy, stomach, esophageal, duodenal, appendectomy, hysterectomy, or non-abdominal surgeries such as orthopedic, trauma injuries, thoracic or transplantation surgery. This treatment can be effective to shorten the length of the time in the hospital, or to shorten the time to a hospital discharge order written post-operatively by shortening the time to bowel sounds after surgery, or first flatus, to first laxation or to solid diet intake following surgery. The R-MNTX or intermediate thereof may continue to be provided after the patient has ceased to receive opioid pain medications post-operatively.

Certain patients particularly amenable to treatment are patients having the symptoms of constipation and/or gastrointestinal immotility and who have failed to obtain relief or ceased to obtain relief or a consistent degree of relief of their symptoms using a laxative or a stool softener, either alone or in combination, or who are otherwise resistant to laxatives and/or stool softeners. Such patients are said to be refractory to the conventional laxatives and/or stool softeners. The constipation and/or gastrointestinal immotility may be induced or a consequence of one or more diverse conditions including, but not limited to, a disease condition, a physical condition, a drug-induced condition, a physiological imbalance, stress, anxiety, and the like. The conditions inducing constipation and/or gastrointestinal immotility may be acute conditions or chronic conditions.

The subjects can be treated with a combination of R-MNTX, or the 3-O-protected-R-MNTX intermediate thereof, and a laxative and/or a stool softener (and optionally, an opioid). In these circumstances the R-MNTX or the intermediate thereof and the other therapeutic agent(s) are administered close enough in time such that the subject experiences the effects of the various agents as desired, which typically is at the same time. In some embodiments the R-MNTX or the intermediate thereof will be delivered first in time, in some embodiments second in time, and still in some embodiments at the same time. As discussed in greater detail herein, the invention contemplates pharmaceutical preparations where the R-MNTX or intermediate thereof is administered in a formulation including the R-MNTX or the intermediate thereof and one or both of a laxative and a stool softener (and, optionally, an opioid). These formulations may be parenteral or oral, such as the ones described in U.S. Ser. No. 10/821,809. Included are solid, semisolid, liquid, controlled release, lyophilized and other such formulations.

In an important embodiment, the administered amount of R-MNTX is sufficient to induce laxation. This has particular application where the subject is a chronic opioid user. Chronic opioid use as used herein includes daily opioid treatment for a week or more or intermittent opioid use for at least two weeks. It previously was determined that patients receiving opioids chronically become tolerant to opioids and need increasing doses. Thus, a patient receiving oral doses of opioids chronically would be receiving typically between 40 and 100 mg per day of a morphine-equivalent dose of opioid. It likewise was determined surprisingly that such subjects become more responsive to the effects of MNTX and that surprisingly lower doses induced side effects. Thus, to induce immediate laxation, it requires on the order of only about 0.15 mg/kg MNTX intravenously. For oral administration, a sufficient dose is believed to be less than 3 mg/kg uncoated and even less when the R-MNTX is enterically coated.

Patients using opioids chronically include late stage cancer patients, elderly patients with osteoarthritic changes, methadone maintenance patients, neuropathic pain and chronic back pain patients. Treatment of these patients is important from a quality of life standpoint, as well as to reduce complications arising from chronic constipation, such as hemorrhoids, appetite suppression, mucosal breakdown, sepsis, colon cancer risk, and myocardial infarction.

The opioid can be any pharmaceutically acceptable opioid. Common opioids are those selected from the group consisting of alfentanil, anileridine, asimadoline, bremazocine, burprenorphine, butorphanol, codeine, dezocine, diacetylmorphine (heroin), dihydrocodeine, diphenoxylate, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, opium, oxycodone, oxymorphone, pentazocine, propiram, propoxyphene, remifentanyl, sufentanil, tilidine, trimebutine, and tramadol. The opioid also may be mixed together with the R-MNTX or intermediate thereof and provided in any of the forms described above in connection with R-MNTX or intermediate thereof.

Generally, oral doses of R-MNTX and intermediates thereof will be from about 0.25 to about 19.0 mg/kg body weight per day. Generally, parenteral administration, including intravenous and subcutaneous administration, will be from about 0.01 to 1.0 mg/kg body weight depending on whether administration is as a bolus or is spread out over time such as with an I.V. drip. Generally, the I.V. dose for post-operative bowel dysfunction (POBD) is 0.3 mg/kg. It is expected that doses ranging from 0.01 to 0.45 mg/kg body weight will yield the desired results. Dosage may be adjusted appropriately to achieve desired drug levels, local or systemic, depending on the mode of administration. For example, it is expected that the dosage for oral administration of the opioid antagonists in an enterically-coated formulation would be lower than in an immediate release oral formulation. In the event that the response in a patient is insufficient at such doses, even higher doses (or effectively higher dosage by a different, more localized delivery route) may be employed to the extent that the patient tolerance permits. Multiple doses per day are contemplated to achieve appropriate systemic levels of compounds. Appropriate systemic levels can be determined by, for example, measurement of the patient's peak or sustained plasma level of the drug. Peak plasma levels below 100 ng/ml are preferred in some instances. "Dose" and "dosage" are used interchangeably herein.

A variety of administration routes are available. The particular mode selected will depend, of course, upon the particular combination of drugs selected, the severity of the condition being treated, or prevented, the condition of the patient, and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, transdermal, sublingual, intravenous infusion, pulmonary, intra-arterial, intra-adipose tissue, intra-lymphatic, intramuscular, intracavity, aerosol, aural (e.g., via eardrops), intranasal, inhalation, intra-articular, needleless injection, subcutaneous or intradermal (e.g., transdermal) delivery. For continuous infusion, a patient-controlled analgesia (PCA) device or an implantable drug delivery device may be employed. Oral, rectal, or topical administration may be important for prophylactic or long-term treatment. Preferred rectal modes of delivery include administration as a suppository or enema wash.

The pharmaceutical preparations may conveniently be presented in unit dosage form and may be prepared by any of the methods well known in the art of pharmacy. All methods include the step of bringing the compounds of the invention into association with a carrier which constitutes one or more accessory ingredients. In general, the compositions are prepared by uniformly and intimately bringing the compounds of the invention into association with a liquid carrier, a finely divided solid carrier, or both, and then, if necessary, shaping the product.

When administered, the pharmaceutical preparations of the invention are applied in pharmaceutically acceptable compositions. Such preparations may routinely contain salts, buffering agents, preservatives, compatible carriers, lubricants, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, succinic, naphthalene-2-sulfonic, pamoic, 3-hydroxy-2-naphthalenecarboxylic, and benzene sulfonic.

It should be understood that when referring to MNTX, R- and S-MNTX, and therapeutic agent(s) of the invention, it is meant to encompass salts of the same. Such salts are of a variety well known to those or ordinary skill in the art. When used in pharmaceutical preparations, the salts preferably are pharmaceutically-acceptable for use in humans. Bromide is an example of one such salt.

The pharmaceutical preparations of the present invention may include or be diluted into a pharmaceutically-acceptable carrier. The term "pharmaceutically-acceptable carrier" as used herein means one or more compatible solid or liquid fillers, diluents or encapsulating substances which are suitable for administration to a human or other mammal such as non-human primate, a dog, cat, horse, cow, sheep, pig, or goat. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carrier formulations suitable for oral administration, for suppositories, and for parenteral administration, etc., can be found in Remington's Pharmaceutical Sciences, Mack Publishing Company, Easton, Pa.

Aqueous formulations may include a chelating agent, a buffering agent, an anti-oxidant and, optionally, an isotonicity agent, preferably pH adjusted to between 3.0 and 3.5. Examples of such formulations that are stable to autoclaving and long term storage are described in co-pending U.S. application Ser. No. 10/821,811, entitled "Pharmaceutical Formulation."

Chelating agents include, for example, ethylenediaminetetraacetic acid (EDTA) and derivatives thereof, citric acid and derivatives thereof, niacinamide and derivatives thereof, sodium desoxycholate and derivatives thereof, and L-glutamic acid, N,N-diacetic acid and derivatives thereof.

Buffering agents include those selected from the group consisting of citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate and benzoic acid, or combinations thereof.

Antioxidants include those selected from the group consisting of an ascorbic acid derivative, butylated hydroxy anisole, butylated hydroxy toluene, alkyl gallate, sodium meta-bisulfite, sodium bisulfite, sodium dithionite, sodium thioglycollate acid, sodium formaldehyde sulfoxylate, tocopheral and derivatives thereof, monothioglycerol, and sodium sulfite. The preferred antioxidant is monothioglycerol.

Isotonicity agents include those selected from the group consisting of sodium chloride, mannitol, lactose, dextrose, glycerol, and sorbitol.

Preservatives that can be used with the present compositions include benzyl alcohol, parabens, thimerosal, chlorobutanol and preferably benzalkonium chloride. Typically, the preservative will be present in a composition in a concentration of up to about 2% by weight. The exact concentration of the preservative, however, will vary depending upon the intended use and can be easily ascertained by one skilled in the art.

The compounds of the invention can be prepared in lyophilized compositions, preferably in the presence of a cryoprotecting agent such as mannitol, or lactose, sucrose, polyethylene glycol, and polyvinyl pyrrolidines. Cryoprotecting agents which result in a reconstitution pH of 6.0 or less are preferred. The invention therefore provides a lyophilized preparation of therapeutic agent(s) of the invention. The preparation can contain a cryoprotecting agent, such as mannitol or lactose, which is preferably neutral or acidic in water.

Oral, parenteral and suppository formulations of agents are well known and commercially available. The therapeutic agent(s) of the invention can be added to such well known formulations. It can be mixed together in solution or semi-solid solution in such formulations, can be provided in a suspension within such formulations or could be contained in particles within such formulations.

A product containing therapeutic agent(s) of the invention and, optionally, one or more other active agents can be configured as an oral dosage. The oral dosage may be a liquid, a semisolid or a solid. An opioid may optionally be included in the oral dosage. The oral dosage may be configured to release the therapeutic agent(s) of the invention before, after or simultaneously with the other agent (and/or the opioid). The oral dosage may be configured to have the therapeutic agent(s) of the invention and the other agents release completely in the stomach, release partially in the stomach and partially in the intestine, in the intestine, in the colon, partially in the stomach, or wholly in the colon. The oral dosage also may be configured whereby the release of the therapeutic agent(s) of the invention is confined to the stomach or intestine while the release of the other active agent is not so confined or is confined differently from the therapeutic agent(s) of the invention. For example, the therapeutic agent(s) of the invention may be an enterically coated core or pellets contained within a pill or capsule that releases the other agent first and releases the therapeutic agent(s) of the invention only after the therapeutic agent(s) of the invention passes through the stomach and into the intestine. The therapeutic agent(s) of the invention also can be in a sustained release material, whereby the therapeutic agent(s) of the invention is released throughout the gastrointestinal tract and the other agent is released on the same or a different schedule. The same objective for therapeutic agent(s) of the invention release can be achieved with immediate release of therapeutic agent(s) of the invention combined with enteric coated therapeutic agent(s) of the invention. In these instances, the other agent could be released immediately in the stomach, throughout the gastrointestinal tract or only in the intestine.

The materials useful for achieving these different release profiles are well known to those of ordinary skill in the art Immediate release is obtainable by conventional tablets with binders which dissolve in the stomach. Coatings which dissolve at the pH of the stomach or which dissolve at elevated temperatures will achieve the same purpose. Release only in the intestine is achieved using conventional enteric coatings such as pH sensitive coatings which dissolve in the pH environment of the intestine (but not the stomach) or coatings which dissolve over time. Release throughout the gastrointestinal tract is achieved by using sustained-release materials and/or combinations of the immediate release systems and sustained and/or delayed intentional release systems (e.g., pellets which dissolve at different pHs).

In the event that it is desirable to release the therapeutic agent(s) of the invention first, the therapeutic agent(s) of the invention could be coated on the surface of the controlled release formulation in any pharmaceutically acceptable carrier suitable for such coatings and for permitting the release of the therapeutic agent(s) of the invention, such as in a temperature sensitive pharmaceutically acceptable carrier used for controlled release routinely. Other coatings which dissolve when placed in the body are well known to those of ordinary skill in the art.

The therapeutic agent(s) of the invention also may be mixed throughout a controlled release formulation, whereby it is released before, after or simultaneously with another agent. The therapeutic agent(s) of the invention may be free, that is, solubilized within the material of the formulation. The therapeutic agent(s) of the invention also may be in the form of vesicles, such as wax coated micropellets dispersed throughout the material of the formulation. The coated pellets can be fashioned to immediately release the therapeutic agent(s) of the invention based on temperature, pH or the like. The pellets also can be configured so as to delay the release of the therapeutic agent(s) of the invention, allowing the other agent a period of time to act before the therapeutic agent(s) of the invention exerts its effects. The therapeutic agent(s) of the invention pellets also can be configured to release the therapeutic agent(s) of the invention in virtually any sustained release pattern, including patterns exhibiting first order release kinetics or sigmoidal order release kinetics using materials of the prior art and well known to those of ordinary skill in the art.

The therapeutic agent(s) of the invention also can be contained within a core within the controlled release formulation. The core may have any one or any combination of the properties described above in connection with the pellets. The therapeutic agent(s) of the invention may be, for example, in a core coated with a material, dispersed throughout a material, coated onto a material or adsorbed into or throughout a material.

It should be understood that the pellets or core may be of virtually any type. They may be drug coated with a release material, drug interspersed throughout material, drug adsorbed into a material, and so on. The material may be erodible or nonerodible.

The therapeutic agent(s) of the invention, may be provided in particles. Particles as used herein means nano or microparticles (or in some instances larger) which can consist in whole or in part of the therapeutic agent(s) of the inventions or the other agents as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the antagonist in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as nonimmediate release formulations, with nonimmediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release." These formulations may be for any mode of administration.

Delivery systems specific for the gastrointestinal tract are roughly divided into three types: the first is a delayed release system designed to release a drug in response to, for example, a change in pH; the second is a timed-release system designed to release a drug after a predetermined time; and the third is a microflora enzyme system making use of the abundant enterobacteria in the lower part of the gastrointestinal tract (e.g., in a colonic site-directed release formulation).

An example of a delayed release system is one that uses, for example, an acrylic or cellulosic coating material and dissolves on pH change. Because of ease of preparation, many reports on such "enteric coatings" have been made. In general, an enteric coating is one which passes through the stomach without releasing substantial amounts of drug in the stomach (i.e., less than 10% release, 5% release and even 1% release in the stomach) and sufficiently disintegrating in the intestinal tract (by contact with approximately neutral or alkaline intestine juices) to allow the transport (active or passive) of the active agent through the walls of the intestinal tract.

Various in vitro tests for determining whether or not a coating is classified as an enteric coating have been published in the pharmacopoeia of various countries. A coating which remains intact for at least 2 hours, in contact with artificial gastric juices such as HCl of pH 1 at 36 to 38° C. and thereafter disintegrates within 30 minutes in artificial intestinal juices such as a $KH_2PO_4$ buffered solution of pH 6.8 is one example. One such well known system is EUDRAGIT material, commercially available and reported on by Behringer, Manchester University, Saale Co., and the like. Enteric coatings are discussed further, below.

A timed release system is represented by Time Erosion System (TES) by Fujisawa Pharmaceutical Co., Ltd. and Pulsincap by R. P. Scherer. According to these systems, the site of drug release is decided by the time of transit of a preparation in the gastrointestinal tract. Since the transit of a preparation in the gastrointestinal tract is largely influenced by the gastric emptying time, some time release systems are also enterically coated.

Systems making use of the enterobacteria can be classified into those utilizing degradation of azoaromatic polymers by an azo reductase produced from enterobacteria as reported by the group of Ohio University (M. Saffran, et al., Science, Vol. 233: 1081 (1986)) and the group of Utah University (J. Kopecek, et al., Pharmaceutical Research, 9(12), 1540-1545 (1992)); and those utilizing degradation of polysaccharides by beta-galactosidase of enterobacteria as reported by the group of Hebrew University (unexamined published Japanese patent application No. 5-50863 based on a PCT application) and the group of Freiberg University (K. H. Bauer et al., Pharmaceutical Research, 10(10), 5218 (1993)). In addition, the system using chitosan degradable by chitosanase by Teikoku Seiyaku K. K. (unexamined published Japanese patent application No. 4-217924 and unexamined published Japanese patent application No. 4-225922) is also included.

The enteric coating is typically, although not necessarily, a polymeric material. Preferred enteric coating materials comprise bioerodible, gradually hydrolyzable and/or gradually water-soluble polymers. The "coating weight," or relative amount of coating material per capsule, generally dictates the time interval between ingestion and drug release. Any coating should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention. The selection of the specific enteric coating material will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; ease of application as a coating (substrate friendly); and economical practicality.

Suitable enteric coating materials include, but are not limited to: cellulosic polymers such as cellulose acetate phthalate, cellulose acetate trimellitate, hydroxypropylmethyl cellulose phthalate, hydroxypropyhmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl methacrylate (e.g., those copolymers sold under the trade name EUDRAGIT); vinyl polymers and copolymers such as polyvinyl acetate, polyvinylacetate phthalate, vinylacetate crotonic acid copolymer, and ethylene-vinyl acetate copolymers; and shellac (purified lac). Combinations of different coating materials may also be used. Well known enteric coating material for use herein are those acrylic acid polymers and copolymers available under the trade name EUDRAGIT from Rohm Pharma (Germany). The EUDRAGIT series E, L, S, RL, RS and NE copolymers are available as solubilized in organic solvent, as an aqueous dispersion, or as a dry powder. The EUDRAGIT series RL, NE, and RS copolymers are insoluble in the gastrointestinal tract but are permeable and are used primarily for extended release. The EUDRAGIT series E copolymers dissolve in the stomach. The EUDRAGIT series L, L-30D and S copolymers are insoluble in stomach and dissolve in the intestine, and are thus most preferred herein.

A particular methacrylic copolymer is EUDRAGIT L, particularly L-30D and EUDRAGIT L 100-55. In EUDRAGIT L-30D, the ratio of free carboxyl groups to ester groups is approximately 1:1. Further, the copolymer is known to be insoluble in gastrointestinal fluids having pH below 5.5, generally 1.5-5.5, i.e., the pH generally present in the fluid of the upper gastrointestinal tract, but readily soluble or partially soluble at pH above 5.5, i.e., the pH generally present in the fluid of lower gastrointestinal tract. Another particular methacrylic acid polymer is EUDRAGIT S, which differs from EUDRAGIT L-30D in that the ratio of free carboxyl groups to ester groups is approximately 1:2. EUDRAGIT S is insoluble at pH below 5.5, but unlike EUDRAGIT L-30D, is poorly soluble in gastrointestinal fluids having a pH in the range of 5.5 to 7.0, such as in the small intestine. This copolymer is soluble at pH 7.0 and above, i.e., the pH generally found in the colon. EUDRAGIT S can be used alone as a coating to provide drug delivery in the large intestine. Alternatively, EUDRAGIT S, being poorly soluble in intestinal fluids below pH 7, can be used in combination with EUDRAGIT L-30D, soluble in intestinal fluids above pH 5.5, in order to provide a delayed release composition which can be formulated to deliver the active agent to various segments of the intestinal tract. The more EUDRAGIT L-30D used, the more proximal release and delivery begins, and the more EUDRAGIT S used, the more distal release and delivery begins. It will be appreciated by those skilled in the art that both EUDRAGIT L-30D and EUDRAGIT S can be replaced with other pharmaceutically acceptable polymers having similar pH solubility characteristics. In certain embodiments of the invention, the preferred enteric coating is ACRYL-EZE™ (methacrylic acid co-polymer type C; Colorcon, West Point, Pa.).

The enteric coating provides for controlled release of the active agent, such that drug release can be accomplished at some generally predictable location. The enteric coating also prevents exposure of the therapeutic agent and carrier to the epithelial and mucosal tissue of the buccal cavity, pharynx, esophagus, and stomach, and to the enzymes associated with these tissues. The enteric coating therefore helps to protect the active agent, carrier and a patient's internal tissue from any adverse event prior to drug release at the desired site of delivery. Furthermore, the coated material of the present invention allows optimization of drug absorption, active agent protection, and safety. Multiple enteric coatings targeted to release the active agent at various regions in the gastrointestinal tract would enable even more effective and sustained improved delivery throughout the gastrointestinal tract.

The coating can, and usually does, contain a plasticizer to prevent the formation of pores and cracks that would permit the penetration of the gastric fluids. Suitable plasticizers include, but are not limited to, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating comprised of an anionic carboxylic acrylic polymer will usually contain approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The coating can be applied to particles of the therapeutic agent(s), tablets of the therapeutic agent(s), capsules containing the therapeutic agent(s) and the like, using conventional coating methods and equipment. For example, an enteric coating can be applied to a capsule using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6th Ed. (Media, Pa.: Williams & Wilkins, 1995). The coating thickness, as noted above, must be sufficient to ensure that the oral dosage form remains intact until the desired site of topical delivery in the lower intestinal tract is reached.

In another embodiment, drug dosage forms are provided that comprise an enterically coated, osmotically activated device housing a formulation of the invention. In this embodiment, the drug-containing formulation is encapsulated in a semipermeable membrane or barrier containing a small orifice. As known in the art with respect to so-called "osmotic pump" drug delivery devices, the semipermeable membrane allows passage of water in either direction, but not drug. Therefore, when the device is exposed to aqueous fluids, water will flow into the device due to the osmotic pressure differential between the interior and exterior of the device. As water flows into the device, the drug-containing formulation in the interior will be "pumped" out through the orifice. The rate of drug release will be equivalent to the inflow rate of water times the drug concentration. The rate of water influx and drug efflux can be controlled by the composition and size of the orifice of the device. Suitable materials for the semipermeable membrane include, but are not limited to, polyvinyl alcohol, polyvinyl chloride, semipermeable polyethylene glycols, semipermeable polyurethanes, semipermeable polyamides, semipermeable sulfonated polystyrenes and polystyrene derivatives; semipermeable poly(sodium styrenesulfonate), semipermeable poly(vinylbenzyltrimethylammonium chloride), and cellulosic polymers such as cellulose acetate, cellulose diacetate, cellulose triacetate, cellulose propionate, cellulose acetate propionate, cellulose acetate butyrate, cellulose trivalerate, cellulose trilmate, cellulose tripalmitate, cellulose trioctanoate, cellulose tripropionate, cellulose disuccinate, cellulose dipalmitate, cellulose dicylate, cellulose acetate succinate, cellulose propionate succinate, cellulose acetate octanoate, cellulose valerate palmitate, cellulose acetate heptanate, cellulose acetaldehyde dimethyl acetal, cellulose acetate ethylcarbamate, cellulose acetate methylcarbamate, cellulose dimethylaminoacetate and ethylcellulose.

In another embodiment, drug dosage forms are provided that comprise a sustained release coated device housing a formulation of the invention. In this embodiment, the drug-containing formulation is encapsulated in a sustained release membrane or film. The membrane may be semipermeable, as described above. A semipermeable membrane allows for the passage of water inside the coated device to dissolve the drug. The dissolved drug solution diffuses out through the semipermeable membrane. The rate of drug release depends upon the thickness of the coated film and the release of drug can begin in any part of the GI tract. Suitable membrane materials for such a membrane include ethylcellulose.

In another embodiment, drug dosage forms are provided that comprise a sustained release device housing a formulation of the invention. In this embodiment, the drug-containing formulation is uniformly mixed with a sustained release polymer. These sustained release polymers are high molecular weight water-soluble polymers, which when in contact with water, swell and create channels for water to diffuse inside and dissolve the drug. As the polymers swell and dissolve in water, more of drug is exposed to water for dissolution. Such a system is generally referred to as sustained release matrix. Suitable materials for such a device include hydropropyl methylcellulose, hydroxypropyl cellulose, hydroxyethyl cellulose and methyl cellulose.

In another embodiment, drug dosage forms are provided that comprise an enteric coated device housing a sustained release formulation of the invention. In this embodiment, the drug containing product described above is coated with an enteric polymer. Such a device would not release any drug in the stomach and when the device reaches the intestine, the enteric polymer is first dissolved and only then would the drug release begin. The drug release would take place in a sustained release fashion.

Enterically coated, osmotically activated devices can be manufactured using conventional materials, methods and equipment. For example, osmotically activated devices may be made by first encapsulating, in a pharmaceutically acceptable soft capsule, a liquid or semi-solid formulation of the compounds of the invention as described previously. This interior capsule is then coated with a semipermeable membrane composition (comprising, for example, cellulose acetate and polyethylene glycol 4000 in a suitable solvent such as a methylene chloride-methanol admixture), for example using an air suspension machine, until a sufficiently thick laminate is formed, e.g., around 0.05 mm. The semipermeable laminated capsule is then dried using conventional techniques. Then, an orifice having a desired diameter (e.g., about 0.99 mm) is provided through the semipermeable laminated capsule wall, using, for example, mechanical drilling, laser drilling, mechanical rupturing, or erosion of an erodible element such as a gelatin plug. The osmotically activated device may then be enterically coated as previously described. For osmotically activated devices containing a solid carrier rather than a liquid or semi-solid carrier, the interior capsule is optional; that is, the semipermeable membrane may be formed directly around the carrier-drug composition. However, preferred carriers for use in the drug-containing formulation of the osmotically activated device are solutions, suspensions, liquids, immiscible liquids, emulsions, sols, colloids, and oils. Particularly preferred carriers include, but are not limited to, those used for enterically coated capsules containing liquid or semisolid drug formulations.

Cellulose coatings include those of cellulose acetate phthalate and trimellitate; methacrylic acid copolymers, e.g. copolymers derived from methylacrylic acid and esters thereof, containing at least 40% methylacrylic acid; and especially hydroxypropyl methylcellulose phthalate. Methylacrylates include those of molecular weight above 100,000 daltons based on, e.g. methylacrylate and methyl or ethyl methylacrylate in a ratio of about 1:1. Typical products include Endragit L, e.g. L 100-55, marketed by Rohm GmbH, Darmstadt, Germany. Typical cellulose acetate phthalates have an acetyl content of 17-26% and a phthalate content of from 30-40% with a viscosity of ca. 45-90 cP. Typical cellulose acetate trimellitates have an acetyl content of 17-26%, a trimellityl content from 25-35% with a viscosity of ca. 15-20 cS. An example of a cellulose acetate trimellitate is the marketed product CAT (Eastman Kodak Company, USA). Hydroxypropyl methylcellulose phthalates typically have a molecular weight of from 20,000 to 130,000 daltons, a hydroxypropyl content of from 5 to 10%, a methoxy content of from 18 to 24% and a phthalyl content from 21 to 35%. An example of a cellulose acetate phthalate is the marketed product CAP (Eastman Kodak, Rochester N.Y., USA). Examples of hydroxypropyl methylcellulose phthalates are the marketed products having a hydroxypropyl content of from 6-10%, a methoxy content of from 20-24%, a phthalyl content of from 21-27%, a molecular weight of about 84,000 daltons, sold under the trademark HP50 and available from Shin-Etsu Chemical Co. Ltd., Tokyo, Japan, and having a hydroxypropyl content, a methoxyl content, and a phthalyl content of 5-9%, 18-22% and 27-35%, respectively, and a molecular weight of 78,000 daltons, known under the trademark HP55 and available from the same supplier.

The therapeutic agents may be provided in capsules, coated or not. The capsule material may be either hard or soft, and as will be appreciated by those skilled in the art, typically comprises a tasteless, easily administered and water soluble compound such as gelatin, starch or a cellulosic material. The capsules are preferably sealed, such as with gelatin bands or the like. See, for example, Remington: The Science and Practice of Pharmacy, Nineteenth Edition (Easton, Pa.: Mack Publishing Co., 1995), which describes materials and methods for preparing encapsulated pharmaceuticals.

A product containing therapeutic agent(s) of the invention can be configured as a suppository. The therapeutic agent(s) of the invention can be placed anywhere within or on the suppository to favorably affect the relative release of the therapeutic agent(s). The nature of the release can be zero order, first order, or sigmoidal, as desired.

Suppositories are solid dosage forms of medicine intended for administration via the rectum. Suppositories are compounded so as to melt, soften, or dissolve in the body cavity (around 98.6° F.) thereby releasing the medication contained therein. Suppository bases should be stable, non-irritating, chemically inert, and physiologically inert. Many commercially available suppositories contain oily or fatty base materials, such as cocoa butter, coconut oil, palm kernel oil, and palm oil, which often melt or deform at room temperature necessitating cool storage or other storage limitations. U.S. Pat. No. 4,837,214 to Tanaka et al. describes a suppository base comprised of 80 to 99 percent by weight of a lauric-type fat having a hydroxyl value of 20 or smaller and containing glycerides of fatty acids having 8 to 18 carbon atoms combined with 1 to 20 percent by weight diglycerides of fatty acids (which erucic acid is an example of). The shelf life of these type of suppositories is limited due to degradation. Other suppository bases contain alcohols, surfactants, and the like which raise the melting temperature but also can lead to poor absorption of the medicine and side effects due to irritation of the local mucous membranes (see for example, U.S. Pat. No. 6,099,853 to Hartelendy et al., U.S. Pat. No. 4,999,342 to Ahmad et al., and U.S. Pat. No. 4,765,978 to Abidi et al.).

The base used in the pharmaceutical suppository composition of this invention includes, in general, oils and fats comprising triglycerides as main components such as cacao butter, palm fat, palm kernel oil, coconut oil, fractionated coconut oil, lard and WITEPSOL®, waxes such as lanolin and reduced lanolin; hydrocarbons such as VASELINE®, squalene, squalane and liquid paraffin; long to medium chain fatty acids such as caprylic acid, lauric acid, stearic acid and oleic acid; higher alcohols such as lauryl alcohol, cetanol and stearyl alcohol; fatty acid esters such as butyl stearate and dilauryl malonate; medium to long chain carboxylic acid esters of glycerin such as triolein and tristearin; glycerin-substituted carboxylic acid esters such as glycerin acetoacetate; and polyethylene glycols and its derivatives such as macrogols and cetomacrogol. They may be used either singly or in combination of two or more. If desired, the composition of this invention may further include a surface-active agent, a coloring agent, etc., which are ordinarily used in suppositories.

The pharmaceutical composition of this invention may be prepared by uniformly mixing predetermined amounts of the active ingredient, the absorption aid and optionally the base, etc. in a stirrer or a grinding mill, if required at an elevated temperature. The resulting composition, may be formed into a suppository in unit dosage form by, for example, casting the mixture in a mold, or by forming it into a gelatin capsule using a capsule filling machine.

The compositions according to the present invention also can be administered as a nasal spray, nasal drop, suspension, gel, ointment, cream or powder. The administration of a composition can also include using a nasal tampon or a nasal sponge containing a composition of the present invention.

The nasal delivery systems that can be used with the present invention can take various forms including aqueous preparations, non-aqueous preparations and combinations thereof. Aqueous preparations include, for example, aqueous gels, aqueous suspensions, aqueous liposomal dispersions, aqueous emulsions, aqueous microemulsions and combinations thereof. Non-aqueous preparations include, for example, non-aqueous gels, non-aqueous suspensions, non-aqueous liposomal dispersions, non-aqueous emulsions, non-aqueous microemulsions and combinations thereof. The various forms of the nasal delivery systems can include a buffer to maintain pH, a pharmaceutically acceptable thickening agent and a humectant. The pH of the buffer can be selected to optimize the absorption of the therapeutic agent(s) across the nasal mucosa.

With respect to the non-aqueous nasal formulations, suitable forms of buffering agents can be selected such that when the formulation is delivered into the nasal cavity of a mammal, selected pH ranges are achieved therein upon contact with, e.g., a nasal mucosa. In the present invention, the pH of the compositions should be maintained from about 2.0 to about 6.0. It is desirable that the pH of the compositions is one which does not cause significant irritation to the nasal mucosa of a recipient upon administration.

The viscosity of the compositions of the present invention can be maintained at a desired level using a pharmaceutically acceptable thickening agent. Thickening agents that can be used in accordance with the present invention include methyl cellulose, xanthan gum, carboxymethyl cellulose, hydroxypropyl cellulose, carbomer, polyvinyl alcohol, alginates, acacia, chitosans and combinations thereof. The concentration of the thickening agent will depend upon the agent selected and the viscosity desired. Such agents can also be used in a powder formulation discussed above.

The compositions of the present invention can also include a humectant to reduce or prevent drying of the mucus membrane and to prevent irritation thereof. Suitable humectants that can be used in the present invention include sorbitol, mineral oil, vegetable oil and glycerol; soothing agents; membrane conditioners; sweeteners; and combinations thereof. The concentration of the humectant in the present compositions will vary depending upon the agent selected.

One or more therapeutic agents may be incorporated into the nasal delivery system or any other delivery system described herein.

A composition formulated for topical administration may be liquid or semi-solid (including, for example, a gel, lotion, emulsion, cream, ointment, spray or aerosol) or may be provided in combination with a "finite" carrier, for example, a non-spreading material that retains its form, including, for example, a patch, bioadhesive, dressing or bandage. It may be aqueous or non-aqueous; it may be formulated as a solution, emulsion, dispersion, a suspension or any other mixture.

Important modes of administration include topical application to the skin, eyes or mucosa. Thus, typical vehicles are those suitable for pharmaceutical or cosmetic application to body surfaces. The compositions provided herein may be applied topically or locally to various areas in the body of a patient. As noted above, topical application is intended to refer to application to the tissue of an accessible body surface, such as, for example, the skin (the outer integument or covering) and the mucosa (the mucous-producing, secreting and/or containing surfaces). Exemplary mucosal surfaces include the mucosal surfaces of the eyes, mouth (such as the lips, tongue, gums, cheeks, sublingual and roof of the mouth), larynx, esophagus, bronchial, nasal passages, vagina and rectum/anus; in some embodiments, preferably the mouth, larynx, esophagus, vagina and rectum/anus; in other embodiments, preferably the eyes, larynx, esophagus, bronchial, nasal passages, and vagina and rectum/anus. As noted above, local application herein refers to application to a discrete internal area of the body, such as, for example, a joint, soft tissue area (such as muscle, tendon, ligaments, intraocular or other fleshy internal areas), or other internal area of the body. Thus, as used herein, local application refers to applications to discrete areas of the body.

With respect to topical and/or local administration of the present compositions, desirable efficacy may involve, for example, penetration of therapeutic agent(s) of the invention into the skin and/or tissue to substantially reach a hyperalgesic site to provide desirable anti-hyperalgesic pain relief. The efficacy of the present compositions may be about the same as that achieved, for example, with central opiate analgesics. But, as discussed in detail herein, the efficacy achieved with therapeutic agent(s) of the invention is preferably obtained without the undesirable effects that are typically associated with central opiates including, for example, respiratory depression, sedation, and addiction, as it is believed that therapeutic agent(s) of the invention does not cross the blood brain barrier.

Also in certain preferred embodiments, including embodiments that involve aqueous vehicles, the compositions may also contain a glycol, that is, a compound containing two or more hydroxy groups. A glycol which is particularly preferred for use in the compositions is propylene glycol. In these preferred embodiments, the glycol is preferably included in the compositions in a concentration of from greater than 0 to about 5 wt. %, based on the total weight of the composition. More preferably, the compositions contain from about 0.1 to less than about 5 wt. % of a glycol, with from about 0.5 to about 2 wt. % being even more preferred. Still more preferably, the compositions contain about 1 wt. % of a glycol.

For local internal administration, such as intra-articular administration, the compositions are preferably formulated as a solution or a suspension in an aqueous-based medium, such as isotonically buffered saline or are combined with a biocompatible support or bioadhesive intended for internal administration.

Lotions, which, for example, may be in the form of a suspension, dispersion or emulsion, contain an effective concentration of one or more of the compounds. The effective concentration is preferably to deliver an effective amount, typically at a concentration of between about 0.1-50% [by weight] or more of one or more of the compounds provided herein. The lotions also contain [by weight] from 1% to 50% of an emollient and the balance water, a suitable buffer, and other agents as described above. Any emollients known to those of skill in the art as suitable for application to human skin may be used. These include, but are not limited to, the following: (a) Hydrocarbon oils and waxes, including mineral oil, petrolatum, paraffin, ceresin, ozokerite, microcrystalline wax, polyethylene, and perhydrosqualene. b) Silicone oils, including dimethylpolysiloxanes, methylphenylpolysiloxanes, water-soluble and alcohol-soluble silicone-glycol copolymers. (c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil, and soybean oil. (d) Acetoglyceride esters, such as acetylated monoglycerides. (e) Ethoxylated glycerides, such as ethoxylated glyceryl monstearate. (f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. (g) Alkenyl esters of fatty acids having 10 to 20 carbon atoms. Examples thereof include, but are not limited to, oleyl myristate, oleyl stearate, and oleyl oleate. (h) Fatty acids having 9 to 22 carbon atoms. Suitable examples include, but are not limited to, pelargonic, lauric, myristic, palmitic, stearic, isostearic, hydroxystearic, oleic, linoleic, ricinoleic, arachidonic, behenic, and erucic acids. (i) Fatty alcohols having 10 to 22 carbon atoms, such as, but not limited to, lauryl, myristyl, cetyl, hexadecyl, stearyl, isostearyl, hydroxystearyl, oleyl, ricinoleyl, behenyl, erucyl, and 2-octyl dodecyl alcohols. (j) Fatty alcohol ethers, including, but not limited to ethoxylated fatty alcohols of 10 to 20 carbon atoms, such as, but are not limited to, the lauryl, cetyl, stearyl, isostearyl, oleyl, and cholesterol alcohols having attached thereto from 1 to 50 ethylene oxide groups or 1 to 50 propylene oxide groups or mixtures thereof. (k) Ether-esters, such as fatty acid esters of ethoxylated fatty alcohols. (1) Lanolin and derivatives, including, but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases. (m) polyhydric alcohols and polyether derivatives, including, but not limited to, propylene glycol, dipropylene glycol, polypropylene glycol [M.W. 2000-4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200-6000], methoxy polyethylene glycols 350, 550, 750, 2000, 5000, poly(ethylene oxide) homopolymers [M.W. 100,000-5,000,000], polyalkylene glycols and derivatives, hexylene glycol (2-methyl-2,4-pentanediol), 1,3-butylene glycol, 1,2,6,-hexanetriol, etho-hexadiol USP (2-ethyl-1,3-hexanediol), $C_{15}$-$C_{18}$ vicinal glycol and polyoxypropylene derivatives of trimethylolpropane. (n) polyhydric alcohol esters, including, but not limited to, ethylene glycol mono- and di-fatty acid esters, diethylene glycol mono and di-fatty acid esters, polyethylene glycol [M.W. 200-6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters. (o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters. (p) Vegetable waxes, including, but not limited to, carnauba and candelilla waxes. (q) phospholipids, such as lecithin and derivatives. (r) Sterols, including, but not limited to, cholesterol and cholesterol fatty acid esters. (s) Amides, such as fatty acid amides, ethoxylated fatty acid amides, and solid fatty acid alkanolamides.

The lotions further preferably contain [by weight] from 1% to 10%, more preferably from 2% to 5%, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol where the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g., sodium, potassium and triethanolamine soaps, where the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound, such as loperamide, is dissolved, suspended or otherwise uniformly dispersed in the mixture.

Other conventional components of such lotions may be included. One such additive is a thickening agent at a level from 1% to 10% by weight of the composition. Examples of suitable thickening agents include, but are not limited to: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

Creams can be formulated to contain a concentration effective to deliver an effective amount of therapeutic agent(s) of the invention to the treated tissue, typically at between about 0.1%, preferably at greater than 1% up to and greater than 50%, preferably between about 3% and 50%, more preferably between about 5% and 15% therapeutic agent(s) of the invention. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included in the composition at a level from 3% to 50%, preferably from 5% to 20%.

These compositions that are formulated as solutions or suspensions may be applied to the skin, or, may be formulated as an aerosol or foam and applied to the skin as a spray-on. The aerosol compositions typically contain [by weight] from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspensions may also be topically applied to the eyes and mucosa. Solutions, particularly those intended for ophthalmic use, may be formulated as 0.01%-10% isotonic solutions, pH about 5-7, with appropriate salts, and preferably containing one or more of the compounds herein at a concentration of about 0.1%, preferably greater than 1%, up to 50% or more. Suitable ophthalmic solutions are known [see, e.g., U.S. Pat. No. 5,116,868, which describes typical compositions of ophthalmic irrigation solutions and solutions for topical application]. Such solutions, which have a pH adjusted to about 7.4, contain, for example, 90-100 mM sodium chloride, 4-6 mM dibasic potassium phosphate, 4-6 mM dibasic sodium phosphate, 8-12 mM sodium citrate, 0.5-1.5 mM magnesium chloride, 1.5-2.5 mM calcium chloride, 15-25 mM sodium acetate, 10-20 mM D.L.-sodium, .β.-hydroxybutyrate and 5-5.5 mM glucose.

Gel compositions can be formulated by simply admixing a suitable thickening agent to the previously described solution or suspension compositions. Examples of suitable thickening agents have been previously described with respect to the lotions.

The gelled compositions contain an effective amount of therapeutic agent(s) of the invention, typically at a concentration of between about 0.1-50% by weight or more of one or more of the compounds provided herein; from 5% to 75%, preferably from 10% to 50%, of an organic solvent as previously described; from 0.5% to 20%, preferably from 1% to 10% of the thickening agent; the balance being water or other aqueous or non-aqueous carrier, such as, for example, an organic liquid, or a mixture of carriers.

The formulations can be constructed and arranged to create steady state plasma levels. Steady state plasma concentrations can be measured using HPLC techniques, as are known to those of skill in the art. Steady state is achieved when the rate of drug availability is equal to the rate of drug elimination from the circulation. In typical therapeutic settings, the therapeutic agent(s) of the invention will be administered to patients either on a periodic dosing regimen or with a constant infusion regimen. The concentration of drug in the plasma will tend to rise immediately after the onset of administration and will tend to fall over time as the drug is eliminated from the circulation by means of distribution into cells and tissues, by metabolism, or by excretion. Steady state will be obtained when the mean drug concentration remains constant over time. In the case of intermittent dosing, the pattern of the drug concentration cycle is repeated identically in each interval between doses with the mean concentration remaining constant. In the case of constant infusion, the mean drug concentration will remain constant with very little oscillation. The achievement of steady state is determined by means of measuring the concentration of drug in plasma over at least one cycle of dosing such that one can verify that the cycle is being repeated identically from dose to dose. Typically, in an intermittent dosing regimen, maintenance of steady state can be verified by determining drug concentrations at the consecutive troughs of a cycle, just prior to administration of another dose. In a constant infusion regimen where oscillation in the concentration is low, steady state can be verified by any two consecutive measurements of drug concentration.

Figure 8:
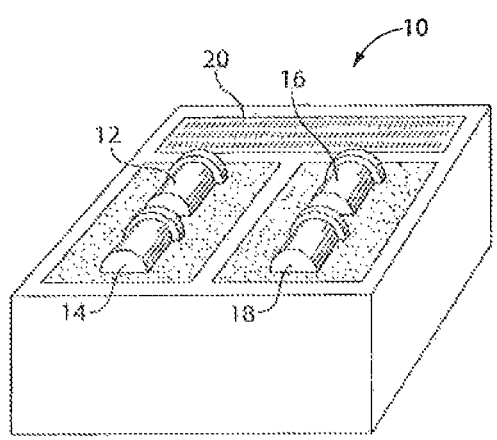
FIG. 8 shows a kit according to the invention.

FIG. 8 shows a kit according to the invention. The kit 10 includes a vial 12 containing an opioid tablet. The kit 10 also includes a vial 14 containing R-MNTX tablets which contain pellets, some of which are enterically coated with pH sensitive material and some of which are constructed and arranged to release the R-MNTX immediately in the stomach. The kit also includes instructions 20 for administering the tablets to a subject who is constipated or who has symptoms of constipation or gastrointestinal immotility. The instructions include indicia, for example writing, indicating that the R-MNTX is pure R-MNTX free of S-MNTX.

In some aspects of the invention, the kit 10 can include optimally or alternatively a pharmaceutical preparation vial 16, and a pharmaceutical preparation diluents vial 18. The vial containing the diluents for the pharmaceutical preparation is optional. The diluents vial contains diluents such as physiological saline for diluting what could be a concentrated solution or lyophilized powder of R-MNTX. The instructions can include instructions for mixing a particular amount of the diluents with a particular amount of the concentrated pharmaceutical preparation, whereby a final formulation for injection or infusion is prepared. The instructions 20 can include instructions for treating a patient with an effective amount of R-MNTX. It also will be understood that the containers containing the preparations, whether the container is a bottle, a vial with a septum, an ampoule with a septum, an infusion bag, and the like, can contain additional indicia such as conventional markings which change color when the preparation has been autoclaved or otherwise sterilized.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

EXAMPLES

Example 1

HPLC Analysis of R- and S-MNTX

HPLC analysis was performed on a Varian ProStar HPLC controlled by Varian Star software using the following method:
HPLC Method I:
Column: Luna C18(2), 150×4.6 mm, 5μ
Flow Rate: 1 mL/min
Detection: UV @ 230 nm
Gradient Program:

| Time (min) | % A | % B |
|---|---|---|
| 0:00 | 95 | 5 |
| 8:00 | 65 | 35 |
| 12:00 | 35 | 65 |
| 15:00 | 0 | 100 |
| 16:00 | 95 | 5 |
| 18:00 | 95 | 5 |

Mobile phase A=0.1% Aqueous TFA
Mobile phase B=0.1% Methanolic TFA
TFA=trifluoroacetic acid
HPLC Method II:
Chromatographic Conditions and Parameters: Analytical Column Description: Phenomenex Inertsil ODS-3 150×4.6 mm, 5 μm Column Temperature: 50.0° C. Flow Rate: 1.5 mL/min Injection Volume: 20 μL Detection Wavelength: 280 nm Mobile Phase: A=Water:MeOH:TFA (95:5:0.1%; v/v/v) B=Water:MeOH:TFA (35:65:0.1%; v/v/v) Analysis Time: 50 min Quantitation limit: 0.05%
Detection limit: 0.02%
Gradient Profile:

| Time (min) | % A | % B | Curve |
|---|---|---|---|
| 0:00 | 100 | 0 | Initial |
| 45 | 50 | 50 | Linear |
| 48 | 100 | 0 | Linear |
| 55 | 100 | 0 | Hold |

Mobile Phase A (Water:MeOH:TFA::95:5:0.1%, v/v/v)
Mobile Phase B (Water:MeOH:TFA::35:65:0.1%, v/v/v)
MeOH=Methanol TFA=trifluoroacetic acid The synthesis and purification of R-MNTX were monitored using the above HPLC protocol. S-MNTX is distinguished from R-MNTX using the HPLC conditions described. Authentic S-MNTX for use as a standard may be made using the protocol as described herein. In a typical HPLC run, S-MNTX elutes about 0.5 minutes before R-MNTX elutes. The retention time of S-MNTX is approximately 9.3 minutes; the retention time of R-MNTX is about 9.8 minutes.

Figure 2:
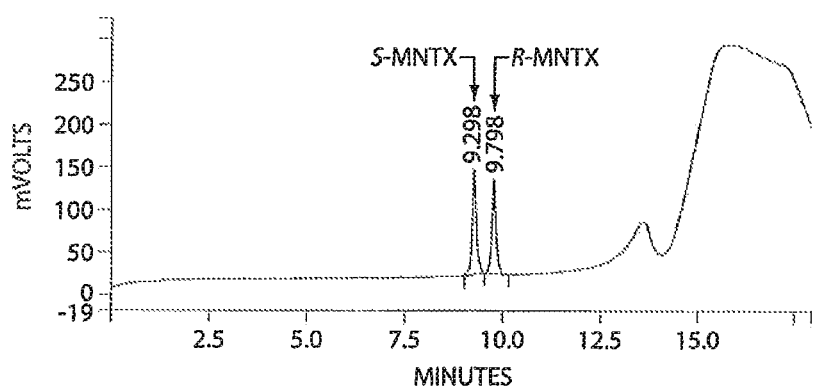
FIG. 2 is a chromatogram showing the separation of R and S forms of MNTX in a mixture of S- and R-MNTX.
Figure 3:
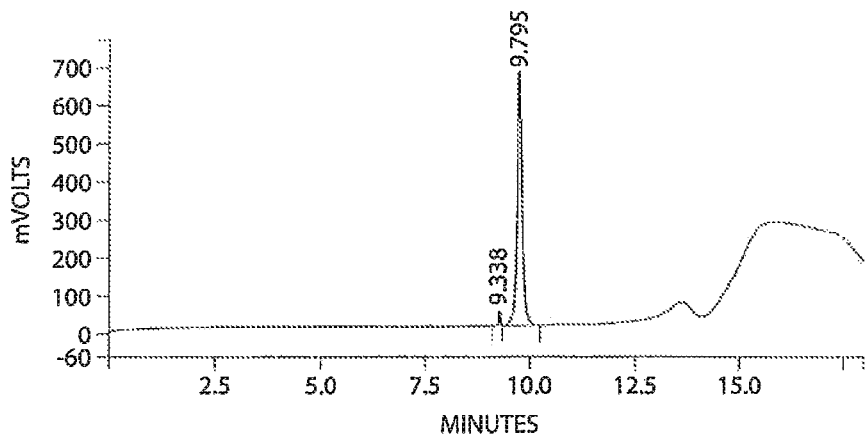
FIG. 3 is a chromatogram of R-MNTX with the addition of approximately 0.1% of the S-MNTX isomer.
Figure 4:
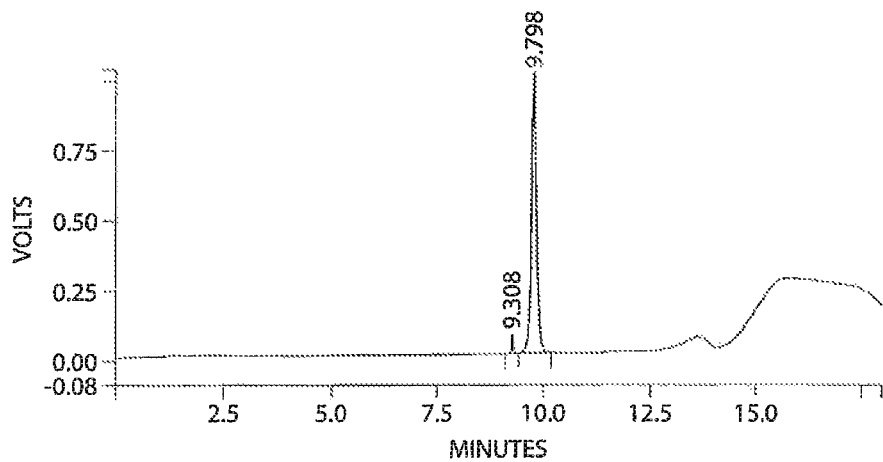
FIG. 4 is a chromatogram of R-MNTX with the addition of approximately 1.0% of the S-MNTX isomer.
Figure 5:
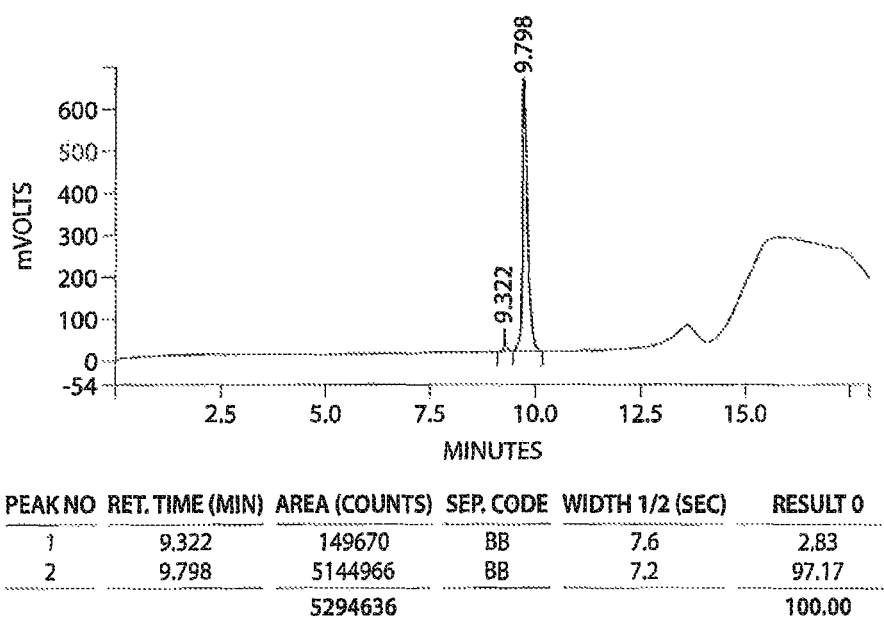
FIG. 5 is a chromatogram of R-MNTX with the addition of approximately 3.0% of the S-MNTX isomer.

As illustrated in FIG. 2, the S and R forms of MNTX can be distinguished clearly on an HPLC chromatogram. FIG. 3 is an HPLC chromatogram of a mixture of 0.1% by weight of authentic S form added to 99.5% by weight of authentic R form; FIG. 4 is a chromatogram of 1.0% by weight of authentic S form added to 99.0% by weight of authentic R form. FIG. 5 is a chromatogram of 3.0% by weight of authentic S form added to 98.0% by weight of authentic R form. This has permitted applicants to devise and test for the first time stereoselective protocols for synthesis and purification that yield highly pure R-MNTX from 3-O-protected-naltrexone.

Example 2

Stereoselective Synthesis of R-MNTX

Figure 6:
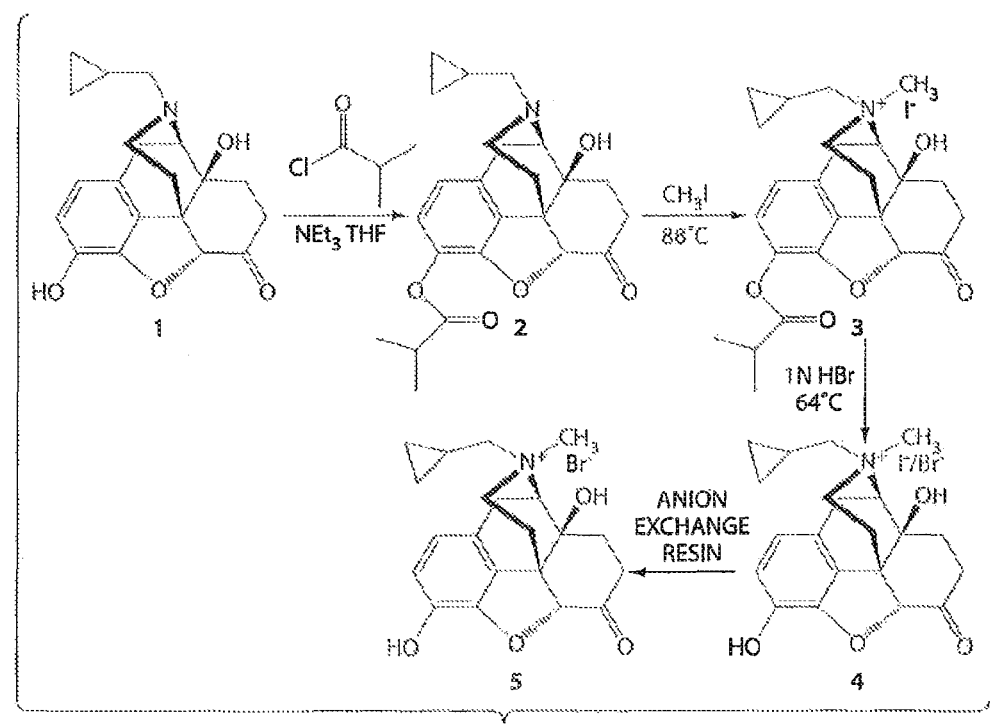
FIG. 6 shows a reaction scheme for the synthesis of R-MNTX using a preferred hydroxyl protecting group.

The synthetic scheme for Example 2 is shown in FIG. 6.
General.

All anhydrous reactions were carried out in oven-dried (130° C.) glassware under an atmosphere of dry nitrogen ($N_2$). All commercial reagents and solvents were used without any additional purification. Nuclear magnetic resonance (NMR) spectra were obtained using either a Varian Gemini or Varian Mercury 300 MHz spectrometer. Mass spectra were determined on a Finnigan LCQ. HPLC purity was determined using a Waters 717 Autosampler and Waters 996 Photodiode Array Detector.

3-O-Isobutyryl-Naltrexone (2)

To a solution of compound (1) (1.62 g, 4.75 mmol) in anhydrous tetrahydrofuran (THF) (120 mL) at 0° C. was added triethylamine (NEt3) (1.4 mL, 10 mmol). After the reaction was stirred for 15 min at 0° C., isobutyryl chloride (1.05 mL, 10 mmol) was added dropwise. Reaction mixture was stirred at 0° C. for 1 hr, then at room temperature for 18 hr before being quenched with saturated sodium bicarbonate ($NaHCO_3$) (aq) (70 mL) and 30 ml of $H_2O$. The reaction was extracted with methylene chloride ($CH_2Cl_2$) (2×200 mL). The extracts were combined, washed with brine (130 ml), dried over sodium sulfate ($Na_2SO_4$) (50 g), filtered and concentrated in vacuo. The crude material was purified by flash chromatography on silica gel (column size 40×450 mm, silica gel was loaded 40×190 mm) (9.8:0.2→9.6:0.4→9.4:0.6 $CH_2C_{12}$/MeOH) to give compound (2) (1.5 g 76.8%) as a white solid.

$^1$H NMR (300 MHz, $CDCl_3$) δ 6.82 (d, J=8.0 Hz, 1H), 6.67 (d, J=8.0 Hz, 1H), 4.69 (s, 1H), 3.21 (d, J=6.0 Hz, 1H), 3.12-2.96 (m, 2H), 2.93-2.82 (m, 1H), 2.71 (dd, J=4.5 Hz, 1H), 2.62 (dd, J=6.2 Hz, 1H), 2.48-2.28 (m, 4H), 2.19-2.10 (m, 1H), 1.93-1.86 (m, 1H), 1.68-1.59 (m, 2H), 1.34 (d, J=0.8 Hz, 3H, $CH_3$-isobutyryl), 1.31 (d, J=0.8 Hz, 3H, $CH_3$-isobutyryl), 0.90-0.83 (m, 1H, CH-cyclopropyl), 0.60-0.54 (m, 2H, $CH_2$-cyclopropyl), 0.18-0.13 (m, 2H, CH2-cyclopropyl). 13C NMR (75.5 MHz, $CDCl_3$) δ 207.6 (CO), 174.7 (COO/Pr) 147.8, 132.8, 130.1, 130.0, 122.8, 119.2, 90.5, 70.0, 61.9, 59.2, 50.6, 43.4, 36.1, 33.8, 31.2, 30.7, 22.9, 19.0, 18.9, 9.4, 4.0, 3.8. MS[M+H]$^+$: 412.

3-O-Isobutyryl-N-Methylnaltrexone Iodide Salt (3)

Compound (2) (689 mg, 1.67 mmol) was transferred by spatula into a glass pressure vessel. The vessel was purged gently with nitrogen on the manifold for 5 minutes and was then evacuated under high vacuum. When the vacuum was constant, the lower part of the vessel was immersed in liquid nitrogen. Methyl iodide (973 mg, 6.85 mmol) was dispensed into a separate flask on the manifold into a nitrogen atmosphere and frozen in liquid nitrogen. The frozen methyl iodide vessel was evacuated under high vacuum. The main manifold chamber was isolated from the high vacuum pump. The methyl iodide was allowed to warm to ambient temperature and sublime via the main chamber onto the liquid nitrogen cooled 3-O-Isobutyryl-Naltrexone. When sublimation was complete, nitrogen was slowly allowed to leach into the glass pressure vessel. The vessel was then sealed tight, removed from the manifold and heated in an oil bath at 88-90° C. for 17 hrs. The vessel was allowed to cool to ambient temperature before allowing nitrogen to flow into the vessel. The vessel was then evacuated under high vacuum to remove residues of unreacted methyl iodide giving a white solid. A sample of the solid was removed for $^1$H NMR analysis. This showed good conversion to product. Thin layer chromatography (TLC) of the product [dichloromethane/methanol 9:1 (v/v), normal phase silica, UV detection] showed a trace of starting material (2) ($R_f$=0.8) and a diffuse region ($R_f$=0-0.4). The solid was dissolved in dichloromethane/methanol (4:1, minimum volume) and applied to a silica gel column (ultrapure silica gel, 22 g in dichloromethane, bed dimensions: 200 mm×20 mm id). The column was eluted as follows:
Dichloromethane/methanol 98:2 (300 ml)
Dichloromethane/methanol 97:3 (300 ml)
Dichloromethane/methanol 94:6 (200 ml)
Dichloromethane/methanol 92:8 (400 ml)
Fractions were analyzed by TLC [dichloromethane/methanol 9:1 (v/v), normal phase silica, UV detection]. Fractions containing exclusively the principal component ($R_f$=0.4) were combined rinsing together with methanol, and concentrated to yield 867 mg of white solid. This represents a 91% yield based on 3-O-Isobutyryl-Naltrexone. $^1$H NMR is consistent.

N-Methylnaltrexone Bromide/Iodide Salt (4)

Compound (3) (862 mg, 1.56 mmol) was dissolved in methanol (13 ml). To this mixture was added sterile water (11.5 ml) followed by 48% aqueous hydrobromic acid (1.5 ml). The resultant mixture was stirred under nitrogen and heated in an oil bath at 64-65° C. for 6.5 hr. TLC analysis of a sample (dispersed in methanol) of the reaction mixture showed no starting material (3) remaining ($R_f$=0.4) and conversion to material at $R_f$=0-0.15. The mixture was concentrated on the rotary evaporator with the bath at 22-25° C. until approximately 1 ml of oily liquid remained. Acetonitrile (10 ml) was added and the mixture was reconcentrated. This was repeated a further three times, using 10 ml of acetonitrile, to give a ginger colored crisp foam (590 mg, 86% crude yield).

Preparation of Anion Exchange Resin Column.

30 g of AG 1-X8 resin was packed into an medium pressure liquid chromatography (MPLC) column (20 mm id) using 100 ml water to create a resin slurry. The resin bed was washed with 1.0N aqueous hydrobromic acid (200 ml) and then sterile water until the pH of the aqueous eluate was pH 6-7. Approximately 1.5 L of water was required.

N-Methylnaltrexone Bromide (5)

The foam (4) (597 mg) was dispersed in water (6 ml)/methanol (2 ml). Some dark oil remained undissolved. The clear supernatant liquid was decanted and applied to the prepared anion exchange resin column. The residue was washed twice with methanol (0.2 ml)/water (3 ml). The supernatant liquors were applied to the column. The column was eluted with 4.2 L of sterile water and fractions of ~20 ml were collected. The presence of N-Methylnaltrexone salt was detected by liquid chromatography/mass spectometry (LC/MS). The majority of N-Methylnaltrexone was located in the initial 1.5 L of eluate of which the first 600 ml contained the most pure material by TLC (4:1 dichloromethane/methanol, normal phase silica). The first 600 ml of eluate was combined and concentrated on the rotary evaporator to give a whitish glass. The water bath was maintained at ~35° C. Care was needed to control foaming of the eluate while evaporating.

Purification of N-Methylnaltrexone Bromide (5). Recrystallization from methanol.

The residue was warmed in methanol (60 ml) under nitrogen to just below reflux and then filtered through a glass sinter to remove a small amount of insoluble material. This filtrate was then blown down in a stream of nitrogen to approximately 10 ml and then cooled under nitrogen in ice/water. Some white precipitate was formed but clearly much solid remained in solution. The mixture was then concentrated by evaporation to give a slightly colored gum. This was triturated with methanol (3 ml×2). Methanol was cautiously decanted by pipette between triturations. The white residue was dissolved in methanol (60 ml) and filtered through a glass sinter. The filtrate was concentrated to approximately 1 ml and a further portion of methanol (1 ml) was added to triturate the solid. The supernatant liquors were decanted as before. The solid was dried to give a white solid, batch A (178.0 mg). HPLC analysis showed 97.31% of R-MNTX, and 2.69% of S-MNTX.

All filtrates/supernatant liquors in methanol were combined and concentrated to give a white glass. This residue was triturated with methanol (3 ml×2) and the supernatant liquors were removed carefully as before. The residue was dissolved in methanol (50 ml) and filtered through a glass sinter. The filtrate was concentrated to approximately 1 ml solution and a further portion of methanol (1 ml) was added to triturate the solid. The supernatant liquors were decanted as before and the residue was triturated further with methanol (2 ml). The supernatant liquors were decanted and the residue was dried to give a white solid, batch B (266.0 mg). HPLC analysis of batch B showed 97.39% of R-MNTX, and 2.61% of S-MNTX. Batches A and B together represent a total yield of 436.8 mg (64%). $^1$H NMR is consistent. MS [M+H]$^+$: 356.

As demonstrated in batches A and B, recrystallization from methanol yields product with high percentage of R-MNTX. In a reaction carried out under the same conditions with $^{14}$CH$_3$-labelled material, it was found that the composition of the crude reaction mixture before recrystallization from methanol was 94.4% R-MNTX* and 4.7% S-MNTX*. Recrystallization from methanol yielded product containing 98.0% R-MNTX* and 1.5% S-MNTX*. A second recrystallization from methanol yielded 98.3% R-MNTX* and 1.2% S-MNTX*.

It should be understood that it is believed that the synthetic protocol results in greater than 94% R form with only a small percentage of the S form. Using synthesis Scheme 1, the substantially pure material, could be processed further on a chromatography column, preparative HPLC or recrystallization. In one recrystallization following ion exchange, the purity of the R form was greater than 98%. A second recrystalization yielded 98.3% R-MNTX. It is understood that further recrystallizations and/or chromatography, anywhere between one and four, (or even six or as many as ten) times ensures greater than 99.95% R form and eliminates traces of the S form, if present.

Example 3

Stereoselective Synthesis of R-MNTX

Figure 7:
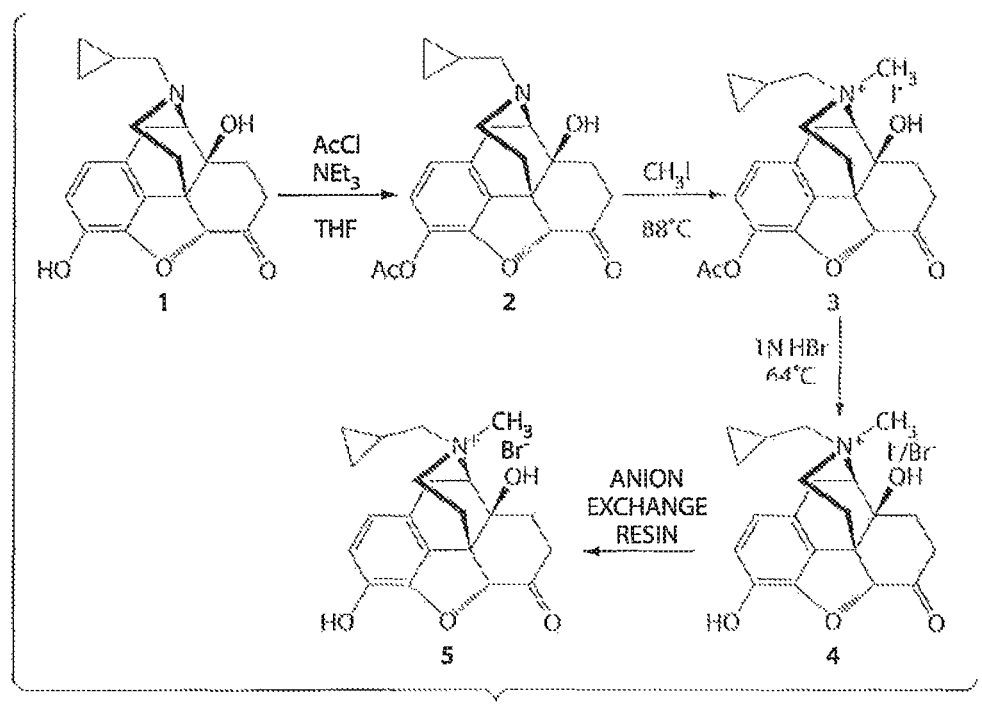
FIG. 7 shows an alternative reaction scheme for the synthesis of R-MNTX using a preferred hydroxyl protecting group.

The synthetic scheme for Example 3 is shown in FIG. 7. In Example 3, the method taught by Goldberg et al for protecting groups was followed. Acetyl, Goldberg et al's preferred protecting group, instead of isobutyryl was used as the protecting group. The reactions were carried out as described in Example 2. It was surprisingly found using the scheme shown in FIG. 7 that the acetyl protecting group tended to fall off during purification of intermediate 2 (O-acetyl-naltrexone). This made it difficult to obtain pure intermediate 2. The yield of intermediate 2 with the acetyl group was only 36.3% rendering the scheme shown in FIG. 7 unsuitable for commercial scale-up. In contrast using the synthetic scheme with isobutyryl as the protecting group (FIG. 6), intermediate 2 (3-O-isobutyryl-naltrexone) was quite stable during purification resulting in a yield of 76.8%.

Example 4

Manufacturing Process for a Pharmaceutical Formulation of R-MNTX

A manufacturing process can be outlined as follows:
1. Add required amount of water for injection (~80% or final volume) to a stainless steel tank.
2. Add chelating agent to the tank and stir till dissolved.
3. Add buffering agent to the tank and stir till dissolved.
4. Add R-MNTX to the tank and stir till dissolved.
5. Add isotonicity agent to the tank and stir till dissolved.
6. Adjust the pH of the solution to pH 3.25.
7. Add water for injection to increase the volume to the required amount.
8. Transfer material to supply pressure vessel.
9. Sterile filter into a sterile stainless steel pressure vessel.
10. Fill into bottles/vials, purge with nitrogen and then stopper the bottles/vials.
11. Sterilize the filled vials by autoclaving.

Exact Amount of Excipients to be Used:
Disodium edetate=0.75 mg/ml Added in step 2
Sodium citrate=0.199 mg/ml Added in step 3
Citric acid=0.35 mg/ml Added in step 3
Sodium chloride=8.5 mg/ml Added in step 5

The order of addition of excipients is described above. Steps 2 to 5 can take place in any order.

When all excipients and drug have been added, step 6, pH of the solution is adjusted by addition of acid. If a buffering agent is used in the solution, pH adjustment may not be required.

There are no specifics on the temperature or the stirring speed during the formulation. The temperature during formulation can be as high as 80° C.

Example 5

Preferred Manufacturing Process for a Pharmaceutical Formulation of R-MNTX

A preferred manufacturing process for 100 ml of 20 mg/ml solution of R-MNTX solution is as follows:
1. Add 80 ml of water for injection (~80% or final volume) to a stainless steel tank.
2. Add 75 mg of disodium edetate, a chelating agent, to the tank and stir till dissolved.
3. Add 19.9 mg of sodium citrate and 35 mg of citric acid (as buffering agents) to the tank and stir till dissolved.
4. Add 2000 mg of R-MNTX to the tank and stir till dissolved.
5. Add 850 mg of sodium chloride, an isotonicity agent, to the tank and stir till dissolved.
6. Adjust the pH of the solution if necessary.
7. Add water for injection to increase the volume to 100 ml.
8. Transfer the material to supply pressure vessel.
9. Sterile filter using a 0.22 micron filter into a sterile stainless steel pressure vessel.
10. Fill, purge with nitrogen and then stopper the bottles/vials.
11. Sterilize the filled vials by autoclaving.

Example 6

Preparation of a Subcutaneous Formulation of R-MNTX

A formula for a low citrate/EDTA formulation is listed below:

| Ingredient | mg/mL |
|---|---|
| R-MNTX | 30 mg |
| Sodium chloride | 4 mg |
| Citric acid | 0.0875 mg |
| Trisodium citrate | 0.0496 mg |
| Disodium edetate | 0.75 mg |
| Water for injection | q.s. to 1 g |

The pH of this solution is 3.5 and can withstand an autoclaving process.

Example 7

Manufacturing Process for a Lyophilized Pharmaceutical Formulation of R-MNTX

The lyophilization cycle is used for the preparation of lyophilized preparation of R-MNTX. Forty milligrams of R-MNTX is mixed with 32 mg of the cryoprotecting agent, mannitol and q.s. to 1 mL using water for injection.
1. Load chamber at room temperature (20-25° C.)
2. Lower shelf temp to −45 degrees C. at 1.0 degrees C./min
3. Hold shelf temp at −45 for 120 minutes
4. When condenser is below −50 degrees C., evacuate the chamber to 100-125 mt.
5. Ramp shelf to −20 degrees C. at 0.5 degrees C./min
6. Hold at −20 degrees C. for 16 hours
7. Ramp shelf to +27 degrees C. at 0.10 degrees C./min
8. Hold for a minimum of 8 hours. Maintain chamber pressure at 100-125 mt for the entire cycle.
9. Restore chamber to 11.0 PSIA+ or −1.0 with sterile filtered Nitrogen and then seat the closures (2" Hg), then bleed to atmospheric pressure with $N_2$ to unload. The pH of the solution after lyophilization and reconstitution is 5.0.

The disclosures of all patents, patent applications and scientific publications cited or referenced herein are incorporated by reference in their entirety, including the U.S. patent application Ser. No. 11/441,452, titled: "(S)-N-METHYLNALTREXONE", filed on May 25, 2006, now U.S. Pat. No. 7,563,899, issued on Jul 21, 2009. In case of conflict between documents incorporated by reference and the instant application, the instant application will control.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A composition comprising R-MNTX, wherein the composition is free of HPLC detectable S-MNTX at a detection limit of 0.02% and at a quantitation limit of 0.05%, and a chelating agent or an isotonicity agent.

2. A composition comprising MNTX, wherein at least 99.6%, 99.7%, 99.8%, 99.85%, 99.9%, or 99.95% of the MNTX in the composition is in the R configuration with respect to nitrogen, and a chelating agent.

3. The composition of claim 1 or 2, wherein the MNTX present in the composition is a cation of a salt, paired by an anion.

4. The composition of claim 3, wherein the anion is a halide, sulfate, phosphate, nitrate or an organic-charged anionic species.

5. The composition of claim 4, wherein the halide is bromide, chloride, iodide, or fluoride.

6. The composition of claim 4, wherein the halide is bromide.

7. The composition of claim 2, wherein at least 99.85% of the MNTX in the composition is in the R configuration with respect to nitrogen.

8. The composition of claim 1 or 2, wherein the composition further comprises a buffering agent selected from the group consisting of citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate and benzoic acid, or combinations thereof.

9. The composition of claim 8, wherein the buffering agent comprises glycine.

10. The composition of claim 1 or 2, wherein the chelating agent is selected from the group consisting of ethylenediaminetetraacetic acid (EDTA), a derivative thereof, citric acid, a derivative thereof, niacinamide, a derivative thereof, sodium desoxycholate, a derivative thereof, L-glutamic acid, N,N-diacetic acid, a derivative thereof, and a combination thereof.

11. The composition of claim 1 or 2, wherein the chelating agent comprises a derivative of EDTA.

12. The composition of claim 1, wherein the isotonicity agent is selected from the group consisting of sodium chloride, mannitol, lactose, dextrose, glycerol, sorbitol, and a combination thereof.

13. The composition of claim 1, wherein the isotonicity agent comprises sodium chloride.

14. The composition of claim 1 or 2, wherein the composition is an aqueous formulation.

15. The composition of claim 14, wherein the composition is suitable for parenteral delivery.

16. The composition of claim 1 or 2, wherein the composition is a solid formulation.

17. The composition of claim 16, wherein the composition is a tablet.

18. The composition of claim 16, wherein the composition is suitable for oral delivery.

19. The composition of claim 17, wherein the composition is suitable for oral delivery.

20. A method for treating an opioid-induced peripheral side effect comprising administering to a patient the composition of claim 1 or 2 in an amount effective to treat the side effect.

21. The method of claim 20, wherein the opioid induced peripheral side effect is constipation.

22. The composition of claim 2, wherein the composition comprises an isotonicity agent.

23. The composition of claim 16, wherein the composition is delivered orally at a dose from about 0.25 to 19.0 mg/kg body weight per day.

24. The composition of claim 1 or 2, wherein the composition further comprises stearic acid.

25. The composition of claim 1 or 2, wherein the composition further comprises polyethylene glycol.

26. The composition of claim 1 or 2, wherein the composition further comprises polyvinyl alcohol.

* * * * *